(12) United States Patent
Los et al.

(10) Patent No.: US 11,339,379 B2
(45) Date of Patent: *May 24, 2022

(54) MALATE DEHYDROGENASES

(71) Applicant: DSM IP ASSETS B.V., Heerlen (NL)

(72) Inventors: Alrik Pieter Los, Echt (NL); Rene Marcel De Jong, Echt (NL); Remko Tsjibbe Winter, Echt (NL); Ben Den Dulk, Echt (NL)

(73) Assignee: DSM IP ASSETS B.V., Heerlen (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/999,962

(22) Filed: Aug. 21, 2020

(65) Prior Publication Data

US 2020/0385692 A1 Dec. 10, 2020

Related U.S. Application Data

(62) Division of application No. 16/316,988, filed as application No. PCT/EP2017/067318 on Jul. 11, 2017, now Pat. No. 10,787,649.

(30) Foreign Application Priority Data

Jul. 13, 2016 (EP) .................................. 16179315

(51) Int. Cl.
| | |
|---|---|
| *C12N 9/04* | (2006.01) |
| *C12P 7/46* | (2006.01) |
| *C12N 1/20* | (2006.01) |
| *C12N 15/00* | (2006.01) |
| *C12N 1/14* | (2006.01) |
| *C12N 1/18* | (2006.01) |
| *C12R 1/865* | (2006.01) |

(52) U.S. Cl.
CPC ............. *C12N 9/0006* (2013.01); *C12N 1/14* (2013.01); *C12N 1/185* (2021.05); *C12N 15/00* (2013.01); *C12P 7/46* (2013.01); *C12Y 101/01037* (2013.01); *C12R 2001/865* (2021.05)

(58) Field of Classification Search
CPC .................................. C12N 9/0006; C12P 7/46
See application file for complete search history.

(56) References Cited

U.S. PATENT DOCUMENTS

| | | |
|---|---|---|
| 9,012,187 B2 | 4/2015 | Jansen et al. |
| 9,340,804 B2 | 5/2016 | Verwaal et al. |
| 9,340,805 B2 | 5/2016 | Jansen et al. |
| 9,689,005 B2 | 6/2017 | Verwaal et al. |
| 2011/0081694 A1 | 4/2011 | Verwaal et al. |
| 2012/0165569 A1 | 6/2012 | Verwaal et al. |
| 2012/0219999 A1 | 8/2012 | Fischer et al. |
| 2014/0031587 A1 | 1/2014 | Verwaal et al. |

FOREIGN PATENT DOCUMENTS

| | | |
|---|---|---|
| CN | 102089436 A | 6/2011 |
| EP | 2149607 A1 | 2/2010 |
| EP | 2495304 A1 | 9/2012 |
| WO | 2008/144626 A1 | 11/2008 |
| WO | 2009/065778 A1 | 5/2009 |
| WO | 2014/018755 A1 | 1/2014 |
| WO | 2014/018757 A1 | 1/2014 |

OTHER PUBLICATIONS

Nishiyama M. et al., "Alteration of Coenzyme Specificity of Malate Dehydrogenase from Thermus Flavus by Site-directed Mutagenesis", The Journal of Biological Chemistry, Mar. 5, 1993, pp. 4656-4660, vol. 268, No. 7.
Tomita, Takeo et al., "Structural basis for the alteration of coenzyme specificity in malate dehydrogenase mutant", Biochemical and Biophysical Research Communications, Aug. 25, 2006, pp. 502-508, vol. 347, No. 2.
Database UniProt [Online], Jan. 15, 2008, XP002765251, retrieved from EBI accession No. Uniprot: Q4JV42 Database accession No. Q4JV42 sequence.
Database UniProt [Online], Feb. 1, 2005, XP002765252, retrieved from EBI accession No. UNIPROT:Q5NE17, Database accession No. Q5NE17 sequence.
Zelle, Rintze M. et al., "Malic acid production by *Saccharomyces cerevisiae*: engineering of pyruvate carboxylation, oxaloacetate reduction, and malate export", Applied and Environmental Microbiology, May 1, 2008, pp. 2766-2777, vol. 74, No. 9.
Steffan, Joan S. et al., "Isolation and Characterization of the Yeast Gene Encoding the MDH3 Isozyme of Malate Dehydrogenase", The Journal of Biological Chemistry, Dec. 5, 1992, pp. 24708-24715, vol. 267, No. 34.
Musrati, R. A. et al., "Malate Dehydrogenase: Distribution, Function and Properties", General Physiology and Biophysics, Jan. 1, 1998, pp. 193-210, vol. 17, No. 3.
Minarik, P. et al., "Malate Dehydrogenases—Structure and Function", General Physiology and Biophysics, Sep. 1, 2002, pp. 257-265, vol. 21.
International Search Report of International Patent Application No. PCT/EP2017/067318 dated Sep. 18, 2017.
Studer. Residue mutations and their impact on protein structure and function: detecting beneficial and pathogenic changes. Biochem. J. (2013) 449, 581-594.
Database UniProt [Online], Jan. 7, 2022, P32419, retrieved from EBI accession No. Uniprot: Q12689, Database accession No. Q12689 sequence, pp. 1-3.
"Coenzyme Alteration of Malate Dehydrogenase and its Physiological Roles in *Escherichia coli*," a dissertation, published Feb. 15, 2013, 76 pages.

*Primary Examiner* — Yong D Pak
(74) *Attorney, Agent, or Firm* — McBee Moore & Vanik IP, LLC

(57) ABSTRACT

The present invention relates to a recombinant host cell which is capable of producing a dicarboxylic acid and which comprises a mutant malate dehydrogenase resulting in an increased production of the dicarboxylic acid. The invention also relates to a process for producing a dicarboxylic acid, which method comprises fermenting said recombinant host cell in a suitable fermentation medium and producing the dicarboxylic acid.

18 Claims, 10 Drawing Sheets

Specification includes a Sequence Listing.

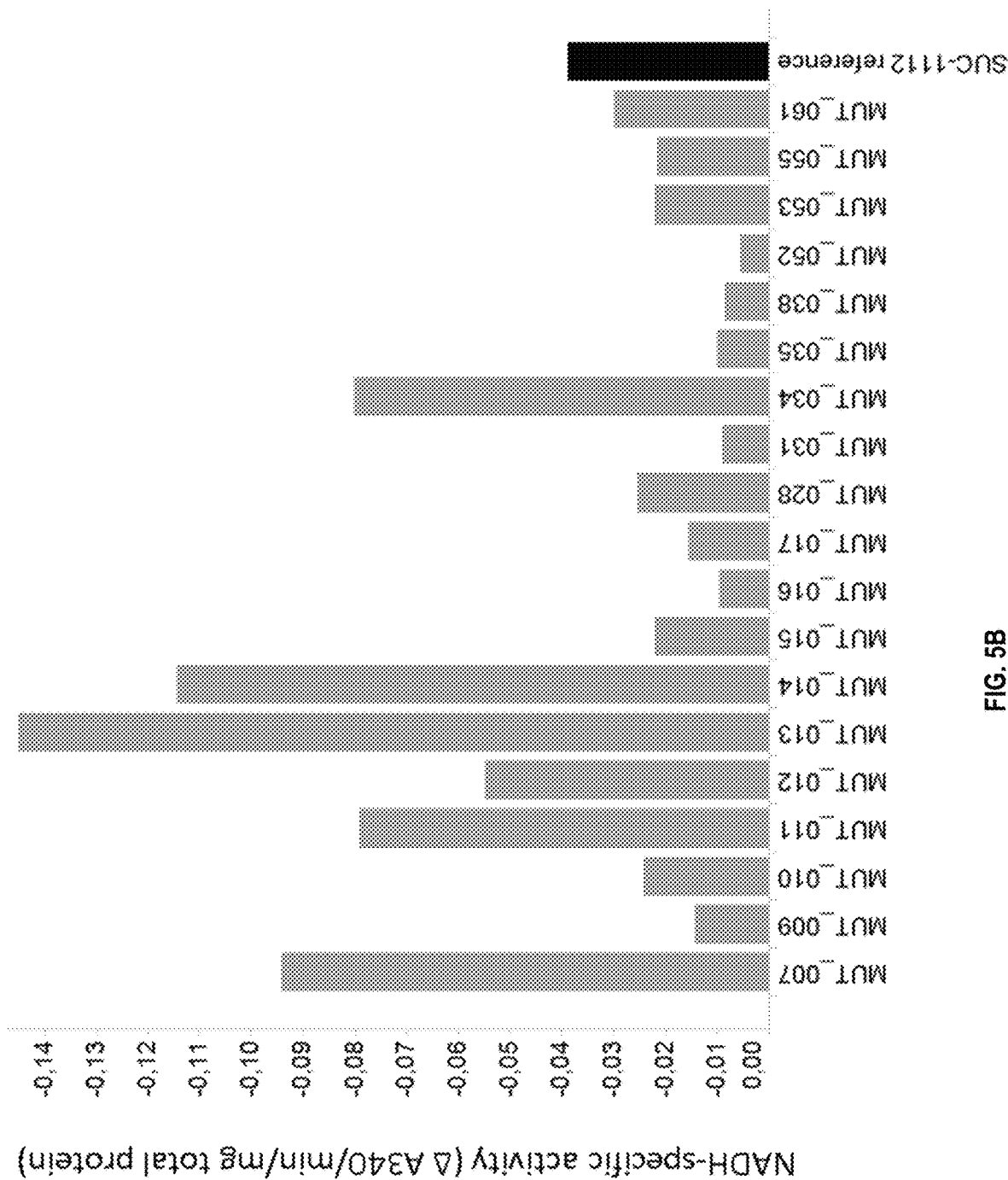

MALATE DEHYROGENASES

CROSS-REFERENCE TO RELATED APPLICATIONS

This application is a Divisional of U.S. patent application Ser. No. 16/316,988, filed 10 Jan. 2019, which is a National Stage entry of International Application No. PCT/EP2017/067318, filed 11 Jul. 2017, which claims priority to European Patent Application No. 16179315.3, filed 13 Jul. 2016. Each of these applications is incorporated by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2919208-497001_Sequence_Listing_ST25.txt" created on 12 Aug. 2020, and 143,341 bytes in size) is submitted concurrently with the instant application, and the entire contents of the Sequence Listing are incorporated herein by reference.

FIELD OF THE INVENTION

The present invention relates to a recombinant host cell capable of producing a dicarboxylic acid, and a method for producing a dicarboxylic acid using said recombinant host cell.

BACKGROUND TO THE INVENTION

The 4-carbon dicarboxylic acids malic acid, fumaric acid and succinic acid are potential precursors for numerous chemicals. For example, succinic acid can be converted into 1,4-butanediol (BDO), tetrahydrofuran, and gamma-butyrolactone. Another product derived from succinic acid is a polyester polymer which is made by linking succinic acid and BDO.

Succinic acid for industrial use is predominantly petrochemically produced from butane through catalytic hydrogenation of maleic acid or maleic anhydride. These processes are considered harmful for the environment and costly. The fermentative production of succinic acid is considered an attractive alternative process for the production of succinic acid, wherein renewable feedstock as a carbon source may be used.

Several studies have been carried out on the fermentative production of C4-dicarboxylic acid in (recombinant) yeast.

EP2495304, for example, discloses a recombinant yeast suitable for succinic acid production, genetically modified with genes encoding a pyruvate carboxylase, a phosphoenolpyruvate carboxykinase, a malate dehydrogenase, a fumarase, a fumarate reductase and a succinate transporter.

Despite the improvements that have been made in the fermentative production of dicarboxylic acid in host cells, such as yeast, there nevertheless remains a need for further improved host cells for the fermentative production of dicarboxylic acids.

SUMMARY OF THE INVENTION

The present invention relates to a recombinant host cell which is capable of producing a dicarboxylic acid and which comprises a mutant polypeptide having malate dehydrogenase (MDH) activity. Surprisingly, it was found that the host cell according to the present invention produces an increased amount of a dicarboxylic acid as compared to the amount of dicarboxylic acid produced by a host cell comprising a reference MDH polypeptide, the reference MDH polypeptide being typically a NAD(H)-dependent malate dehydrogenase (EC 1.1.1.37).

According to the present invention, there is thus provided a recombinant host cell which is capable of producing a dicarboxylic acid and which comprises a nucleic acid sequence encoding a mutant polypeptide having malate dehydrogenase activity, wherein the mutant polypeptide comprises an amino acid sequence which, when aligned with the malate dehydrogenase comprising the sequence set out in SEQ ID NO: 39, comprises one mutation (e.g. one substitution) of an amino acid residue corresponding to amino acid 34 in SEQ ID NO: 39. Said mutant polypeptide having malate dehydrogenase activity may further comprise one or more additional mutations (e.g. substitutions). In particular, the mutant polypeptide having malate dehydrogenase activity may further comprise one or more additional mutations (e.g. substitutions) corresponding to any of amino acids 35, 36, 37, 38, 39 and/or 40 in SEQ ID NO: 39.

According to the present invention, there is also provided a recombinant host cell which is capable of producing a dicarboxylic acid and which comprises a nucleic acid sequence encoding a mutant polypeptide having malate dehydrogenase activity, wherein the mutant polypeptide has an increase in the NADP(H)-relative to NAD(H)-dependent activity as compared to that of a reference MDH polypeptide, the reference MDH polypeptide being typically a NAD(H)-dependent malate dehydrogenase (EC 1.1.1.37). In said embodiment, said mutant polypeptide may be a mutant polypeptide comprising an amino acid sequence which, when aligned with the malate dehydrogenase comprising the sequence set out in SEQ ID NO: 39, comprises one mutation (e.g. one substitution) of an amino acid residue corresponding to amino acid 34 in SEQ ID NO: 39.

The invention also provides:
- a recombinant host cell according to the present invention, wherein the nucleic sequence encoding the mutant polypeptide having malate dehydrogenase activity is expressed in the cytosol and the mutant polypeptide having malate dehydrogenase activity is active in the cytosol.
- a recombinant host cell according to the present invention, wherein the recombinant host cell has an active reductive tricarboxylic acid (TCA) pathway from phosphoenol or pyruvate to succinate.
- a method for the production of a dicarboxylic acid, wherein the method comprises fermenting the recombinant host cell of the present invention under conditions suitable for production of the dicarboxylic acid. The dicarboxylic acid may be succinic acid, malic acid and/or fumaric acid. The method may further comprise recovering the dicarboxylic acid from the fermentation medium.

BRIEF DESCRIPTION OF THE DRAWINGS

FIG. 5B: NADH-specific malate dehydrogenase (MDH) activity of MDH mutants expressed in strain SUC-1112 (see Table 1 for specific mutations). Shown is activity, depicted as Δ A340/min/mg total protein. The value is negative as MDH-dependent NADH oxidation results in a decrease in absorbance at 340 nm. A more negative value indicates more activity. The activity was measured as described in Example 5.

DESCRIPTION OF THE SEQUENCE LISTING

Figure 1:
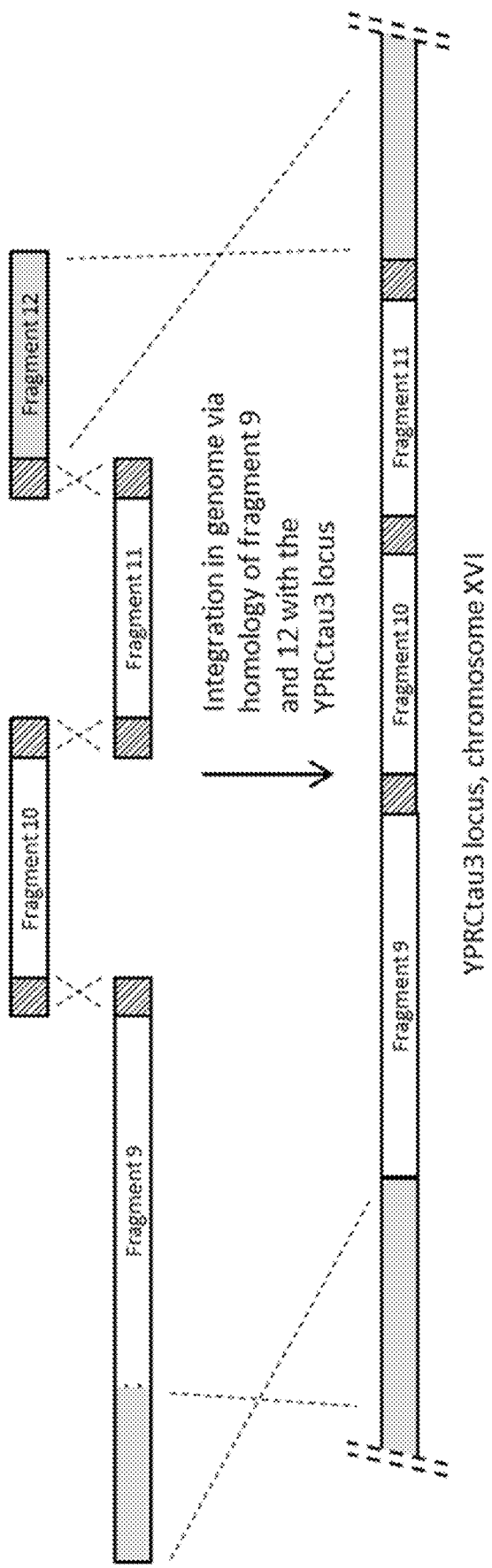
FIG. 1 sets out a schematic depiction of integration of fragments 9 to 12. The hatched parts indicated in fragments 9 to 12 denote the unique homologous overlap regions leading to the recombination events as indicated by the dashed crosses between the homologous regions. The 5' end of fragment 9 and the 3' end of fragment 12 (indicated by the grey regions in fragments 9 and 12) are homologous to the YPRCtau3 locus on chromosome 16. Homologous recombination results in integration of fragment 10 and 11 into the YPRCtau3 locus.

SEQ ID NO: 1 sets out the nucleotide sequence of fragment 2 (FIG. 2), which includes PEP carboxykinase from *Actinobacillus succinogenes* codon pair optimized for expression in *Saccharomyces cerevisiae*.

SEQ ID NO: 2 sets out the nucleotide sequence of fragment 3 (FIG. 2), which includes pyruvate carboxylase (PYC2) from *S. cerevisiae* codon pair optimized for expression in *S. cerevisiae*.

SEQ ID NO: 3 sets out the nucleotide sequence of the PCR template for fragment 4 (FIG. 2), which includes a KanMX selection marker functional in *S. cerevisiae*.

SEQ ID NO: 4 sets out the nucleotide sequence of fragment 5 (FIG. 2), which includes a putative dicarboxylic acid transporter from *Aspergillus niger* codon pair optimized for expression in *S. cerevisiae*.

SEQ ID NO: 5 sets out the nucleotide sequence of fragment 6 (FIG. 2), which includes malate dehydrogenase (MDH3) from *S. cerevisiae* codon pair optimized for expression in *S. cerevisiae*.

SEQ ID NO: 6 sets out the nucleotide sequence of fragment 7 (FIG. 2), which includes fumarase (fumB) from *Escherichia coli* codon pair optimized for expression in *S. cerevisiae*.

SEQ ID NO: 7 sets out the nucleotide sequence of fragment 8 (FIG. 2), which includes fumarate reductase from *Trypanosoma brucei* (FRDg) codon pair optimized for expression in *S. cerevisiae*.

SEQ ID NO: 8 sets out the amino acid sequence of fumarate reductase from *Trypanosoma brucei* (FRDg).

Figure 2:
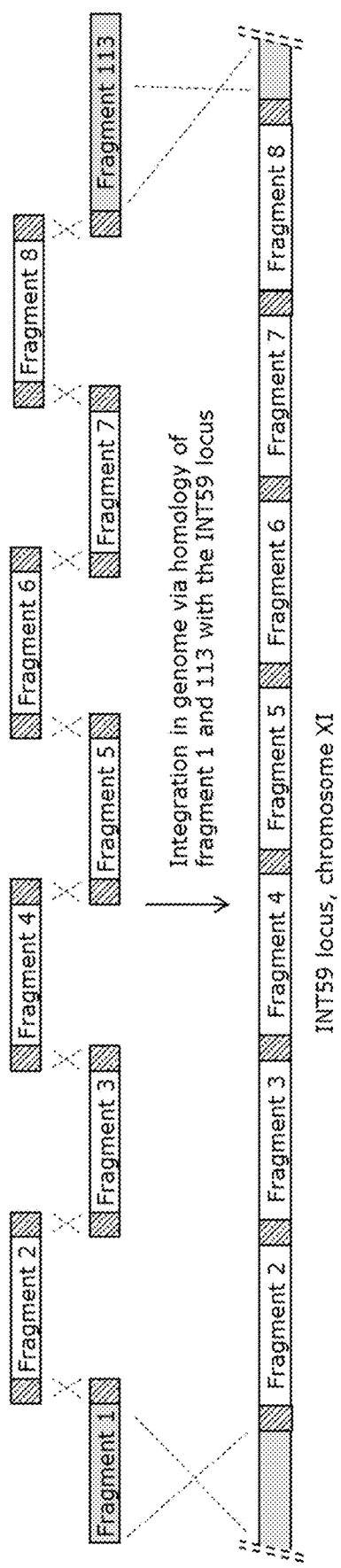
FIG. 2 sets out a schematic depiction of integration of fragments 1-8 and fragment 113. The hatched parts indicated in fragments 1-8 and 113 denote the unique homologous overlap regions leading to the recombination events as indicated by the dashed crosses between the homologous regions. Fragment 1 and fragment 113 are homologous to the INT59 locus on chromosome XI, homologous recombination results in integration of fragment 2-8 into the INT59 locus.

SEQ ID NO: 9 sets out the nucleotide sequence of the primer used to generate fragment 1 (FIG. 2).

SEQ ID NO: 10 sets out the nucleotide sequence of the primer used to generate fragment 1 (FIG. 2).

SEQ ID NO: 11 sets out the nucleotide sequence of the primer used to generate fragment 2 (FIG. 2).

SEQ ID NO: 12 sets out the nucleotide sequence of the primer used to generate fragment 2 (FIG. 2).

SEQ ID NO: 13 sets out the nucleotide sequence of the primer used to generate fragment 3 (FIG. 2).

SEQ ID NO: 14 sets out the nucleotide sequence of the primer used to generate fragment 3 (FIG. 2).

SEQ ID NO: 15 sets out the nucleotide sequence of the primer used to generate fragment 4 (FIG. 2).

SEQ ID NO: 16 sets out the nucleotide sequence of the primer used to generate fragment 4 (FIG. 2).

SEQ ID NO: 17 sets out the nucleotide sequence of the primer used to generate fragment 5 (FIG. 2).

SEQ ID NO: 18 sets out the nucleotide sequence of the primer used to generate fragment 5 (FIG. 2).

Figure 7:
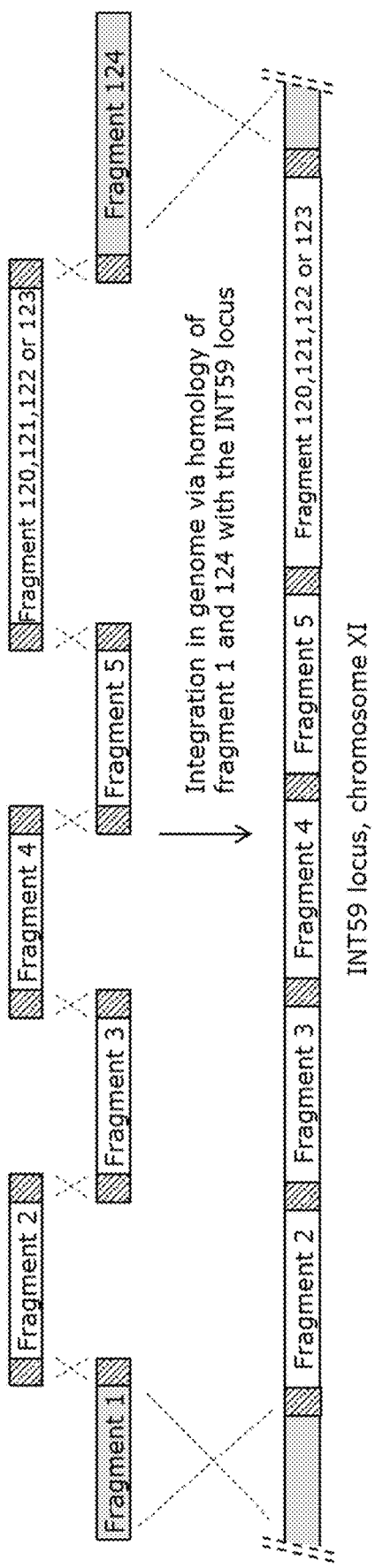
FIG. 7 sets out a schematic depiction of integration of fragments 1-5, 124 and fragment 120, 121, 122 or 123. The hatched parts indicated in the fragments denote the unique homologous overlap regions leading to the recombination events as indicated by the dashed crosses between the homologous regions. Fragment 1 and fragment 124 are homologous to the INT59 locus on chromosome XI, homologous recombination results in integration of fragment 2-5 and 120, 121, 122 or 123 into the INT59 locus.

SEQ ID NO: 19 sets out the nucleotide sequence of the primer used to generate fragment 6 (FIG. 2) and fragments 120, 121, 122 and 123 (FIG. 7).

SEQ ID NO: 20 sets out the nucleotide sequence of the primer used to generate fragment 6 (FIG. 2) and fragments 120, 121, 122 and 123 (FIG. 7).

SEQ ID NO: 21 sets out the nucleotide sequence of the primer used to generate fragment 7 (FIG. 2).

SEQ ID NO: 22 sets out the nucleotide sequence of the primer used to generate fragment 7 (FIG. 2).

SEQ ID NO: 23 sets out the nucleotide sequence of the primer used to generate fragment 8 (FIG. 2).

SEQ ID NO: 24 sets out the nucleotide sequence of the primer used to generate fragment 8 (FIG. 2).

Figure 3:
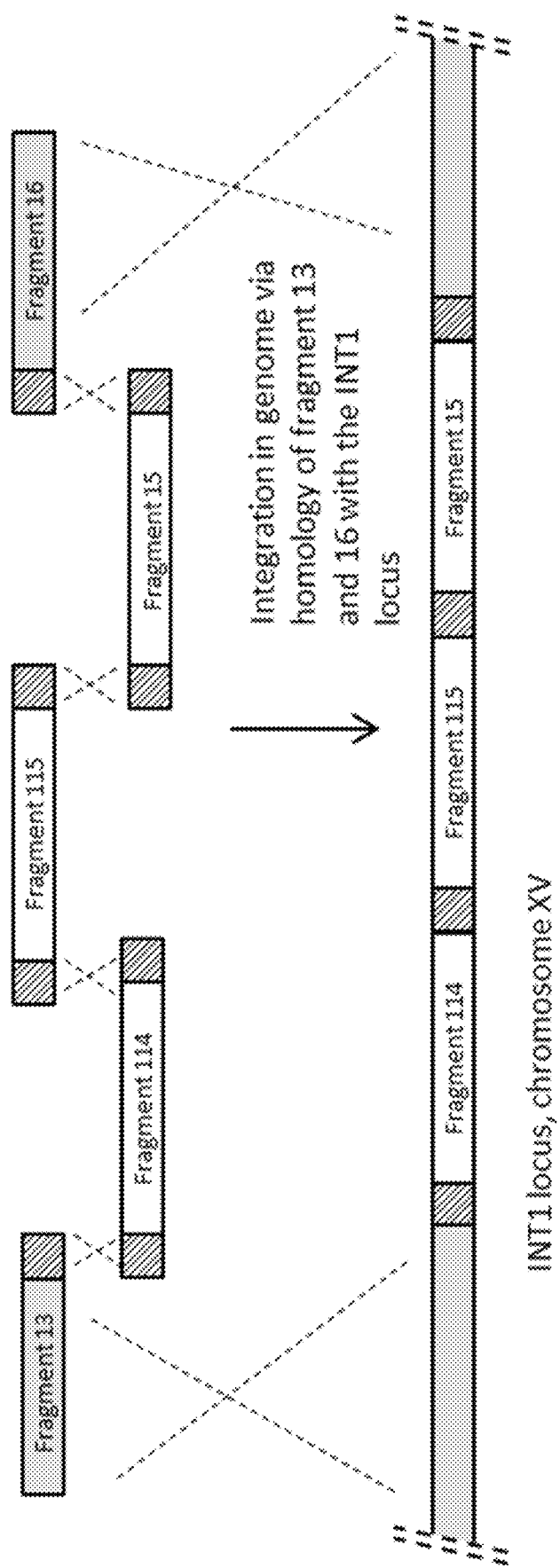
FIG. 3 sets out a schematic depiction of integration of fragments 13, 114, 115, 15 and 16. The hatched parts indicated in fragments 13, 114, 115, 15 and 16 denote the unique homologous overlap regions leading to the recombination events as indicated by the dashed crosses between the homologous regions. Fragment 13 and fragment 16 are homologous to the INT1 locus on chromosome XV, homologous recombination results in integration of fragment 114, 115 and 15 into the INT1 locus.

SEQ ID NO: 25 sets out the nucleotide sequence of the primer used to generate fragment 13 (FIG. 3).

SEQ ID NO: 26 sets out the nucleotide sequence of the primer used to generate fragment 13 (FIG. 3).

Figure 4:
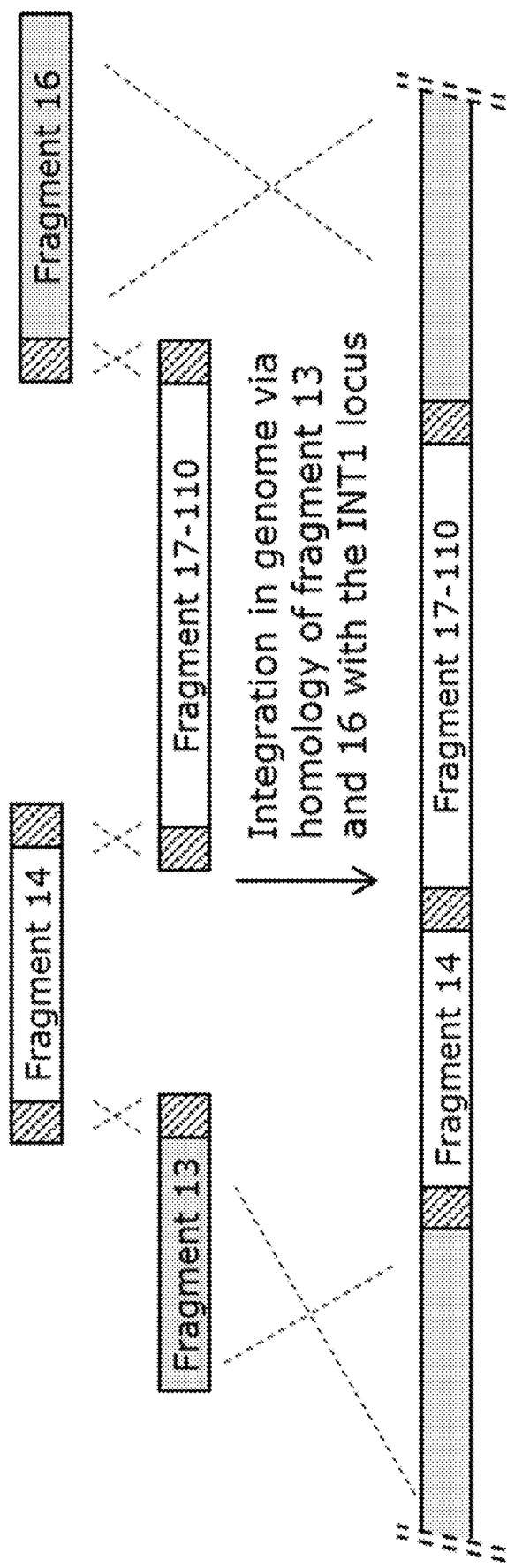
FIG. 4 sets out a schematic depiction of integration of fragments 13, 14, 16 and one of the fragments 17-110. The hatched parts indicated in fragments 13, 14, 16 and fragment 17-110 denote the unique homologous overlap regions leading to the recombination events as indicated by the dashed crosses between the homologous regions. Fragment 13 and fragment 16 are homologous to the INT1 locus on chromosome XV, homologous recombination results in integration of fragment 14 and one of the fragments 17-112 into the INT1 locus.

SEQ ID NO: 27 sets out the nucleotide sequence of the primer used to generate fragment 14 (FIG. 4).

SEQ ID NO: 28 sets out the nucleotide sequence of the primer used to generate fragment 115 (FIG. 3) and fragment 14 (FIG. 4).

SEQ ID NO: 29 sets out the nucleotide sequence of the primer used to generate fragment 15 (FIG. 3) and fragments 17 to 110 (FIG. 4).

SEQ ID NO: 30 sets out the nucleotide sequence of the primer used to generate fragment 15 (FIG. 3) and fragments 17 to 110 (FIG. 4).

SEQ ID NO: 31 sets out the nucleotide sequence of fragment 15 (FIG. 3) and fragment 120 (FIG. 7), which includes the nucleotide sequence encoding SEQ ID NO: 39 codon pair optimized for expression in *S. cerevisiae*.

SEQ ID NO: 32 sets out the nucleotide sequence of the primer used to generate fragment 16 (FIG. 3).

SEQ ID NO: 33 sets out the nucleotide sequence of the primer used to generate fragment 16 (FIG. 3).

SEQ ID NO: 34 sets out the nucleotide sequence of fragment 9 (FIG. 1), which includes fumarase from *Rhizopus oryzae* codon pair optimized for expression in *Saccharomyces cerevisiae*.

SEQ ID NO: 35 sets out the nucleotide sequence of fragment 10 (FIG. 1), which includes the 5' part of the Cre-recombinase.

SEQ ID NO: 36 sets out the nucleotide sequence of fragment 11 (FIG. 1), which includes the 3' part of the Cre-recombinase.

SEQ ID NO: 37 sets out the nucleotide sequence of fragment 12 (FIG. 1), which includes a region homologous to the YPRCtau3 locus.

SEQ ID NO: 38 sets out the nucleotide sequence of the PCR template for fragment 115 (FIG. 3), fragment 14 (FIG. 4) and fragment 117 (FIG. 6), which includes the nourseothricin selection marker.

SEQ ID NO: 39 sets out the amino acid sequence of the malate dehydrogenase (MDH3) protein from *S. cerevisiae*, lacking the 3 C-terminal peroxisomal targeting sequence.

SEQ ID NO: 40 sets out the nucleotide sequence of the primer used to generate fragment 113 (FIG. 2).

SEQ ID NO: 41 sets out the nucleotide sequence of the primer used to generate fragment 113 (FIG. 2).

SEQ ID NO: 42 sets out the nucleotide sequence of fragment 114 (FIG. 3), which includes the expression cassette of ZWF1 from *S. cerevisiae* codon pair optimized for expression in *S. cerevisiae*.

SEQ ID NO: 43 sets out the nucleotide sequence of the primer used to generate fragment 114 (FIG. 3).

SEQ ID NO: 44 sets out the nucleotide sequence of the primer used to generate fragment 114 (FIG. 3).

SEQ ID NO: 45 sets out the nucleotide sequence of the primer used to generate fragment 115 (FIG. 3).

SEQ ID NO: 46 sets out the amino acid sequence of the pyruvate carboxylase protein from *S. cerevisiae*.

SEQ ID NO: 47 sets out the amino acid sequence of phosphoenolpyruvate carboxykinase from *Actinobacillus succinogenes*, with EGY to DAF modification at position 120-122.

SEQ ID NO: 48 sets out the amino acid sequence of fumarase (fumB) from *Escherichia coli*.

SEQ ID NO: 49 sets out the amino acid sequence of fumarase from *Rhizopus oryzae*, lacking the first 23 N-terminal amino acids.

SEQ ID NO: 50 sets out the amino acid sequence of a putative dicarboxylic acid transporter from *Aspergillus niger*.

SEQ ID NO: 51 sets out the amino acid sequence of isocitrate lyase from *Kluyveromyces lactis*.

SEQ ID NO: 52 sets out the amino acid sequence of *Saccharomyces cerevisiae* peroxisomal malate synthase (Mls1) amino acid sequence, lacking the 3 C-terminal peroxisomal targeting sequence.

SEQ ID NO: 53 sets out the amino acid sequence of the malate dehydrogenase (MDH3) protein from *S. cerevisiae*, including the peroxisomal targeting sequence SKL.

Figure 6:
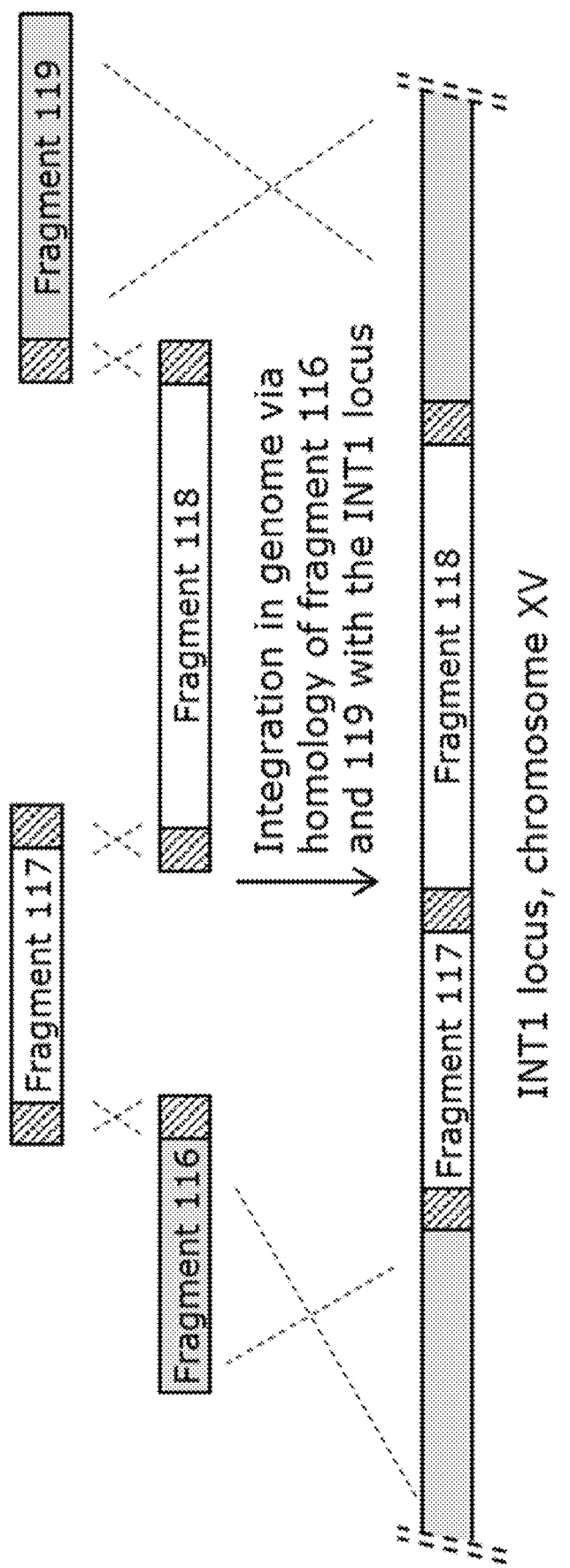
FIG. 6 sets out a schematic depiction of integration of fragments 116, 117, 118 and fragment 119. The hatched parts indicated in fragments 116, 117, 118 and fragment 119 denote the unique homologous overlap regions leading to the recombination events as indicated by the dashed crosses between the homologous regions. Fragment 116 and fragment 119 are homologous to the INT1 locus on chromosome XV, homologous recombination results in integration of fragment 117 and fragment 118 into the INT1 locus.

SEQ ID NO: 54 sets out the nucleotide sequence of the primer used to generate fragment 116 (FIG. 6).

SEQ ID NO: 55 sets out the nucleotide sequence of the primer used to generate fragment 116 (FIG. 6).

SEQ ID NO: 56 sets out the nucleotide sequence of the primer used to generate fragment 117 (FIG. 6).

SEQ ID NO: 57 sets out the nucleotide sequence of the primer used to generate fragment 117 (FIG. 6).

SEQ ID NO: 58 sets out the nucleotide sequence of the primer used to generate fragment 119 (FIG. 6).

SEQ ID NO: 59 sets out the nucleotide sequence of the primer used to generate fragment 119 (FIG. 6).

SEQ ID NO: 60 sets out the nucleotide sequence of the primer used to generate fragment 118 (FIG. 6).

SEQ ID NO: 61 sets out the nucleotide sequence of the primer used to generate fragment 118 (FIG. 6).

SEQ ID NO: 62 sets out the nucleotide sequence of fragment 118 (FIG. 6) which includes coding sequence for fumarate reductase from *Trypanosoma brucei* (FRDg) codon pair optimized for expression in *S. cerevisiae*.

SEQ ID NO: 63 sets out the nucleotide sequence of the primer used to generate fragment 124 (FIG. 7).

SEQ ID NO: 64 sets out the nucleotide sequence of fragment 121 (FIG. 7) which includes coding sequence for *S. cerevisiae* MDH3 mutant MUT_014 codon pair optimized for expression in *S. cerevisiae*.

SEQ ID NO: 65 sets out the nucleotide sequence of fragment 122 (FIG. 7) which includes coding sequence for *S. cerevisiae* MDH3 mutant MUT_015 codon pair optimized for expression in *S. cerevisiae*.

SEQ ID NO: 66 sets out the nucleotide sequence of fragment 123 (FIG. 7) which includes coding sequence for *S. cerevisiae* MDH3 mutant MUT_034 codon pair optimized for expression in *S. cerevisiae*.

SEQ ID NO: 67 sets out the amino acid sequence of fumarase from *Arabidopsis thaliana*.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The reductive TCA pathway is one of the primary pathways by which a microorganism can produce dicarboxylic acids. In recent years, it has proven to be the best economic option for the microbial production of dicarboxylic acids, e.g. succinic acid. The reductive TCA pathway includes two reactions which require the consumption of reducing power; i.e. the malate dehydrogenase reaction (reduction of oxaloacetate to malate) and the fumarate reductase reaction (reduction of fumarate to succinate).

Malate dehydrogenase (MDH) catalyzes the reversible conversion of malate to oxaloacetate using NAD or NADP as the cofactor (also collectively referred as NAD(P)). MDH is a rather ubiquitous enzyme and plays crucial roles in many metabolic pathways, including the tricarboxylic acid cycle, amino acid synthesis, gluconeogenesis, maintenance of the oxidation/reduction balance and metabolic stress.

MDHs can be divided into NAD(H)-dependent MDHs (NAD-MDH) (EC 1.1.1.37) and NADP(H)-dependent MDHs (NADP-MDH) (EC 1.1.1.82), according to their preference for cofactors. Most bacterial and archaeal MDHs are NAD-MDHs. Eukaryotic MDH isoforms are all NAD-MDHs, including mitochondrial MDHs, cytosolic MDHs, glyoxysomal MDHs, and peroxisomal MDHs, except for chloroplastic NADP-MDHs, which are required for the transfer of reducing equivalents from chloroplast stroma to cytosol. In the yeast *Saccharomyces cerevisiae*, three endogenous isoenzymes of malate dehydrogeneases have been identified, namely MDH1, MDH2 and MDH3. They were located in the mitochondria (MDH1), the cytosol (MDH2) and the peroxisome (MDH3) and were all characterized to be NAD(H)-dependent MDHs (EC 1.1.1.37).

The study of NAD(P)-binding domains in the malate dehydrogenase enzyme family revealed a conserved βB-αC motif of the Rossmann fold. The ability of the dehydrogenases to discriminate against NADP(H) lies in the amino acid sequence of this βB-αC motif, which has been predicted to be a principal determinant for cofactor specificity. For example, in the *S. cerevisiae* peroxisomal NAD-MDH (MDH3), the NAD-binding motif includes amino acid residues 34 to 40 which were found important for cofactor binding and specificity.

In the context of the present invention, it has been surprisingly found that a set of specific mutations in the conserved NAD-binding motif of a polypeptide having MDH activity confers an increased production of a dicarboxylic acid when (over)expressed in a recombinant host cell capable of the production of said dicarboxylic acid. That is to say, (over)expression of said mutant polypeptide having MDH activity in a recombinant host cell typically leads to increased production of a dicarboxylic acid as compared to a recombinant host cell which (over)expresses a reference MDH polypeptide; the "reference MDH polypeptide" being typically a NAD-MDH (EC 1.1.1.37). Concomitantly, it has been shown that said mutant polypeptide having at least one mutation in the conserved NAD-binding motif has an increase in the NADP(H)-relative to NAD(H)-dependent activity as compared to that of said reference MDH polypeptide. Surprisingly, the inventors of the present invention have further shown that the NADP(H)-dependent activity does not have to be higher than the NAD(H)-dependent activity to obtain an increase in dicarboxylic acid production.

It is therefore an object of the present invention to provide a recombinant host cell which is capable of producing a dicarboxylic acid and which comprises a mutant polypeptide having malate dehydrogenase (MDH) activity.

In one embodiment, the mutant polypeptide having malate dehydrogenase activity comprises an amino acid sequence which, when aligned with the malate dehydrogenase comprising the sequence set out in SEQ ID NO: 39, comprises one mutation of an amino acid residue corresponding to amino acid 34 in SEQ ID NO: 39. In other words, said mutant polypeptide comprises one mutation of an amino acid residue occurring at a position corresponding to 34 in SEQ ID NO: 39.

In a preferred embodiment of the invention, the mutation of the amino acid corresponding to amino acid 34 (as defined with reference to SEQ ID NO: 39) will be a substitution.

More preferably, the substitution of the amino acid corresponding to amino acid 34 (as defined with reference to SEQ ID NO: 39) will typically be to a small amino acid. Suitable small amino acids include threonine (T), serine (S), glycine (G), alanine (A) and proline (P). Preferred small amino acids are glycine (G) and serine (S).

In the context of the present invention, a "recombinant host cell" or a "genetically modified host cell" is a host cell into which has been introduced, by means of recombinant DNA techniques, a nucleic acid, a nucleic acid construct or a vector comprising a nucleic acid sequence encoding a mutant polypeptide having malate dehydrogenase activity.

Herein, a "mutant polypeptide having malate dehydrogenase (MDH) activity" may be referred to as a "mutant malate dehydrogenase", "MDH mutant", "MDH mutant polypeptide", "mutant", "mutant polypeptide" or the like.

Herein, the "malate dehydrogenase activity" is the activity converting oxaloacetic acid to malic acid:

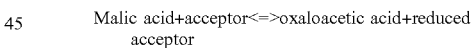
Malic acid+acceptor<=>oxaloacetic acid+reduced acceptor

The term "polypeptide" is used herein for chains containing more than about seven amino acid residues. All polypeptide sequences herein are written from left to right and in the direction from amino terminus to carboxy terminus. The one-letter code of amino acids used herein is commonly known in the art and can be found in Sambrook et al. (Molecular Cloning: A Laboratory Manual, 3rd edition, *Cold Spring Harbor Laboratory Press*, Cold Spring Harbor Laboratory, N Y, 2001).

In the context of the present invention, a "mutant" polypeptide is defined as a polypeptide which was obtained by introduction of one or more mutations. Said mutations may be selected from the group of substitutions, additions and deletions. The term "substitution" herein means the replacement of an amino acid residue in the polypeptide sequence with another one. A "mutant" polypeptide, a "mutated" polypeptide and a "genetically engineered" polypeptide have the same meaning and are used interchangeably.

Herein, a "corresponding position" refers to the vertical column in an amino acid sequence alignment between SEQ ID NO: 39 and sequences homologous to SEQ ID NO: 39 corresponding to a specific position in SEQ ID NO:39 and showing the amino acids that occur at this position in the other aligned homologues.

In the context of the invention, a "corresponding mutation" refers to a mutation of an amino acid residue occurring at a "corresponding position" in SEQ ID NO: 39. For example, a "corresponding substitution" refers to a substitution of an amino acid residue occurring at a "corresponding position" in SEQ ID NO: 39 with another amino acid residue.

In some further embodiments, the mutant polypeptide having malate dehydrogenase activity may further comprise one or more additional mutations corresponding to any of amino acids 35, 36, 37, 38, 39 and/or 40 in SEQ ID NO: 39. Said mutations will typically be selected from the group of substitutions, additions and deletions. More preferably, the one or more additional mutations will be a substitution.

The substitution of the amino acid corresponding to amino acid 35 (as defined with reference to SEQ ID NO: 39) will typically be to a small amino acid. Suitable small amino acids include threonine (T), serine (S), glycine (G), alanine (A) and proline (P). Alternatively, the substitution of the amino acid corresponding to amino acid 35 (as defined with reference to SEQ ID NO: 39) will be to a hydrophobic amino acid, such as isoleucine (I). A preferred substitution of the amino acid corresponding to amino acid 35 (as defined with reference to SEQ ID NO: 39) will be to serine (S) or isoleucine (I).

The substitution of the amino acid corresponding to amino acid 36 (as defined with reference to SEQ ID NO: 39) will typically be to a polar amino acid. Suitable polar amino acids include arginine (R), glutamine (Q), Glutamic acid (E) and serine (S). Alternatively, the substitution of the amino acid corresponding to amino acid 36 (as defined with reference to SEQ ID NO: 39) will be to a small amino acid, such as alanine (A) or proline (P). A preferred substitution of the amino acid corresponding to amino acid 36 (as defined with reference to SEQ ID NO: 39) will be to arginine (R), glutamine (Q), glutamic acid (E), serine (S), alanine (A) or proline (P).

The substitution of the amino acid corresponding to amino acid 37 (as defined with reference to SEQ ID NO: 39) will typically be to a small amino acid. Suitable small amino acids include glycine (G), asparagine (N), and alanine (A). Alternatively, the substitution of the amino acid corresponding to amino acid 37 (as defined with reference to SEQ ID NO: 39) will be to a polar amino acid, such as arginine (R) or glutamine (Q). A preferred substitution of the amino acid corresponding to amino acid 37 (as defined with reference to SEQ ID NO: 39) will be to (G), asparagine (N), alanine (A), alanine arginine (R) or glutamine (Q).

The substitution of the amino acid corresponding to amino acid 38 (as defined with reference to SEQ ID NO: 39) will typically be to a small amino acid. Suitable small amino acids include valine (V), threonine (T), serine (S), glycine (G), alanine (A) and proline (P). A preferred substitution of the amino acid corresponding to amino acid 38 (as defined with reference to SEQ ID NO: 39) will be to alanine (A), valine (V), threonine (T) or serine (S).

The substitution of the amino acid corresponding to amino acid 39 (as defined with reference to SEQ ID NO: 39) will typically be to a small amino acid. A suitable small amino acid includes proline (P). Alternatively, the substitution of the amino acid corresponding to amino acid 39 (as defined with reference to SEQ ID NO: 39) will be to a hydrophobic amino acid, such as lysine (K), phenylalanine (F) or leucine (L). Alternatively, the substitution of the amino acid corresponding to amino acid 39 (as defined with reference to SEQ ID NO: 39) will be to a polar amino acid, such as glutamic acid (E). A preferred substitution of the amino acid corresponding to amino acid 39 (as defined with reference to SEQ ID NO: 39) will be to glutamic acid (E), lysine (K), phenylalanine (F), leucine (L) or proline (P).

The substitution of the amino acid corresponding to amino acid 40 (as defined with reference to SEQ ID NO: 39) will typically be to a small amino acid. Suitable small amino acids include glycine (G). Alternatively, the substitution of the amino acid corresponding to amino acid 40 (as defined with reference to SEQ ID NO: 39) will be to a polar amino acid, such as glutamine (Q). A preferred substitution of the amino acid corresponding to amino acid 40 (as defined with reference to SEQ ID NO: 39) will be to glycine (G) or glutamine (Q).

The various types of amino acids above are classified with reference to, for example, Betts and Russell, In Bioinformatics for Geneticists, Barnes and Gray eds, Wiley 2003.

In more detail, in the context of the invention, a mutant polypeptide having malate dehydrogenase activity will comprise G or S at position 34 as defined with reference to SEQ ID NO: 39;

and, optionally

I or S at position 35 as defined with reference to SEQ ID NO: 39; and/or

R, Q, A, E, P or S at position 36 as defined with reference to SEQ ID NO: 39; and/or A, N, G, R or Q at position 37 as defined with reference to SEQ ID NO: 39; and/or A, V, T or S at position 38 as defined with reference to SEQ ID NO: 39; and/or E, K, P, F or L at position 39 as defined with reference to SEQ ID NO: 39; and/or G or Q at position 40 as defined with reference to SEQ ID NO: 39.

In one specific embodiment, a mutant polypeptide having malate dehydrogenase activity will comprise a small amino acid at position 34 (as defined with reference to SEQ ID NO: 39) and a small or polar amino acid at position 36 (as defined with reference to SEQ ID NO: 39). In said embodiment, a preferred small amino acid at position 34 may be selected from G or S. In said embodiment, a preferred small or polar amino acid at position 36 may be selected from R, Q, A, E, P or S. Optionally, in said embodiment, the mutant polypeptide will comprise I or S at position 35 as defined with reference to SEQ ID NO: 39; and/or A, N, G, R or Q at position 37 as defined with reference to SEQ ID NO: 39; and/or A, V, T or S at position 38 as defined with reference to SEQ ID NO: 39; and/or E, K, P, F or L at position 39 as defined with reference to SEQ ID NO: 39; and/or G or Q at position 40 as defined with reference to SEQ ID NO: 39.

The mutant polypeptide having MDH activity may furthermore comprises additional mutations other than the seven positions defined above, for example, one or more additional substitutions, additions or deletions.

The mutant polypeptide having MDH activity may comprise a combination of different types of modification of this sort. The mutant polypeptide having MDH activity may comprise one, two, three, four, least 5, at least 10, at least 15, at least 20, at least 25, at least 30 or more such modifications (which may all be of the same type or may be different types of modification). Typically, the additional modifications may be substitutions.

In yet further embodiments, the mutant polypeptide having malate dehydrogenase activity is as defined with reference to Table 1 (Example 4) and wherein the amino acid residue corresponding to amino acid 34 in SEQ ID NO: 39 is selected from glycine (G) or serine (S). That is to say, the mutant polypeptide may comprise any combination of substitutions as set out in Table 1 as compared to a suitable reference sequence such as that set out in SEQ ID NO: 39, and wherein the amino acid residue corresponding to amino acid 34 in SEQ ID NO: 39 is selected from glycine (G) or serine (5).

Typically, then the mutant polypeptide may comprise the sequence of SEQ ID NO: 39 with one substitution at position 34, and optionally one or more substitutions at 35, 36, 37, 38, 39 and/or 40. That is to say, the mutant polypeptide will have an amino acid other than aspartate at position 34 and optionally an amino acid other than isoleucine at position 35 and/or an amino acid other than arginine at position 36 and/or an amino acid other than alanine at position 37, and/or an amino acid other than alanine at position 38, and/or an amino acid other than glutamate at position 39, and/or an amino acid other than glycine at position 40.

Also, typically, the mutant polypeptide may comprise the sequence of SEQ ID NO: 39 with one substitution at position 34, one substitution at position 36, and optionally one or more substitutions at 35, 37, 38, 39 and/or 40. That is to say, the mutant polypeptide will have an amino acid other than aspartate at position 34, an amino acid other than arginine at position 36, and optionally an amino acid other than isoleucine at position 35 and/or an amino acid other than alanine at position 37, and/or an amino acid other than alanine at position 38, and/or an amino acid other than glutamate at position 39, and/or an amino acid other than glycine at position 40.

In a separate embodiment of the present invention, the mutant polypeptide having malate dehydrogenase activity has an increase in the NADP(H)-relative to NAD(H)-dependent activity as compared to that of a reference MDH polypeptide. In said embodiment, said mutant polypeptide may be a mutant polypeptide comprising an amino acid sequence which, when aligned with the malate dehydrogenase comprising the sequence set out in SEQ ID NO: 39, comprises one mutation (e.g. one substitution) of an amino acid residue corresponding to amino acid 34 in SEQ ID NO: 39. Further embodiments with regard to the amino acid sequence of said mutant polypeptide are as described herein above.

In the context of the invention, a reference polypeptide having malate dehydrogenase activity, also called a "reference MDH polypeptide", may be NAD-MDH (EC 1.1.1.37). A reference polypeptide having malate dehydrogenase activity may be a malate dehydrogenase from a microbial source, such as a yeast (e.g. *Saccharomyces cerevisiae*). A malate dehydrogenase having the amino acid sequence set out in SEQ ID NO: 39 may be a suitable reference polypeptide having MDH activity.

The expression "increase in NADP(H)-relative to NAD (H)-dependent activity" herein typically refers to the property of a mutant polypeptide to show an increase in NADP (H)-relative to NAD(H)-dependent activity in comparison to that of a reference MDH polypeptide, for example in comparison to SEQ ID NO: 39. That is to say a mutant polypeptide may show an increase in the ratio of NADP(H)- to NAD(H)-dependent activity in comparison to that of a reference polypeptide. In Example 5, the ratio is also referred as the "NADPH:NADH specificity ratio".

In the context of the present invention, the terms "NADP (H)-dependent activity" and "NADP(H)-specific activity" have the same meaning herein and are used interchangeably. Same applies for the terms "NAD(H)-dependent activity" and "NAD(H)-specific activity".

The term "NADP(H)-dependent activity" herein refers to the property of an enzyme to use NADP(H) as the redox cofactor. The NADP(H)-dependent activity of the enzyme may be determined by an enzyme activity assay such as described in Example 5.

The term "NAD(H)-dependent activity" herein refers to the property of an enzyme to use NAD(H) as the redox cofactor. The NAD(H)-dependent activity of the enzyme may be determined by an enzyme activity assay such described in Example 5.

An increased value of the average NADPH:NADH specificity ratio may indicate, for example, a reduced NAD(H)-dependent activity, an increased NADP(H)-dependent activity or a combination of the two. In some cases, an increased value of said ratio may be obtained with a MDH mutant having a similar or increased NAD(H)-dependent activity in comparison to a reference MDH. In the latter cases, it may be that the MDH mutant displays both increased NAD(H)- and NADP(H)-dependent activities.

The mutant MDH polypeptide will typically have modified MDH activity in terms of modified cofactor dependence. This NAD(H)- or NADP(H)-dependent activity may be modified independent from each other, for example decreased, by at least 10%, at least 20%, at least 30%, at least 40%, at least 50%, at least 60%, at least 70%, at least 80%, at least 90%, at least 95% or at least 99%. Alternatively, the property may be increased by at least 10%, at least 25%, at least 50%, at least 70%, at least 100%, at least, 200%, at least 500%, at least 700%, at least 1000%, at least 3000%, at least 5000%, or at least 6000%.

In one specific embodiment, the NAD(H)- and NADP (H)-dependent activities of the mutant MDH polypeptide are both increased. The NAD(H)-dependent activity of said mutant MDH polypeptide is increased by at least 10%, at least 25%, at least 50%, at least 70%, at least 100%, at least, 200%, or at least 300%. The NADP(H)-dependent activity of said mutant MDH polypeptide is increased by at least 10%, at least 25%, at least 50%, at least 70%, at least 100%, at least, 200%, at least 500%, at least 700%, at least 1000%, at least 3000%, at least 5000%, or at least 6000%.

In another embodiment, the NAD(H)-dependent activity of the mutant MDH polypeptide is about the same or decreased by at most 5%, at most 10%, at most 20%, at most 30%, at most 40%, at most 50%, at most 60%, at most 70%, at most 80% and the NADP(H)-dependent activity of said mutant MDH polypeptide is increased by at least 10%, at least 25%, at least 50%, at least 70%, at least 100%, at least, 200%, at least 500%, at least 700%, at least 1000%, at least 3000%, at least 5000%, or at least 6000%.

In another embodiment, the NADPH:NADH specificity ratio of the mutant MDH polypeptide is increased by at least 10%, at least 50%, at least 100%, at least, 200%, at least 500%, at least 1000%, at least 3000%, at least 5000%, at least 7000%, or at least 8000%.

The percentage decrease or increase in this context represents the percentage decrease or increase in comparison to the reference MDH polypeptide, for example that of SEQ ID NO: 39. It is well known to the skilled person how such percentage changes may be measured—it is a comparison of the activity, for example NAD(H)- or NADP(H)-dependent activity, of the reference MDH and the mutant MDH measured as set out in the Examples.

In the context of the present invention, the MDH mutant polypeptide as described herein above may be a mutant NAD(P)-malate dehydrogenase, such as a mutant mitochondrial NAD-MDH, a mutant cytosolic NAD-MDH, a mutant glyoxysomal NAD-MDH, a mutant peroxisomal NAD-MDH, or a mutant chloroplastic NADP-MDH. That is to say, the mutant polypeptide having malate dehydrogenase activity may be obtained by introduction of one or more mutations in a NAD(P)-malate dehydrogenase, such as a mitochondrial NAD-MDH, cytosolic NAD-MDH, glyoxysomal NAD-MDH, peroxisomal NAD-MDH, or a chloroplastic NADP-MDH (the latter being referred as template MDH polypeptides for introducing said one or more mutations). Preferably, the mutant polypeptide having malate dehydrogenase activity is a mutant NAD(H)-malate dehydrogenase (EC 1.1.1.37). More preferably, the mutant polypeptide having malate dehydrogenase activity is a mutant peroxisomal NAD(H)-malate dehydrogenase. Even more preferably, the mutant polypeptide having malate dehydrogenase activity is a mutant NAD(H)-malate dehydrogenase from a yeast or a fungus. Even more preferably, the mutant polypeptide having malate dehydrogenase activity is a mutant NAD(H)-malate dehydrogenase from a yeast or fungus, such as *S. cerevisiae, Torulaspora delbrueckii, Zygosaccharomyces bailiff, Naumovozyma casteffii, Naumovozyma dairenensis, Lachancea lanzarotensis, Zygosaccharomyces rouxii, Kazachstania africana, Candida tropicalis, Kluyveromyces marxianus, Scheffersomyces stipites, Talaromyces mameffei, Rasamsonia emersonii, Aspergillus niger*, or *Trametes versicolor*. The following Uniprot database codes refer to suitable yeast and fungal template MDH polypeptides (http://www.uniprot.org): E7NGH7, G8ZXS3, G0V668, W0VUI8, G0WB63, A0A0W0D4X6, A0A0C7MME9, C5DQ42, C5D145, H2AWW6, A0A090C493, J7R0C8, Q6CJP3, Q759M4, I2H037, C5M546, A7TL95, A0A0L0P3G3, Q6BM17, S8AW17, V5FMV2, A3LW84, A0A109UZS1, G8BVW8, G8BJ12, M3HPK4, A0A093UW53, B8MTP0, A0A0F4YPR0, C8V0H6, W6QNU3, A5DZ33, U1GAT6, G3B7S5, C4JP17, A0A0F8UZY9, Q4WDM0, A0A093UPX3, B8ND04, A0A0M9VRI4, G7XZ98, Q5A5S6, M7S9E4, E4UYX5, A5DE02, A0A0J7B1J5, A0A017SKI1, G8Y7A1, A0A0G2EFQ2, R7S165, I1RFM4, R1EVC8, U4L6K9, A0A0L0P507, W7HM94, A5DGY9, F2QY33, A0A0G2JA24, UPI000462180C, C7Z9W6, E5AAQ2, B2VVR8, A0A0H2RCV1, A8Q524, A0A0E9N879, N1JA02, A0A0D1ZEE3, J5T1X5, W6MY07, C4Y826, G3AJA2, G9N6G5, AOAOK8L6L9, A3GH28, A8P7W6, K5W0T4, G1XT67, A0A0B7K175, B8MTP5, A0A0D1ZAS7, A0A0C3BQC4, K5Y2Q9, A0A0C3DSW4, A0A068S518, W2RPL2, A0A0H5C453, A0A074WKG5, G8JRX4, A0A0U1M134, H6C0V9, A0A0H5BZ30, M2UXR7, A0A0C9YJV6, A0A0C3S6T1, W1Q K02, A0A0C2YFC4, A0A061AJ54, A0A086T183, W2RVT1, UPI0004623914, A0A0C9X7U1, UPI0001F26169, G7E054, A0A0C2S9T3, A0A067NIX1, L8FPM0, G3ALW4, A0A0D0AYX2, G0VJG3, A0A0D2NGY0, C1GLB8, W9X415, A0A0D0CDE8, S7Q8G0, A0A0C9TB51, R7YP89, A0A0C2W4H8, UPI000455FA04, A0A067NL73, A0A067STP4, W9VWVP5, A0A0D7A9T7, A0A0D6R2E1, M2YLX9, G0W7D4, N1QJ61, G4TRY5, FOXJ10, A0A063BQQ6, A0A061HBX5, A0A0A1PCT2, M1WIC4, A8QAQ2, A0A0C3N631, F2QTL7, A0A060S7U3, A0A0L0HTQ9, Q0CKY1, A0A0C2ZJ90, K5W527, I4Y5C3, R7YXZ2, F9XI12, A0A061J968, F9XL74, A0A0D0BEW9, A0A0C9WB72, F7WA21, A8NJ67, M2P8M6, W4KHW3, A0A0L1I2T4, UPI0004449A9D, P83778, C4Y9Q7, A0A0D7BHV7, A0A068RWX9, M2YWQ3, A0A137QV51, A0A0D0B6C2, I1BQQ7, S3DA07, Q4DXL5, G8Y022, A0A0C9W9B3, A0A0L6WJ49, A0A0L9SL52, D5GA85, A0A0N1J4Z6, J7S1G2, A0A0F4X5C6, Q6CIK3, A0A067QNN0, Q0UGT7, F8ND69, U5HIM0, J3NKC7, A0A061ATZ7, A5DSY0, Q9Y750, UPI0004F4119A, A0A086TL69, A0A0J0XSS4, UPI0003F496E1, UPI000455F0EA, S7RXX1, A0A067NAG9, A0A0B7N3M5, E6ZKH0, C8V1V3, A7UFI6, T5AEM1, A0A072PGA9, A0A094EKH6, S8ADX4, G8C073, Q6BXI8, G2R9I6 and U9TUL6. Even more preferably, the mutant polypeptide having malate dehydrogenase activity is a mutant *S. cerevisiae* peroxisomal NAD-MDH (MDH3).

Additionally, in the recombinant host cell of the invention, the mutant polypeptide having malate dehydrogenase activity may be a mutant of a homologous or heterologous NAD(P)-malate dehydrogenase. In a preferred embodiment, the MDH mutant is a mutant of a homologous NAD(P)-malate dehydrogenase. More preferably, the MDH mutant is a mutant of a homologous NAD(H)-malate dehydrogenase (EC 1.1.1.37). More preferably, the mutant polypeptide having malate dehydrogenase activity is a mutant of a homologous peroxisomal NAD(H)-malate dehydrogenase.

In this context, the term "homologous" or "endogenous" when used to indicate the relation between a given (recombinant) nucleic acid or polypeptide molecule and a given host organism or host cell, is understood to mean that in nature the nucleic acid or polypeptide molecule is produced by a host cell or organism of the same species, preferably of the same variety or strain.

The term "heterologous" as used herein refers to nucleic acid or amino acid sequences not naturally occurring in a host cell. In other words, the nucleic acid or amino acid sequence is not identical to that naturally found in the host cell.

Preferably, in a recombinant host cell of the present invention, the nucleic sequence encoding said mutant polypeptide having malate dehydrogenase activity is expressed in the cytosol and the mutant polypeptide having malate dehydrogenase activity is active in the cytosol. In some instances, cytosolic expression may be obtained by deletion of a peroxisomal or mitochondrial targeting signal. The presence of a peroxisomal or mitochondrial targeting signal may for instance be determined by the method disclosed by Schluter et al., Nucleid Acid Research 2007, 35, D815-D822. When the MDH mutant is a mutant *S. cerevisiae* peroxisomal NAD-MDH (e.g. a mutant MDH3), its C-terminal SKL is preferably deleted such that it is active in the cytosol.

Typically, the mutant polypeptide having malate dehydrogenase activity may have at least about 40%, 50%, 60%, 70%, 80% sequence identity with a reference MDH polypeptide, such as the MDH of SEQ ID NO: 53 or SEQ ID NO: 39, for example at least 85% sequence identity with a reference MDH polypeptide, such as at least about 90% sequence identity with a reference MDH polypeptide, at least 95% sequence identity with a reference MDH polypeptide, at least 98% sequence identity with a reference MDH polypeptide or at least 99% sequence identity with a reference MDH polypeptide.

It has been surprisingly found that said mutant MDH polypeptide as described herein above confers an increase in the production of a dicarboxylic acid in a recombinant host cell when said mutant is (over)expressed in said recombinant host cell as compared to the production level of an equivalent recombinant host cell which (over)expresses a reference polypeptide having MDH activity; the "reference MDH polypeptide" being typically a NAD-MDH (EC 1.1.1.37), for example a malate dehydrogenase having an amino acid sequence set out in SEQ ID NO: 39.

Accordingly, there is thus provided a recombinant host cell which is capable of producing or produces a dicarboxylic acid and which comprises a nucleic acid sequence encoding a mutant polypeptide having malate dehydrogenase activity as described herein above.

A recombinant host cell of the invention is capable of producing or produces a dicarboxylic acid, such as malic acid, fumaric acid and/or succinic acid.

The terms "dicarboxylic acid" and "dicarboxylate", such as "succinic acid" and "succinate", have the same meaning herein and are used interchangeably, the first being the hydrogenated form of the latter.

Typically, the recombinant host cell of the invention will produce an increased amount of a dicarboxylic acid in comparison to a recombinant host cell expressing a reference MDH polypeptide, for example that of SEQ ID NO: 39. The production of a dicarboxylic acid may be increased, by at least 5%, 10%, at least 20%, at least 30%, at least 40% at least 50%, at least 60%, at least 70%, at least 80%, at least 90%, at least 95%, or at least 100% or more. Production level may be expressed in terms of g/L, so an increase in the production level of a dicarboxylic acid will be evident by higher level of production in terms of g/L.

The recombinant host cell of the invention or a parent of said host cell may be any type of host cell. Accordingly, both prokaryotic and eukaryotic cells are included. Host cells may also include, but are not limited to, mammalian cell lines such as CHO, VERO, BHK, HeLa, COS, MDCK, 293, 3T3, WI38, and choroid plexus cell lines.

A suitable host cell of the invention may be a prokaryotic cell. Preferably, the prokaryotic cell is a bacterial cell. The term "bacterial cell" includes both Gram-negative and Gram-positive microorganisms.

Suitable bacteria may be selected from e.g. *Escherichia, Actinobacillus, Anabaena, Caulobactert, Gluconobacter, Mannheimia, Basfia, Rhodobacter, Pseudomonas, Paracoccus, Bacillus, Brevibacterium, Corynebacterium, Rhizobium* (*Sinorhizobium*), *Flavobacterium, Klebsiella, Enterobacter, Lactobacillus, Lactococcus, Methylobacterium, Staphylococcus* or Actinomycetes such as *Streptomyces* and *Actinoplanes* species. Preferably, the bacterial cell is selected from the group consisting of *Bacillus subtilis, B. amyloliquefaciens, B. licheniformis, B. puntis, B. megaterium, B. halodurans, B. pumilus, Actinobacillus succinogenes, Gluconobacter oxydans, Caulobacter crescentus* CB 15, *Methylobacterium extorquens, Rhodobacter sphaeroides, Pseudomonas zeaxanthinifaciens, Pseudomonas putida, Pseudomonas fluorescens, Paracoccus denitrificans, Escherichia coli, Corynebacterium glutamicum, Mannheimia succinoproducens, Basfia succinoproducens, Staphylococcus carnosus, Streptomyces lividans, Streptomyces clavuligerus, Sinorhizobium melioti* and *Rhizobium radiobacter.*

A host cell according to the invention may be a eukaryotic host cell. Preferably, the eukaryotic cell is a mammalian, insect, plant, fungal, or algal cell. More preferably, the eukaryotic cell is a fungal cell. A suitable fungal cell may for instance belong to genera *Saccharomyces, Schizosaccharomyces, Aspergillus, Penicillium, Pichia, Kluyveromyces, Yarrowia, Candida, Hansenula, Humicola, Pichia, Issatchenkia, Kloeckera, Schwanniomyces, Torulaspora, Trichosporon, Brettanomyces, Rhizopus, Zygosaccharomyces, Pachysolen* or *Yamadazyma*. A fungal cell may for instance belong to a species of *Saccharomyces cerevisiae, S. uvarum, S. bayanus S. pastorianus, S. carlsbergensis, Aspergillus niger, Penicillium chrysogenum, Pichia stipidis, P. pastoris, Kluyveromyces marxianus, K. lactis, K. thermotolerans, Yarrowia lipolytica, Candida sonorensis, C. revkaufi, C. pulcherrima, C. tropicalis, C. utilis, C. kruisei, C. glabrata, Hansenula polymorpha, Issatchenkia orientalis, Torulaspora delbrueckii, Brettanomyces bruxellensis, Rhizopus oryzae* or *Zygosaccharomyces bailii*. In one embodiment, a fungal cell of the present invention is a yeast, for instance belonging to a *Saccharomyces* sp., such as a *Saccharomyces cerevisiae.*

Examples of specific host yeast cells include *C. sonorensis, K. marxianus, K. thermotolerans, C. methanesorbosa, Saccharomyces bulderi* (*S. bulden*), *P. kudriavzevii, I. orientalis, C. lambica, C. sorboxylosa, C. zemplinina, C. geochares, P. membranifaciens, Z. kombuchaensis, C. sorbosivorans, C. vanderwaltii, C. sorbophila, Z. bisporus, Z. lentus, Saccharomyces bayanus* (*S. bayanus*), *D. castellii, C, boidinii, C. etchellsii, K. lactis, P. jadinii, P. anomala, Saccharomyces cerevisiae* (*S. cerevisiae*), *Pichia galeiformis, Pichia* sp. YB-4149 (NRRL designation), *Candida ethanolica, P. deserticola, P. membranifaciens, P. fermentans* and *Saccharomycopsis crataegensis* (*S. crataegensis*). Suitable strains of *K. marxianus* and *C. sonorensis* include those described in WO 00/71738 A1, WO 02/42471 A2, WO 03/049525 A2, WO 03/102152 A2 and WO 03/102201A2. Suitable strains of *I. orientalis* are ATCC strain 32196 and ATCC strain PTA-6648. In the invention, the host cell may be a Crabtree negative as a wild-type strain. The Crabtree effect is defined as the occurrence of fermentative metabolism under aerobic conditions due to the inhibition of oxygen consumption by a microorganism when cultured at high specific growth rates (long-term effect) or in the presence of high concentrations of glucose (short-term effect). Crabtree negative phenotypes do not exhibit this effect, and are thus able to consume oxygen even in the presence of high concentrations of glucose or at high growth rates.

The eukaryotic cell may be a filamentous fungal cell. Filamentous fungi include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocaffimastix, Neurospora, Paecilomyces, Penicillium, Piromyces, Phanerochaete Podospora, Pycnoporus, Rhizopus, Schizophyllum, Sordaria, Talaromyces, Rasamsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g.

*Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Thielavia terrestris* NRRL8126, *Talaromyces emersonii* CBS 124.902, *Rasamsonia emersonii* CBS393.64, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains.

A more preferred host cell belongs to the genus *Aspergillus*, more preferably the host cell belongs to the species *Aspergillus niger*. When the host cell according to the invention is an *Aspergillus niger* host cell, the host cell preferably is CBS 513.88, CBS124.903 or a derivative thereof.

In a preferred embodiment, a host cell according to the invention is a yeast cell selected from the group consisting of *Candida, Hansenula, Issatchenkia, Kluyveromyces, Pichia, Saccharomyces, Schizosaccharomyces*, or *Yarrowia* strains, or a filamentous fungal cell selected from the group consisting of filamentous fungal cells belong to a species of *Acremonium, Aspergillus, Chrysosporium, Myceliophthora, Penicillium, Talaromyces, Rasamsonia, Thielavia, Fusarium* or *Trichoderma*.

A host cell of the invention may be any wild type strain producing a dicarboxylic acid. Furthermore, a suitable host cell may be a cell which has been obtained and/or improved by subjecting a parental or wild type cell of interest to a classical mutagenic treatment or to recombinant nucleic acid transformation. Thus, a suitable host cell may already be capable of producing the dicarboxylic acid. However, the cell may also be provided with a homologous or heterologous expression construct that encodes one or more polypeptides involved in the production of the dicarboxylic acid.

Accordingly, in some embodiments, a recombinant host cell of the invention may comprise a MDH mutant polypeptide and an active reductive tricarboxylic acid (TCA) pathway from phosphoenolpyruvate or pyruvate to succinate.

Accordingly, in addition to a nucleic acid encoding a MDH mutant polypeptide, a host cell of the invention may comprise a nucleotide sequence comprising sequence encoding one or more of a pyruvate carboxylase, a phosphoenolpyruvate carboxykinase, a phosphoenolpyruvate carboxylase, a malate dehydrogenase, a fumarase, an isocitrate lyase, a malate synthase, a fumarate reductase and/or a dicarboxylic acid transporter. Preferably, one or more such enzymes are (over)expressed and active in the cytosol.

Thus, a recombinant host cell of the invention may overexpress a suitable homologous or heterologous nucleotide sequence that encodes a endogenous and/or heterologous enzyme that catalyzes a reaction in the cell resulting in an increased flux towards a dicarboxylic acid such malic acid, fumaric acid and/or succinic acid.

A recombinant host cell of the invention may overexpress an endogenous or heterologous nucleic acid sequence as described herein below.

A recombinant host cell of the invention may comprise a genetic modification with a pyruvate carboxylase (PYC), that catalyses the reaction from pyruvate to oxaloacetate (EC 6.4.1.1). The pyruvate carboxylase may for instance be active in the cytosol upon expression of the gene. For instance, the host cell overexpresses a pyruvate carboxylase, for instance an endogenous or homologous pyruvate carboxylase is overexpressed. The recombinant fungal host cell according to the present invention may be genetically modified with a pyruvate carboxylase which has at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 46.

Preferably, the recombinant host cell expresses a nucleotide sequence encoding a phosphoenolpyruvate (PEP) carboxykinase in the cytosol. Preferably a nucleotide sequence encoding a PEP carboxykinase is overexpressed. The PEP carboxykinase (EC 4.1.1.49) preferably is a heterologous enzyme, preferably derived from bacteria, more preferably the enzyme having PEP carboxykinase activity is derived from *Escherichia coli, Mannheimia* sp., *Actinobacillus* sp., or *Anaerobiospirillum* sp., more preferably *Mannheimia succiniciproducens*. A gene encoding a PEP carboxykinase may be overexpressed and active in the cytosol of a fungal cell. Preferably, a recombinant fungal cell according to the present invention is genetically modified with a PEP carboxykinase which has at least 70%, preferably at least 75%, 80%, 85%, 90%, 91%, 92%, 93%, 94%, 95%, 96%, 97%, 98%, 99% or 100% sequence identity with amino acid sequence of SEQ ID NO: 47.

Preferably, the recombinant host cell expresses a nucleotide sequence encoding a phosphoenolpyruvate (PEP) carboxylase in the cytosol. Preferably a nucleotide sequence encoding a PEP carboxylase is overexpressed. The PEP carboxylase (EC 4.1.1.31) preferably is a heterologous enzyme, preferably derived from bacteria.

In one embodiment, the recombinant host cell is further genetically modified with a gene encoding a malate dehydrogenase (MDH) active in the cytosol upon expression of the gene. Cytosolic expression may be obtained by deletion of a peroxisomal targeting signal. The malate dehydrogenase may be overexpressed. A cytosolic MDH may be any suitable homologous or heterologous malate dehydrogenase, catalyzing the reaction from oxaloacetate to malate (EC 1.1.1.37), for instance derived from *S. cerevisiae*.

Preferably, the MDH is *S. cerevisiae* MDH3, more preferably one which has a C-terminal SKL deletion such that it is active in the cytosol. Preferably, the recombinant fungal cell according to the present invention comprises a nucleotide sequence encoding a malate dehydrogenase that has at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 39.

In another embodiment, the recombinant host cell of the present disclosure is further genetically modified with a gene encoding a fumarase, that catalyses the reaction from malic acid to fumaric acid (EC 4.2.1.2). A gene encoding fumarase may be derived from any suitable origin, preferably from microbial origin, for instance a yeast such as *Saccharomyces* or a filamentous fungus, such *Rhizopus oryzae*, or a bacterium such a *Escherichia coli*. The host cell of the present disclosure may overexpress a nucleotide sequence encoding a fumarase. The fumarase may be active in the cytosol upon expression of the nucleotide sequence, for instance by deleting a peroxisomal targeting signal. It was found that cytosolic activity of a fumarase resulted in a high productivity of a dicarboxylic acid by a fungal cell.

Preferably, the recombinant host cell of the present invention overexpresses a nucleotide sequence encoding a fumarase that has at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 48, SEQ ID NO: 49 or SEQ ID NO: 67.

In another embodiment, the recombinant host cell is genetically modified with any suitable heterologous or homologous gene encoding a NAD(H)-dependent fumarate reductase, catalyzing the reaction from fumarate to succinate (EC 1.3.1.6). The NAD(H)-dependent fumarate reductase may be a heterologous enzyme, which may be derived from any suitable origin, for instance bacteria, fungi, protozoa or plants. A fungal cell of the present disclosure comprises a heterologous NAD(H)-dependent fumarate reductase, preferably derived from a *Trypanosoma* sp, for instance a *Trypanosoma brucei*. In one embodiment, the NAD(H)-dependent fumarate reductase is expressed and active in the cytosol, for instance by deleting a peroxisomal targeting signal. The host cell may overexpress a gene encoding a NAD(H)-dependent fumarate reductase.

Preferably, the recombinant host cell according to the present invention is genetically modified with a NAD(H)-dependent fumarate reductase, which has at least at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 8. Also preferably, the host cell according to the present invention is genetically modified with a variant polypeptide having fumarate reductase activity as disclosed in WO2015/086839.

In another embodiment, the recombinant host cell of the invention expresses a nucleotide sequence encoding a dicarboxylic acid transporter protein. Preferably the dicarboxylic acid transporter protein is overexpressed. A dicarboxylic acid transporter protein may be any suitable homologous or heterologous protein. Preferably the dicarboxylic acid transporter protein is a heterologous protein. A dicarboxylic acid transporter protein may be derived from any suitable organism, preferably from yeast or fungi such as *Schizosaccharomyces pombe* or *Aspergillus niger*. Preferably, a dicarboxylic acid transporter protein is a dicarboxylic acid transporter/malic acid transporter protein, eg. from *Aspergillus niger* which at least 70%, preferably at least 75%, 80%, 85%, 90%, 91%, 92%, 93%, 94%, 95%, 96%, 97%, 98%, 99% or 100% sequence identity with the amino acid sequence of SEQ ID NO: 50.

The recombinant host cell may further comprise a genetic modification with a gene encoding an isocitrate lyase (EC 4.1.3.1), which may be any suitable heterologous or homologous enzyme. The isocitrate lyase may for instance be obtained from *Kluyveromyces lactis* or *Escherichia coli*.

The recombinant host according to the present invention is genetically modified with a isocitrate lyase which has at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 51.

The recombinant host cell may further comprise a genetic modification with a malate synthase (EC 2.3.3.9). The malate synthase may be overexpressed and/or active in the cytosol, for instance by deletion of a peroxisomal targeting signal. In the event the malate synthase is a *S. cerevisiae* malate synthase, for instance the native malate synthase is altered by the deletion of the SKL carboxy-terminal sequence.

The recombinant host cell of the present invention is genetically modified with a malate synthase which at least 70%, preferably at least 75%, 80%, 85%, 90%, 91%, 92%, 93%, 94%, 95%, 96%, 97%, 98%, 99% or 100% sequence identity with amino acid sequence encoded by the nucleic acid sequence of SEQ ID NO: 52.

In another embodiment, the recombinant host cell of the invention disclosed herein comprises a disruption of a gene a pyruvate decarboxylase (EC 4.1.1.1), catalyzing the reaction from pyruvate to acetaldehyde.

In another embodiment, the recombinant host cell of the invention may comprise a disruption of a gene encoding an enzyme of the ethanol fermentation pathway. A gene encoding an enzyme of an ethanol fermentation pathway, may be pyruvate decarboxylase (EC 4.1.1.1), catalyzing the reaction from pyruvate to acetaldehyde, or alcohol dehydrogenase (EC 1.1.1.1), catalyzing the reaction from acetaldehyde to ethanol. Preferably, a host cell of the invention comprises a disruption of one, two or more genes encoding an alcohol dehydrogenase. In the event the fungal cell is a yeast, e.g. *S. cerevisiae*, the yeast preferably comprises a disruption of one or more alcohol dehydrogenase genes (adh1 adh2, adh3, adh4, adh5, adh6).

Alternatively or in addition, the recombinant host cell of the invention may comprise at least one gene encoding glycerol-3-phosphate dehydrogenase which is not functional. A glycerol-3-phosphate dehydrogenase gene that is not functional is used herein to describe a eukaryotic cell, which comprises a reduced glycerol-3-phosphate dehydrogenase activity, for instance by mutation, disruption, or deletion of the gene encoding glycerol-3-phosphate dehydrogenase, resulting in a decreased formation of glycerol as compared to a wild-type cell. In the event the fungal cell is a yeast, e.g. *S. cerevisiae*, the yeast preferably comprises a disruption of one or more glycerol-3-phosphate dehydrogenase genes (gpd1, gpd2, gut2).

Alternatively or in addition to the above, the recombinant host cell of the invention may comprise at least one gene encoding a mitochondrial external NADH dehydrogenase which is not functional. A mitochondrial external NADH dehydrogenase gene that is not functional is used herein to describe a eukaryotic cell, which comprises a reduced NADH dehydrogenase activity, for instance by mutation, disruption, or deletion of the gene encoding the mitochondrial external NADH dehydrogenase. In the event the fungal cell is a yeast, e.g. *S. cerevisiae*, the yeast preferably comprises a disruption of one or more mitochondrial external NADH dehydrogenase genes (nde1, nde2).

Alternatively or in addition to the above, the recombinant host cell of the invention may comprise at least one gene encoding an aldehyde dehydrogenase which is not functional. An aldehyde dehydrogenase gene that is not functional is used herein to describe a eukaryotic cell, which comprises a reduced aldehyde dehydrogenase activity, for instance by mutation, disruption, or deletion of the gene encoding the aldehyde dehydrogenase. In the event the fungal cell is a yeast, e.g. *S. cerevisiae*, the yeast preferably comprises a disruption of one or more aldehyde dehydrogenase genes (ald2, ald3, ald4, ald5, ald6).

Preferably, the recombinant host cell of the present invention is a recombinant fungal cell. More preferably, the host cell of the present invention is a recombinant yeast cell. Preferred embodiments of the recombinant fungal cell or recombinant yeast cell are as described herein above for the recombinant host cell.

In some embodiments of the invention, the recombinant host cell is a recombinant yeast cell which is capable of producing a dicarboxylic acid as described herein above and which comprises a nucleic acid sequence encoding a mutant polypeptide having malate dehydrogenase activity as detailed herein above. Said MDH mutant may be a mutant of a homologous or heterologous wild-type MDH polypeptide. In a preferred embodiment, said MDH mutant is a mutant of a homologous MDH polypeptide. In an even more preferred embodiment, the recombinant yeast cell is a recombinant *Saccharomyces*, for example *S. cerevisiae*, and the MDH mutant is a mutant of a homologous MDH, for example MDH2 or MDH3. In a more specific embodiment, said recombinant yeast cell comprises a nucleic sequence encoding a mutant polypeptide having malate dehydrogenase activity as defined in Table 1 and wherein the amino acid residue corresponding to amino acid 34 in SEQ ID NO: 39 is selected from glycine (G) or serine (S).

Standard genetic techniques, such as overexpression of enzymes in the host cells, genetic modification of host cells, or hybridisation techniques, are known methods in the art, such as described in Sambrook et al. (Molecular Cloning: A Laboratory Manual, 3$^{rd}$ edition, *Cold Spring Harbor Laboratory Press*, Cold Spring Harbor Laboratory, N Y, 2001) or Ausubel et al. (Current protocols in molecular biology, Green Publishing and Wiley Interscience, N Y, 1987). Methods for transformation, genetic modification of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

As used herein, the terms "nucleic acid", "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The term "nucleic acid construct" is herein referred to as a nucleic acid molecule, either single- or double-stranded, which is isolated from a naturally-occurring gene or, more typically, which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence in a host cell, wherein said control sequences are operably linked to said coding sequence.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences known to one of skilled in the art. A "constitutive" promoter is a promoter that is active under most environmental and developmental conditions. An "inducible" promoter is a promoter that is active under environmental or developmental regulation.

A promoter that could be used to achieve the expression of a nucleotide sequence coding for an enzyme such a malate dehydrogenase or any other enzyme introduced in the host cell of the invention, may be not native to a nucleotide sequence coding for the enzyme to be expressed, i.e. a promoter that is heterologous to the nucleotide sequence (coding sequence) to which it is operably linked. Preferably, the promoter is homologous, i.e. endogenous to the host cell.

Suitable promoters in this context include both constitutive and inducible natural promoters as well as engineered promoters, which are well known to the person skilled in the art. Suitable promoters in eukaryotic host cells may be GAL7, GAL10, or GAL 1, CYC1, HIS3, ADH1, PGL, PH05, GAPDH, ADC1, TRP1, URA3, LEU2, ENO, TPI, and AOX1. Other suitable promoters include PDC, GPD1, PGK1, TEF1, and TDH.

Usually a nucleotide sequence encoding an enzyme comprises a "terminator". Any terminator, which is functional in the eukaryotic cell, may be used in the present invention. Preferred terminators are obtained from natural genes of the host cell. Suitable terminator sequences are well known in the art. Preferably, such terminators are combined with mutations that prevent nonsense mediated mRNA decay in the host cell of the invention (see for example: Shirley et al., 2002, *Genetics* 161:1465-1482).

The nucleic acid construct may be incorporated into a "vector", such as an expression vector and/or into a host cell in order to effect expression of the polypeptide to be expressed.

The expression vector may be any vector (e.g., a plasmid or virus), which can be conveniently subjected to recombinant DNA procedures and can bring about the expression of the polynucleotide encoding the polypeptide having malate dehydrogenase activity. The choice of the vector will typically depend on the compatibility of the vector with the host cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. If intended for use in a host cell of fungal origin, a suitable episomal nucleic acid construct may e.g. be based on the yeast 2p or pKD1 plasmids (Gleer et al., 1991, *Biotechnology* 9: 968-975), or the AMA plasmids (Fierro et al., 1995, *Curr Genet.* 29:482-489).

Alternatively, the expression vector may be one which, when introduced into the host cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 20 bp, at least 30 bp, at least 50 bp, at least 0.1 kb, at least 0.2 kb, at least 0.5 kb, at least 1 kb, at least 2 kb or longer. The efficiency of targeted integration into the genome of the host cell, i.e.

integration in a predetermined target locus, is increased by augmented homologous recombination abilities of the host cell.

The homologous flanking DNA sequences in the cloning vector, which are homologous to the target locus, are derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l.

A nucleic acid construct or expression vector may be assembled in vivo in a host cell of the invention and, optionally, integrated into the genome of the cell in a single step (see, for example, WO2013/076280)

More than one copy of a nucleic acid construct or expression vector of the invention may be inserted into the host cell to increase production of the polypeptide having malate dehydrogenase activity (over-expression) encoded by the nucleic acid sequence comprised within the nucleic acid construct. This can be done, preferably by integrating into its genome two or more copies of the nucleic acid, more preferably by targeting the integration of the nucleic acid at a highly expressed locus defined as defined above.

It will be appreciated by those skilled in the art that the design of the expression vector can depend on such factors as the choice of the host cell to be transformed, the level of expression of protein desired, etc.

A nucleic acid construct and/or expression vector of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell well known to those skilled in the art. Suitable methods for transforming or transfecting host cells can be found in Sambrook et al. (Molecular Cloning: A Laboratory Manual, 3rd edition, *Cold Spring Harbor Laboratory Press*, Cold Spring Harbor Laboratory, N Y, 2001), Davis et al. (Basic Methods in Molecular Biology, 1$^{st}$ edition, *Elsevier,* 1986) and other laboratory manuals.

Cytosolic expression of the enzymes described above may be obtained by deletion of a peroxisomal or mitochondrial targeting signal. The presence of a peroxisomal or mitochondrial targeting signal may for instance be determined by the method disclosed by Schlüter et al. (Schluter et al., 2007, *Nucleic Acid Research* 35: D815-D822).

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) *J. Mol. Biol.* 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. *Trends in Genetics* 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the blastn and blastx programs (version 2.2.31 or above) of Altschul, et al. (1990) *J. Mol. Biol.* 215:403-10. BLAST nucleotide searches can be performed with the blastn program, score=100, word-size=11 to obtain nucleotide sequences homologous to nucleic acid molecules of the invention. BLAST protein searches can be performed with the blastx program, score=50, word-size=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., blastx and blastn) can be used. See the homepage of the National Center for Biotechnology Information at http://www.ncbi.nlm.nih.gov/.

According to the present invention, there is also provided a process for the production of a dicarboxylic acid, such as succinic acid, which process comprises fermenting the recombinant host cell of the invention as described herein above, under conditions suitable for production of the dicarboxylic acid, and optionally, recovering the dicarboxylic acid from the fermentation medium.

In the process, the recombinant host cell of the invention is fermented in a vessel comprising a suitable fermentation medium. The term fermenting, fermentation or fermented and the like as used herein refers to the microbial production of compounds, here dicarboxylic acids from carbohydrates.

Preferably, the fermentation product is a dicarboxylic acid, preferably malic acid, fumaric acid and/or succinic acid, preferably succinic acid.

A batch fermentation is defined herein as a fermentation wherein all nutrients are added at the start of a fermentation.

A fed-batch fermentation is a batch fermentation wherein the nutrients are added during the fermentation. Products in a batch and fed-batch fermentation may be harvested at a suitable moment, for instance when one or more nutrients are exhausted.

A continuous fermentation is a fermentation wherein nutrients are continuously added to the fermentation and wherein products are continuously removed from the fermentation.

In one embodiment fermenting the host cell in the process of the invention is carried out under carbohydrate limiting conditions. As used herein, carbohydrate limiting conditions are defined as maintaining the carbohydrate concentration below 10 g/l, for example about 5 g/l.

The process for the production of dicarboxylic acid according to the present invention may be carried out in any suitable volume and scale, preferably on an industrial scale. Industrial scale is defined herein as a volume of at least 10, or 100 litres, preferably at least 1 cubic metre, preferably at least 10, or 100 cubic metres, preferably at least 1000 cubic metres, usually below 10,000 cubic metres.

Fermenting the recombinant host cell in the process of the invention may be carried out in any suitable fermentation medium comprising a suitable nitrogen source, carbohydrate and other nutrients required for growth and production of a dicarboxylic acid in the process of the invention. A suitable carbohydrate in the fermentation process according to the invention may be glucose, galactose, xylose, arabinose, sucrose, or maltose.

In one embodiment, the fermentation process is carried out under a partial $CO_2$ pressure of between 5% and 60%, preferably about 50%.

The pH during the process for the production of dicarboxylic acid usually lowers during the production of the dicarboxylic acid. Preferably, the pH in the process for the production of dicarboxylic acid ranges between 1 and 5, preferably between 1.5 and 4.5, more preferably between 2 and 4.

In another preferred embodiment, the process according to the present invention comprises a step of preculturing the host cell under aerobic conditions in the presence of a carbohydrate. Preferably, the fermentation of the host cell during preculturing is carried out at a pH of between 4 and 6. Preferably, the carbohydrate during preculturing is a non-repressing carbohydrate, preferably galactose. It has been found advantageous to preculture host cells on a non-repressing carbohydrate, since this prevents glucose repression occurring, which may negatively influence the amount of biomass produced. In addition, it has been found that a step of preculturing host cells under aerobic conditions results in a higher biomass yield and a faster growth. Preferably, the preculturing is carried out in batch mode.

A propagation step for producing increased biomass is typically carried out, preferably under carbohydrate limiting conditions.

The process for producing a dicarboxylic acid may be carried out at any suitable temperature. A suitable temperature may for instance be between about 10 and about 40 degrees Celsius, for instance between about 15 and about 30 degrees Celsius.

In an embodiment, the process of the invention is carried out in such a way that at least a portion of the host cells is reused, i.e. recycled. The cells may be recycled back into the original vessel or into a second vessel. Preferably, the medium into which the recycled host cells are introduced is supplemented with a vitamin and/or a trace element.

In a preferred embodiment, the fermentation medium comprises an amount of succinic acid of between 1 and 150 g/l, preferably between 5 and 100 g/l, more preferably between 10 and 80 g/l or between 15 and 60 g/l of succinic acid. In any event, the recombinant host cell of the invention will typically be capable of accumulating more succinic acid in the fermentation medium as compared to a host cell that has been modified with a reference MDH polypeptide, for example that of SEQ ID NO: 39.

The process for the production of a dicarboxylic acid may further comprise recovering the dicarboxylic acid. Recovery of the dicarboxylic acid may be carried out by any suitable method known in the art, for instance by crystallization, ammonium precipitation, ion exchange technology, centrifugation or filtration or any suitable combination of these methods.

In a preferred embodiment, the recovery of the dicarboxylic acid comprises crystallizing the dicarboxylic acid and forming dicarboxylic acid crystals. Preferably, the crystallizing of the dicarboxylic acid comprises removing part of the fermentation medium, preferably by evaporation, to obtain a concentrated medium.

According to the present invention, the dicarboxylic acid, such as succinic acid may be recovered by crystallizing the dicarboxylic acid, such as succinic acid, from an aqueous solution having a pH of between 1 and 5 and comprising succinic acid, comprising evaporating part of the aqueous solution to obtain a concentrated solution, lowering the temperature of the concentrated solution to a value of between 5 and 35 degrees Celsius, wherein succinic acid crystals are formed. Preferably, the crystallizing comprises bringing the temperature of the concentrated medium to a temperature of between 10 and 30 degrees Celsius, preferably between 15 and 25 degrees Celsius. Preferably, the fermentation medium has a pH of between 1.5 and 4.5, preferably between 2 and 4.

It has been found that crystallizing the dicarboxylic acid, such as succinic acid, at higher temperatures such as between 10 and 30 degrees Celsius results in crystals of a dicarboxylic acid, such as succinic acid, with a lower amount of impurities such as organic acid, protein, color and/or odor, than crystals of a dicarboxylic acid, such as succinic acid, that were crystallized at a low temperature of below 10 degrees.

Another advantage of crystallizing succinic acid at a higher temperature is that it requires a lower amount of energy for cooling the aqueous solution as compared to a process wherein crystallizing the dicarboxylic acid is carried out below 10 or 5 degrees Celsius, resulting in a more economical and sustainable process.

Preferably, the crystallizing of the dicarboxylic acid, such as succinic acid, comprises a step of washing the dicarboxylic acid crystals. Dicarboxylic acid, such as succinic acid, may be crystallized directly from the fermentation medium having a pH of between 1 and 5 to a purity of at least 90% w/w, preferably at least 95, 96, 97, or at least 98%, or 99 to 100% w/w.

In a preferred embodiment, the process for the production of a dicarboxylic acid further comprises using the dicarboxylic acid in an industrial process.

Preferably, the dicarboxylic acid, such as succinic acid, that is prepared in the process according to the present invention is further converted into a desirable product. A desirable product may for instance be a polymer, such as polybutylene succinic acid (PBS), a deicing agent, a food additive, a cosmetic additive or a surfactant. That is to say, the invention provides a method for the production of a product, for example, a polymer, such as polybutylene succinic acid (PBS), a deicing agent, a food additive, a cosmetic additive or a surfactant, which method comprises:

producing a dicarboxylic acid as described herein; and using said dicarboxylic acid in the production of said product.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General Materials and Methods

DNA Procedures

Standard DNA procedures were carried out as described elsewhere (Sambrook et al., 1989, *Molecular cloning: a laboratory manual*, $2^{nd}$ Ed., Cold Spring Harbor Laboratory Press, Cold Spring Harbor, N.Y.) unless otherwise stated. DNA was amplified using the proofreading enzyme Phusion polymerase (New England Biolabs, USA) according to manufacturer's instructions. Restriction enzymes were from Invitrogen or New England Biolabs.

Microtiter Plate (MTP) Fermentation of Dicarboxylic Acid Production Strains

To determine dicarboxylic acid production, strains were grown in triplicate in micro titer plates in humidity shakers (Infors) for 3 days at 30 degrees at 550 rpm and 80% humidity. The medium was based on Verduyn medium (Verduyn C, Postma E, Scheffers W A, Van Dijken J P. Yeast, 1992 July; 8(7):501-517), but modifications in carbon and nitrogen source were made as described herein below.

| MTP pre-culture medium composition | | |
|---|---|---|
| Raw material | | Concentration (g/l) |
| Galactose | $C_6H_{12}O_6 \cdot H_2O$ | 40.0 |
| Urea | $(NH_2)_2CO$ | 2.3 |
| Potassium dihydrogen phosphate | $KH_2PO_4$ | 3.0 |
| Magnesium sulphate | $MgSO_4 \cdot 7H_2O$ | 0.5 |
| Trace element solution[a] | | 1 |
| Vitamin solution[b] | | 1 |
| Component | Formula | Concentration (g/kg) |
| EDTA | $C_{10}H_{14}N_2Na_2O_8 \cdot 2H_2O$ | 15.00 |
| Zincsulphate•$7H_2O$ | $ZnSO_4 \cdot 7H_2O$ | 4.50 |
| Manganese-chloride•$2H_2O$ | $MnCl_2 \cdot 2H_2O$ | 0.84 |
| Cobalt (II) chloride•$6H_2O$ | $CoCl_2 \cdot 6H_2O$ | 0.30 |
| Copper (II) sulphate•$5H_2O$ | $CuSO_4 \cdot 5H_2O$ | 0.30 |
| Sodium molybdenum•$2H_2O$ | $Na_2MoO_4 \cdot 2H_2O$ | 0.40 |
| Calcium-chloride•$2H_2O$ | $CaCl_2 \cdot 2H_2O$ | 4.50 |
| Ironsulphate•$7H_2O$ | $FeSO_4 \cdot 7H_2O$ | 3.00 |
| Boric acid | $H_3BO_3$ | 1.00 |
| Potassium iodide | KI | 0.10 |
| Biotin (D−) | $C_{10}H_{16}N_2O_3S$ | 0.05 |
| Ca D(+) panthothenate | $C_{18}H_{32}CaN_2O_{10}$ | 1.00 |
| Nicotinic acid | $C_6H_5NO_2$ | 1.00 |
| Myo-inositol | $C_6H_{12}O_6$ | 25.00 |
| Thiamine chloride hydrochloride | $C_{12}H_{18}Cl_{12}N_4OS \cdot xH_2O$ | 1.00 |
| Pyridoxol hydrochloride | $C_8H_{12}ClNO_3$ | 1.00 |
| p-aminobenzoic acid | $C_7H_7NO_2$ | 0.20 |

[a]Trace elements solution
[b]Vitamin solution 80 microliters of pre-culture was used to inoculate 2.5 ml of medium with 1.5% galactose as carbon source in 24-well plates. The cultures were grown for 72 hours in humidity shakers (Infors) at 30° C., 550 rpm, 80% humidity. After generating biomass, a production experiment was started by re-suspending cells into 2.5 ml of mineral medium with glucose as carbon source. The main cultures were incubated in humidity shakers (Infors) at 30 degrees at 550 rpm and 80% humidity and samples were taken after 48 hours of cultivation.

Metabolite Analysis of MTP Samples by NMR

For metabolite analysis of MTP samples, 90 microliter of supernatant of fermentation samples is mixed with 10 microliter of NMR standard (20 g/l maleic acid) and 100 microliter of 10% $D_2O$ solution. The samples are lyophilized and subsequently dissolved in 1 mL $D_2O$.

1D 1H NMR spectra are recorded on a BEST Bruker Avance III spectrometer, operating at a proton frequency of 500 MHz, equipped with a He-cooled cryo probe, using a pulse program without water suppression (ZG) at a temperature of 300 K, with a 90 degree excitation pulse, acquisition time of 2.0 seconds and a relaxation delay of 40 seconds. The number of scans was set at 8.

The malic acid concentration [in g/l] is calculated based on the following signals ($\delta$ relative to 4,4-dimethyl-4-silapentane-1-sulfonic acid):

Malic acid: Depending on the pH and overlap of the $\alpha$-CH2 and the CH(OH) signals with other compounds, one of the three malic acid signals is chosen for quantification, $\alpha$-CH (A) (2.92 ppm, n=1H, double doublet or dd), $\alpha$-CH(X) (2.85 ppm, n=1H, dd) or CH(OH) (4.6 ppm, n=1H, dd).

The succinic acid concentration [in g/L] is calculated based on the following signals ($\delta$ relative to 4,4-dimethyl-4-silapentane-1-sulfonic acid):

Succinic acid: succinic acid signal at 2.67 ppm (s, 4H)

The signal used for the standard: maleic acid peak around 6.3 ppm (S, 2H).

Quantification by NMR is described by Bharti et al., 2012, TrAC *Trends* in Analytical Chemistry 35:5-26.

Example 1: Construction of Strain SUC-1029

Strain CEN.PK 113-7D (MATa HIS3 LEU2 TRP1 MAL2-8 SUC2) was used as a starting point to construct strain SUC-1029. A fumarase gene of *Rhyzopus oryzae* (FUMR) was transformed to strain CEN.PK113-7D as described below.

Generation of PCR Fragments

PCR fragment 9 was obtained by PCR amplification of SEQ ID NO: 34 using primers amplifying the entire nucleotide sequence of SEQ ID NO: 34. SEQ ID NO: 34 describes a synthetic polynucleotide containing the fumarase (FUMR) nucleotide sequence from *Rhyzopus oryzae* as disclosed in patent application WO2009/065779. The gene sequence was codon pair optimized for expression in *S. cerevisiae* as disclosed in patent application WO2008/000632. Expression of the FUMR gene is controlled by the TDH1 promoter (600 bp directly before the start codon of the TDH1 gene) and the TDH1 terminator (300 bp directly after the stop codon of the TDH1 gene). The TDH1 promoter and TDH1 terminator sequences controlling expression of FUMR are native sequences derived from *Saccharomyces cerevisiae* S288C. The 599 bp region at the 5' end of SEQ ID NO: 34, upstream of the TDH1 promoter, is a region homologous to the YPRCtau3 locus.

PCR fragment 10 was obtained by PCR amplification of SEQ ID NO: 35 using primers amplifying the entire nucleotide sequence of SEQ ID NO: 35. SEQ ID NO: 35 describes a synthetic polynucleotide containing part of the pSUC227 plasmid sequence, described in PCT/EP2013/055047. The 5' end of SEQ ID NO: 35 contains overlap with the 3' end of SEQ ID NO: 34. The 3' end of SEQ ID NO: 35 contains overlap with the 5' end of SEQ ID NO: 36.

PCR fragment 11 was obtained by PCR amplification of SEQ ID NO: 36 using primers amplifying the entire nucleotide sequence of SEQ ID NO: 36. SEQ ID NO: 36 describes a synthetic polynucleotide containing part of the pSUC225 plasmid sequence, described in PCT/EP2013/055047. The 3' end of SEQ ID NO: 36 contains overlap with the 5' end of SEQ ID NO: 37.

PCR fragment 12 was obtained by PCR amplification of SEQ ID NO: 37 using primers amplifying the entire nucleotide sequence of SEQ ID NO: 37. SEQ ID NO: 37 describes a synthetic polynucleotide homologous to the YPRCtau3 locus.

PCR fragments 9 to 12 were purified using the DNA Clean & Concentrator™-25 kit (Zymo Research, Irvine, Calif., USA) according to manufacturer's instructions.

Transformation to CEN.PK113-7D in Order to Construct Strain SUC-1029

Yeast transformation was done by a method known by persons skilled in the art. *S. cerevisiae* strain CEN.PK113-7D was transformed with purified PCR fragments 9 to 12 PCR fragments 10 and 11 contained overlaps at their 5' and 3' ends and PCR fragments 9 and 12 at their 3' and 5' end respectively, such that this allowed homologous recombination of all four PCR fragments (FIG. 1). The 5' end of PCR fragment 9 and the 3' end of PCR fragment 12 were homologous to the YPRCtau3 locus and enabled integration of all four PCR fragments in the YPRCtau3 locus (FIG. 1). This resulted in one linear fragment consisting of PCR fragments 9 to 12 integrated in the YPRCtau3 locus, which is located on chromosome XVI.

Transformation mixtures were plated on YEPhD-agar (per liter: 10 grams yeast extract, 20 grams PhytonePeptone, 20 grams glucose, 20 grams agar) containing 200 μg G418 (Sigma Aldrich, Zwijndrecht, The Netherlands) per ml. After three days of growth at 30° C., individual transformants were re-streaked on YEPh-agar plates containing 20 grams glucose per liter and 200 μg G418 per ml.

Subsequently, the marker cassette and Cre-recombinase gene present on the integrated PCR fragments 10 and 11 were removed by recombination between the lox66 and lox71 sites that flank the KanMX marker and the CRE gene encoding the CRE recombinase by CRE recombinase, using the method described in PCT/EP2013/055047, resulting in removal of the KanMX marker and the CRE gene and leaving a lox72 site as a result of recombination between the lox66 and lox71 sites. The resulting markerfree strain was named SUC-1029.

Presence of the introduced FUMR gene was confirmed by using PCR using primer sequences that can anneal to the coding sequences of the ORF's encoded by SEQ ID NO: 34. Correct integration and removal of the KanMX marker was confirmed by PCR using primers 5' and 3' from the YPRCtau3 locus, not hybridizing on the YPRCtau3 homologous regions present on PCR fragments 9 and 12.

Example 2: Construction of Strain SUC-1112

Generation of PCR Fragments

Primer sequences described in SEQ ID NO: 9 and SEQ ID NO: 10 were used to generate PCR fragment 1 consisting of the 5' INT59 integration site, using genomic DNA of strain *Saccharomyces cerevisiae* strain CEN.PK 113-7D (MATa HIS3 LEU2 TRP1 MAL2-8 SUC2) as template.

PCR fragment 2 was generated by using the primer sequences described in SEQ ID NO: 11 and SEQ ID NO: 12, using SEQ ID NO: 1 as template. SEQ ID NO: 1 encodes phosphoenolpyruvate carboxykinase (PCKa) from *Actinobacillus succinogenes*, as disclosed in patent application WO2009/065780. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the TPI1-promoter controls the expression of the PCKa-gene. Proper termination is controlled by a terminator sequence from *S. cerevisiae*, i.e. the GND2-terminator.

PCR fragment 3 was generated by using the primer sequences described in SEQ ID NO: 13 and SEQ ID NO: 14, using SEQ ID NO: 2 as template. SEQ ID NO: 2 encodes pyruvate carboxylase (PYC2) from *Saccharomyces cerevisiae*, as disclosed in patent application WO2009/065780. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the PGK1-promoter controls the expression of the PYC2-gene. Proper termination is controlled by a terminator sequence from *S. cerevisiae*, i.e. the ADH1-terminator.

PCR fragment 4 was generated by using the primer sequences described in SEQ ID NO: 15 and SEQ ID NO: 16, using SEQ ID NO: 3 as template. SEQ ID NO: 3 encodes a KanMX selection marker functional in *Saccharomyces cerevisiae* which was amplified from plasmid pUG7-EcoRV. pUG7-EcoRV is a variant of plasmid pUG6 described by Gueldener et al., (Nucleic Acids Res. 1996 Jul. 1; 24(13): 2519-24), in which the loxP sites present in pUG6 were changed into lox66 and lox71 sites (Lambert et al., Appl. Environ. Microbiol. 2007 February; 73(4):1126-35. Epub 2006 Dec. 1.)

PCR fragment 5 was generated by using the primer sequences described in SEQ ID NO: 17 and SEQ ID NO: 18, using SEQ ID NO: 4 as template. SEQ ID NO: 4 encodes a putative dicarboxylic acid transporter from *Aspergillus niger*, as disclosed in EP2495304. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the ENO1-promoter controls the expression of the DCT_02-gene. Proper termination is controlled by a terminator sequence from *S. cerevisiae*, i.e. the TEF2-terminator.

PCR fragment 6 was generated by using the primer sequences described in SEQ ID NO: 19 and SEQ ID NO: 20, using SEQ ID NO: 5 as template. SEQ ID NO: 5 encodes malate dehydrogenase (MDH3) from *Saccharomyces cerevisiae*, as disclosed in patent application WO2009/065778. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *Kluyveromyces lactis*, i.e. the promoter of ORF KLLA0_F20031g (uniprot accession number Q6CJA9) controls the expression of the MDH3-gene. Proper termination is controlled by a terminator sequence from *S. cerevisiae*, i.e. the GPM1-terminator.

PCR fragment 7 was generated by using the primer sequences described in SEQ ID NO: 21 and SEQ ID NO: 22, using SEQ ID NO: 6 as template. SEQ ID NO: 6 encodes fumarase (fumB) from *Escherichia coli* (E.C. 4.2.1.2, UniProt accession number P14407). The gene sequence was codon pair optimized for expression in *S. cerevisiae* as disclosed in patent application WO2008/000632. The synthetic sequence, which includes promoter-gene-terminator sequence, including appropriate restriction sites, was synthesized by DNA 2.0 (Menlo Park, Calif., USA). The synthetic gene is under control of (or operable linked to) a promoter from *S. cerevisiae*, i.e. the TDH3-promoter controls the expression of the controls the expression of the fumB-gene. Proper termination is controlled by a terminator sequence from *S. cerevisiae*, i.e. the TDH1-terminator.

PCR fragment 8 was generated by using the primer sequences described in SEQ ID NO: 23 and SEQ ID NO: 24, using SEQ ID NO: 7 as template. SEQ ID NO: 7 encodes encodes fumarate reductase (FRDg) from *Trypanosoma brucei*, as disclosed in patent application WO2009/065778. The gene sequence was codon pair optimized for expression in *S. cerevisiae* as disclosed in patent application WO2008/000632. The synthetic sequence, which includes promoter-gene-terminator sequence, including appropriate restriction sites, was synthesized by DNA 2.0 (Menlo Park, Calif., USA). The synthetic gene is under control of (or operable linked to) a promoter from *S. cerevisiae*, i.e. the TEF1-promoter controls the expression of the controls the expression of the fumB-gene. Proper termination is controlled by a terminator sequence from *S. cerevisiae*, i.e. the TAL1-terminator.

Primer sequences described in SEQ ID NO: 40 and SEQ ID NO: 41 were used to generate PCR fragment 113 consisting of the 3' INT59 integration site, using genomic DNA of strain CEN.PK 113-7D as template.

PCR fragments 1 to 8 and PCR fragment 113 were purified using the DNA Clean & Concentrator™-25 kit (Zymo Research, Irvine, Calif., USA) according to manufacturer's instructions.

Transformation to SUC-1029 in Order to Construct Strain SUC-1112

Yeast transformation was done by a method known by persons skilled in the art. *S. cerevisiae* strain SUC-1029 was transformed with purified PCR fragments 1 to 8 and PCR fragment 113. PCR fragments 2 to 8 contained overlaps at their 5' and 3' ends and PCR fragments 1 and 113 at their 3' and 5' end respectively, such that this allowed homologous recombination of all eight PCR fragments. The 5' end of PCR fragment 1 and the 3' end of PCR fragment 113 were homologous to the INT59 locus and enabled integration of all nine PCR fragments in the INT59 locus (see FIG. 2). This resulted in one linear fragment consisting of PCR fragments 2 to 8 integrated in the INT59 locus. This method of integration is described in patent application WO2013076280. The INT59 locus is located at chromosome XI, 923 bp downstream of YKR092C and 922 bp upstream of YKR093W.

Transformation mixtures were plated on YEPh-agar (per liter: 10 grams yeast extract, 20 grams PhytonePeptone, 20 grams agar) containing 20 grams galactose per liter and 200 µg G418 (Sigma Aldrich, Zwijndrecht, The Netherlands) per ml. After three days of growth at 30° C., individual transformants were re-streaked on YEPh-agar plates containing 20 grams galactose per liter and 200 µg G418 per ml. Presence of all introduced genes was confirmed by using PCR using primer sequences that can anneal to the coding sequences of the ORF's encoded by SEQ ID NO: 1 to SEQ ID NO: 7. The resulting strain was named SUC-1112. The KanMX marker, present in strain SUC-1112, can be removed if required.

Example 3: Transformation of a Malate Dehydrogenase Gene to Strain SUC-1112 and Production of Malic Acid in Resulting Transformants Generation of PCR Fragments Primer sequences described in SEQ ID NO: 25 and SEQ ID NO: 26 were used to generate PCR fragment 13 consisting of the 5' INT1 integration site, using genomic DNA of strain CEN.PK 113-7D as template.

PCR fragment 114 was generated by using the primer sequences described in SEQ ID NO: 43 and SEQ ID NO: 44, using SEQ ID NO: 42 as template. SEQ ID NO: 42 contains the ZWF1 gene, encoding Glucose-6-phosphate dehydrogenase (G6PD). This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *Kluyveromyces lactis*, i.e. the promoter of ORF KLLA0C05566g (uniprot accession number Q6CUE2) controls the expression of the ZWF1-gene. Proper termination is controlled by a terminator sequence from *S. cerevisiae*, i.e. the TEF1-terminator.

PCR fragment 115 was generated by using the primer sequences described in SEQ ID NO: 45 and SEQ ID NO: 28, using SEQ ID NO: 38 as template. SEQ ID NO: 38 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 February; 73(4):1126-35. Epub 2006 Dec. 1) and in which the KanMX marker was replaced by a nourseothricin marker (Goldstein and McCusker, Yeast. 1999 October; 15(14):1541-53).

PCR fragment 15 was generated by using the primer sequences described in SEQ ID NO: 29 and SEQ ID NO: 30, using SEQ ID NO: 31 as template. SEQ ID NO: 31 encodes malate dehydrogenase (MDH3) from *S. cerevisiae*. MDH3 is altered by the deletion of the SKL carboxy-terminal sequence as disclosed in patent application WO2013/

004670 A1. This synthetic sequence, which includes promoter-gene-terminator sequence, including appropriate restriction sites, was synthesized by DNA 2.0 (Menlo Park, Calif., USA). The gene sequence was codon pair optimized for expression in *S. cerevisiae* as disclosed in patent application WO2008/000632. The synthetic gene is under control of (or operable linked to) a promoter from *S. cerevisiae*, i.e. the TDH3-promoter controls the expression of the MDH3-gene. Proper termination is controlled by a terminator sequence from *S. cerevisiae*, i.e. the GPM1-terminator.

Primer sequences described in SEQ ID NO: 32 and SEQ ID NO: 33 were used to generate PCR fragment 16 consisting of the 3' INT1 integration site, using genomic DNA of strain CEN.PK 113-7D as template.

PCR fragments 13 to 16 were purified using the DNA Clean & Concentrator™-25 kit (Zymo Research, Irvine, Calif., USA) according to manufacturer's instructions.

Transformation to SUC-1112

Yeast transformation was done by a method known by persons skilled in the art. *S. cerevisiae* strain SUC-1112 was transformed with purified PCR fragments 13, 114, 115, 15 and 16. PCR fragments 114 and 115 and 15 contained overlaps at their 5' and 3' ends and PCR fragments 13 and 16 contained overlaps at their 3' and 5' end respectively, such that this allowed homologous recombination of all five PCR fragments. The 5' end of PCR fragment 13 and the 3' end of PCR fragment 16 were homologous to the INT1 locus and enabled integration of all four PCR fragments in the INT1 locus (see FIG. 3). This resulted in one linear fragment consisting of PCR fragments 13 to 16 integrated in the INT1 locus. This method of integration is described in patent application WO2013/076280. The INT1 locus is located at chromosome XV, 659 bp downstream of YOR071c and 998 bp upstream of YOR070c. This approach resulted in expression of the malate dehydrogenase protein of 340 amino acids as indicated in SEQ ID NO: 39 which lacks the C-terminal amino acid SKL as compared to the native sequence from *S. cerevisiae*.

Transformation mixtures were plated on YEPh-agar (per liter: 10 grams yeast extract, 20 grams PhytonePeptone, 20 grams agar)) containing 20 grams galactose per liter and 200 μg nourseothricin (Jena Bioscience, Germany) per ml. After three days of growth at 30° C., individual transformants were re-streaked on YEPh-agar plates containing 20 grams galactose per liter and 200 μg nourseothricin per ml. Presence of the introduced genes was confirmed by using PCR using primer sequences that can anneal to the coding sequences of the ORF's encoded present on PCR fragment 114, 115 and 15. To confirm integration of PCR fragments 13, 114, 115, 15 and 16 on the correct locus, primers annealing to the region 5' and 3' of the INT1 locus, not binding to the INT1 regions on PCR fragments 13 and 16 were used in combination with primers annealing to the ORF's on PCR fragments 114 and 15 such that only PCR product can be formed if PCR fragments 114 and 15 are integrated in the INT1 locus. Three resulting individual colonies SUC-1112+MDH3 #1, SUC-1112+MDH3 #2, SUC-1112+MDH3 #3. The KanMX and nourseothricin markers, present in strains SUC-1112+MDH3 #1, SUC-1112+MDH3 #2, SUC-1112+MDH3 #can be removed if required.

Dicarboxylic Acid Production

To determine dicarboxylic acid production MTP fermentations and NMR measurements were performed as described in General Materials and Methods.

In the supernatant of the SUC-1112+MDH3 strains, SUC-1112+MDH3 #1, SUC-1112+MDH3 #2, SUC-1112+MDH3 #3, which contain an additional copy of the MDH3 gene, present on PCR fragment 15, an average titer of 8.7 g/L malic acid was measured. Succinic acid levels were lower than expected; the strains appeared to have lost the FRDg gene resulting in limited conversion of malate to succinate.

Example 4: Transformation of Genes Encoding Malate Dehydrogenase Mutants to Strain SUC-1112 and Production of Malic Acid in Resulting Transformants Generation of PCR fragments PCR fragments 13 and 16 were generated as described in Example 3.

PCR fragment 14 was generated by using the primer sequences described in SEQ ID NO: 27 and SEQ ID NO: 28, using SEQ ID NO: 38 as template. SEQ ID NO: 38 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 February; 73(4):1126-35. Epub 2006 Dec. 1) and in which the KanMX marker was replaced by a nourseothricin marker (Goldstein and McCusker, Yeast. 1999 October; 15(14):1541-53).

Synthetic nucleotide sequences encoding different protein mutants of the reference malate dehydrogenase sequence that is described in SEQ ID NO: 39 were synthesized by DNA 2.0 (Menlo Park, Calif., USA). The synthetic nucleotide sequences encode a mutant amino acid sequence at positions 34 to 40 relative to the reference MDH3 sequence (SEQ ID NO: 39) as indicated in Table 1. Apart from encoding the indicated mutant amino acids in Table 1 the synthetic nucleotide sequence mutants are identical to SEQ ID NO: 31 The synthetic gene is under control of (or operable linked to) a promoter from *S. cerevisiae*, i.e. the TDH3-promoter controls the expression of the mutant MDH-gene. Proper termination is controlled by a terminator sequence from *S. cerevisiae*, i.e. the GPM1-terminator.

The synthetic gene sequences containing amongst others a TDH3 promoter-mutant MDH-GPM1 terminator and were amplified by PCR using the primer sequences described in SEQ ID NO: 29 and SEQ ID NO: 30, to generate PCR fragments 17 to 108 (see Table 1).

PCR fragments 13, 14, 16 and 17 to 108 were purified using the DNA Clean & Concentrator™-25 kit (Zymo Research, Irvine, Calif., USA) according to manufacturer's instructions.

Transformation to SUC-1112

Strain SUC-1112 was transformed with purified PCR fragments 13, 14 and 16 in combination with PCR fragments 17 to 108 individually. PCR fragment 14 and PCR fragments 17 to 108 contained overlaps at their 5' and 3' ends and PCR fragments 13 and 16 contained overlaps at their 3' and 5' end respectively, such that this allowed homologous recombination of all four PCR fragments. The 5' end of PCR fragment 13 and the 3' end of PCR fragment 16 were homologous to the INT1 locus and enabled integration of all four PCR fragments in the INT1 locus (FIG. 4). Transformation and selection of transformants is described in Example 2.

Dicarboxylic Acid Production

To determine dicarboxylic acid production, four independent SUC-1112 transformants expressing mutant malate dehydrogenase sequences were grown in micro titer plates as described in General Materials and Methods. Low amounts of succinic acid were produced due to the loss of FRDg (see Example 3), but MDH3 activity could still be determined by measuring malate levels. Average malic acid titers are depicted in Table 1. The average production of malic acid of several SUC-1112 transformants expressing mutant malate dehydrogenase sequences exceeded 10 g/L malic acid. Interestingly, mutants with a substitution of aspartic acid by a glycine or serine residue at position 34 show increased malate production. This is significantly more than the average malic acid titer of SUC-1112 transformed with the reference MDH3 sequence described in Example 3. By significantly more it is meant that the 95% confidence intervals of malic titers for strains with reference and improved mutant malate dehydrogenase sequences do not overlap. The upper limit of the 95% confidence interval for the malic acid titer of SUC-1112 transformed with the reference MDH3 sequence lies below 10 g/L.

TABLE 1

Average malic acid titers measured in the supernatant of production medium after 4 days cultivation of transformants of strain SUC-1112, expressing phosphoenolpyruvate carboxykinase (PCKa), pyruvate carboxylase (PYC2), malate dehydrogenase (MDH3), fumarase (FUMR and fumB), dicarboxylic acid transporter (DCT 02), and transformed with the nucleotide sequence encoding the reference malate dehydrogenase (SEQ ID NO: 39) or a malate dehydrogenase mutant (MUT 001-MUT 94), which contains mutations as compared to the reference sequence in the amino acid positions indicated below.

| PCR fragment | Clone | Loop sequence (amino acid position) | | | | | | | Average malic acid titer (g/L) |
|---|---|---|---|---|---|---|---|---|---|
| | | 34 | 35 | 36 | 37 | 38 | 39 | 40 | |
| 15 | SUC-1112 + MDH3 reference | D | I | R | A | A | E | G | 8.7 g/L |
| 17 | MUT_001 | D | I | Q | A | A | E | G | 9.0 |
| 18 | MUT_002 | D | I | S | A | A | E | G | 9.1 |
| 19 | MUT_003 | D | I | R | A | A | E | G | 9.0 |
| 20 | MUT_004 | D | I | Q | A | A | E | G | 9.7 |
| 21 | MUT_005 | D | S | S | A | A | E | G | 9.8 |
| 22 | MUT_006 | S | I | R | A | A | E | G | 10.1 |
| 23 | MUT_007 | S | I | Q | A | A | E | G | 11.7 |
| 24 | MUT_008 | S | I | S | A | A | E | G | 17.1 |
| 25 | MUT_009 | S | S | R | A | A | E | G | 16.1 |
| 26 | MUT_010 | S | S | Q | A | A | E | G | 16.4 |
| 27 | MUT_011 | S | S | S | A | A | E | G | 16.5 |
| 28 | MUT_012 | G | I | R | A | A | E | G | 16.6 |
| 29 | MUT_013 | G | I | Q | A | A | E | G | 16.2 |
| 30 | MUT_014 | G | I | S | A | A | E | G | 16.5 |
| 31 | MUT_015 | G | S | R | A | A | E | G | 15.8 |
| 32 | MUT_016 | G | S | Q | A | A | E | G | 16.5 |
| 33 | MUT_017 | G | S | S | A | A | E | G | 15.9 |
| 34 | MUT_018 | D | I | A | V | T | P | G | 9.1 |
| 35 | MUT_019 | D | I | A | N | V | K | G | 9.0 |
| 36 | MUT_020 | D | I | A | N | V | K | G | 9.2 |
| 37 | MUT_021 | D | I | Q | N | V | K | G | 9.2 |
| 38 | MUT_022 | D | I | S | N | V | K | G | 8.8 |
| 39 | MUT_023 | D | S | A | N | V | K | G | 9.3 |
| 40 | MUT_024 | D | S | R | N | V | K | G | 9.3 |
| 41 | MUT_025 | D | S | Q | N | V | K | G | 8.4 |
| 42 | MUT_026 | D | S | S | N | V | K | G | 9.3 |
| 43 | MUT_027 | S | I | A | N | V | K | G | 15.4 |
| 44 | MUT_028 | S | I | R | N | V | K | G | 14.4 |
| 45 | MUT_029 | S | I | Q | N | V | K | G | 11.7 |
| 46 | MUT_030 | S | I | S | N | V | K | G | 16.1 |
| 47 | MUT_031 | S | S | A | N | V | K | G | 15.8 |
| 48 | MUT_032 | S | S | R | N | V | K | G | 15.8 |
| 49 | MUT_033 | S | S | Q | N | V | K | G | 15.7 |
| 50 | MUT_034 | S | S | S | N | V | K | G | 16.1 |
| 51 | MUT_035 | G | I | A | N | V | K | G | 15.7 |
| 52 | MUT_036 | G | I | R | N | V | K | G | 14.2 |
| 53 | MUT_037 | G | I | Q | N | V | K | G | 9.5 |
| 54 | MUT_038 | G | I | S | N | V | K | G | 16.6 |
| 55 | MUT_039 | G | S | A | N | V | K | G | 11.8 |
| 56 | MUT_040 | G | S | R | N | V | K | G | 14.4 |
| 57 | MUT_041 | G | S | Q | N | V | K | G | 15.4 |
| 58 | MUT_042 | G | S | S | N | V | K | G | 15.9 |
| 59 | MUT_043 | D | I | A | G | T | P | G | 8.3 |
| 60 | MUT_044 | D | I | R | G | T | P | G | 7.6 |
| 61 | MUT_045 | D | I | Q | G | T | P | G | 7.9 |
| 62 | MUT_046 | D | I | S | G | T | P | G | 8.5 |
| 63 | MUT_047 | D | S | A | G | T | P | G | 8.4 |
| 64 | MUT_048 | D | S | R | G | T | P | G | 8.4 |
| 65 | MUT_049 | D | S | Q | G | T | P | G | 8.7 |
| 66 | MUT_050 | D | S | S | G | T | P | G | 7.4 |
| 67 | MUT_051 | S | I | A | G | T | P | G | 9.7 |
| 68 | MUT_052 | S | I | R | G | T | P | G | 11.3 |
| 69 | MUT_053 | S | I | Q | G | T | P | G | 13.8 |
| 70 | MUT_054 | S | I | S | G | T | P | G | 13.4 |
| 71 | MUT_055 | S | S | A | G | T | P | G | 14.4 |
| 72 | MUT_056 | S | S | R | G | T | P | G | 13.9 |
| 73 | MUT_057 | S | S | Q | G | T | P | G | 14.2 |
| 74 | MUT_058 | S | S | S | G | T | P | G | 14.2 |
| 75 | MUT_059 | G | I | A | G | T | P | G | 13.9 |
| 76 | MUT_060 | G | I | R | G | T | P | G | 13.5 |
| 77 | MUT_061 | G | I | Q | G | T | P | G | 13.7 |
| 78 | MUT_062 | G | I | S | G | T | P | G | 14.2 |
| 79 | MUT_063 | G | S | A | G | T | P | G | 14.7 |
| 80 | MUT_064 | G | S | R | G | T | P | G | 11.8 |
| 81 | MUT_065 | G | S | Q | G | T | P | G | 14.4 |
| 82 | MUT_066 | G | S | S | G | T | P | G | 14.4 |
| 83 | MUT_067 | D | I | E | R | S | F | Q | 6.5 |
| 84 | MUT_068 | D | I | E | R | S | F | G | 6.4 |
| 85 | MUT_069 | D | I | E | A | S | F | Q | 8.6 |
| 86 | MUT_070 | D | I | E | A | S | F | G | 8.3 |
| 87 | MUT_071 | D | S | E | R | S | F | Q | 7.6 |
| 88 | MUT_072 | D | S | E | R | S | F | G | 8.5 |
| 89 | MUT_073 | D | S | E | A | S | F | Q | 6.9 |
| 90 | MUT_074 | D | S | E | A | S | F | G | 8.0 |
| 91 | MUT_075 | S | I | E | R | S | F | Q | 9.7 |
| 92 | MUT_076 | S | I | E | R | S | F | G | 15.1 |
| 93 | MUT_077 | S | I | E | A | S | F | Q | 7.8 |
| 94 | MUT_078 | S | I | E | A | S | F | G | 13.7 |
| 95 | MUT_079 | S | S | E | R | S | F | Q | 14.1 |
| 96 | MUT_080 | S | S | E | R | S | F | G | 14.1 |
| 97 | MUT_081 | S | S | E | A | S | F | Q | 12.2 |
| 98 | MUT_082 | S | S | E | A | S | F | G | 13.9 |
| 99 | MUT_083 | G | I | E | R | S | F | Q | 9.3 |
| 100 | MUT_084 | G | I | E | R | S | F | G | 14.0 |
| 101 | MUT_085 | G | I | E | A | S | F | Q | 6.3 |
| 102 | MUT_086 | G | I | E | A | S | F | G | 12.2 |
| 103 | MUT_087 | G | S | E | R | S | F | G | 14.0 |
| 104 | MUT_088 | G | S | E | R | S | F | G | 15.9 |
| 105 | MUT_089 | G | S | E | A | S | F | Q | 14.0 |
| 106 | MUT_090 | G | S | E | A | S | F | G | 14.5 |
| 107 | MUT_091 | D | I | P | Q | A | L | G | 7.6 |
| 108 | MUT_092 | D | S | P | Q | A | L | G | 7.3 |
| 109 | MUT_093 | S | S | P | Q | A | L | G | 14.2 |
| 110 | MUT_094 | G | S | P | Q | A | L | G | 16.0 |

Example 5: Measuring NADH and NADPH Specific Activity of Malate Dehydrogenase Mutants A total of 19 mutants were selected from Table 1 and re-cultured as described in General materials and methods. The biomass was harvested by centrifugation (4000 rpm, 10 min, 4° C.) and washed twice with PBS (phosphate buffered saline, Sigma Aldrich) after which the cell pellets were frozen at −20° C. Cell disruption was achieved in square welled 96-deepwell micro titer plates (MTP) using 0.5 mm acid washed glass beads in combination with the TissueLyser II from Qiagen (3000 rpm for 2×10 sec, cool on ice for 1 min between cycles). Glass beads taking up a volume of 600 µl were added to the cell pellet before addition of 1 ml in vivo like-assay medium (described in van Eunen et al. *FEBS Journal* 277: 749-760 adapted to contain 0.5 mM DTT (dithiothreitol, Sigma-Aldrich) and 0.1 mM PMSF (phenylmethanesulfonyl fluoride, Amresco). Glass beads were added by inverting the deep well MTP containing the frozen pellets over a standard MTP where each well is filled completely with glass beads (=a volume of 300 µl) and then inverting both plates, so that the glass beads fall onto the cell pellets. This process was repeated to obtain 600 µl glass beads in the cell pellets. Next 1 ml of in vivo like-assay medium described above was added. After cell disruption, cell debris was pelleted by centrifugation (4000 rpm, 30 min, 4° C.). The supernatant (soluble cell extracts) were collected and stored on ice. Protein concentration of the extracts was determined by Bradford, using bovine serum albumin (BSA) as standard.

Malate dehydrogenase (MDH) activity was assayed spectrophotometrically by following the decrease in absorbance at 340 nm caused by the oxidation of NADH or NADPH to NAD+ or NADP+, respectively. Assays contained 400 µM NADH or 400 µM NADPH, 2 mM oxaloacetic acid (Sigma Aldrich) and approximately 0.0625 mg protein ml$^{-1}$ soluble cell extracts in in vivo-like assay medium. Assays were performed in a final volume of 200 µl. Equal volume of soluble cell extracts were added in both the NADH and NADPH dependent assays. Reactions were started by the addition of 100 µl oxaloacetic acid stock solution (4 mM) and were followed for 9 minutes at 30 degrees Celsius and the slope was used as a measure of NADH or NADPH dependent MDH activity. The slope (in Δ A340/min) was determined with the 'slope' function in Microsoft Excel where the absorbance values were taken as 'y' values and the time in minutes as 'x' values. The 'RSQ' function in Microsoft Excel was used to check the quality of the slope fitting (criteria >0.9). The slope was corrected for the slope of blank reaction containing in vivo-like assay medium instead of substrate. Absorbance was measured using a Tecan Infinite M1000 plate reader. NADH dependent activity of each mutant was compared to the NADPH activity. The ratio of NADPH:NADH dependent activity or NADPH:NADH specificity ratio, was determined by:
1) Determining the slope (in Δ A340/min) of the NADPH-dependent MDH activity
2) Determining the slope (in Δ A340/min) NADH-dependent MDH activity
3) Dividing the slope of the NADPH-dependent MDH activity by the slope of the NADH-dependent MDH activity.

Figure 5A:
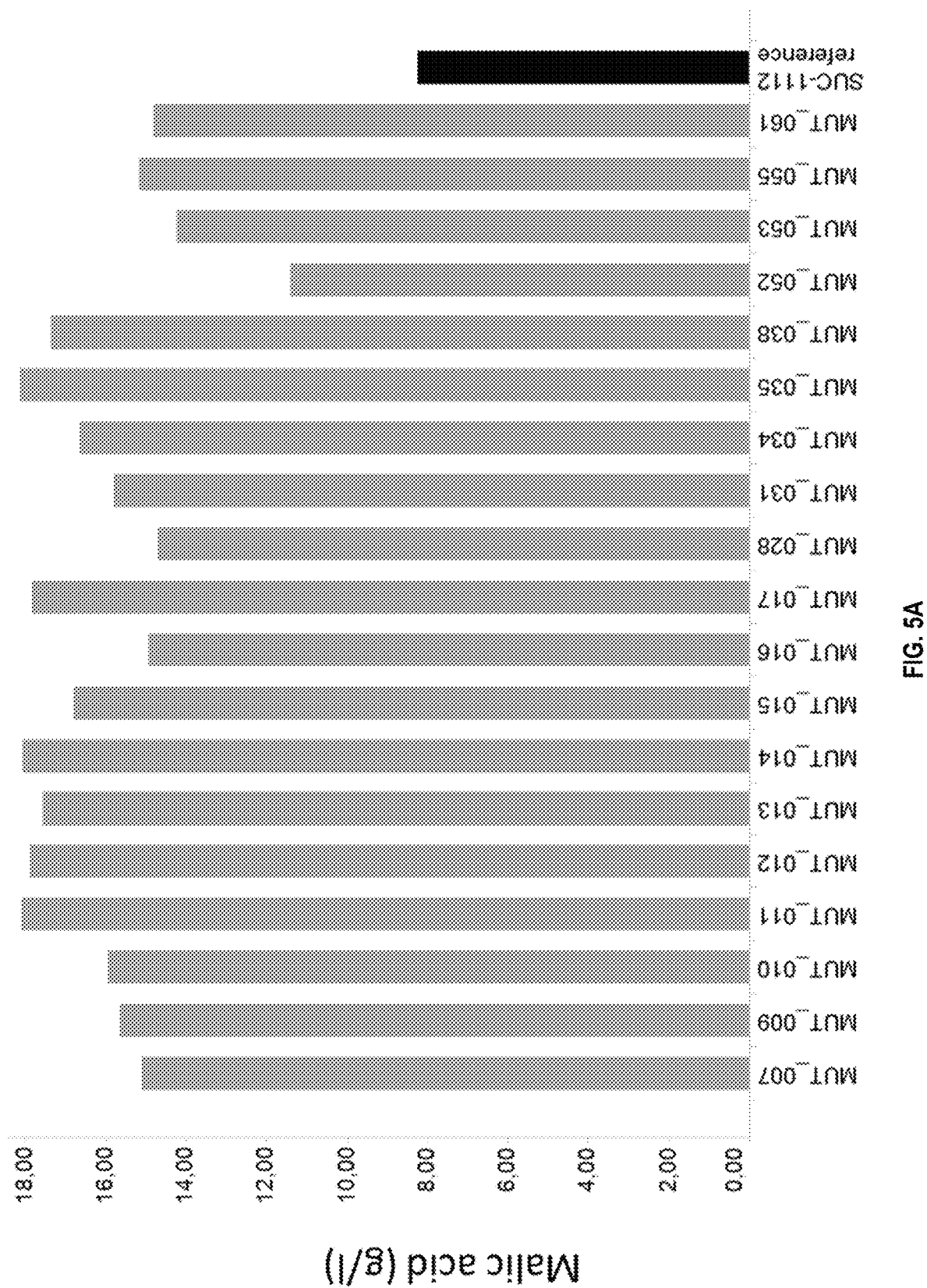
FIG. 5A: Average malic acid titers measured in the supernatant of production medium after cultivation of SUC-1112 transformants, expressing phosphoenolpyruvate carboxykinase (PCKa), pyruvate carboxylase (PYC2), malate dehydrogenase (MDH3), fumarase (FUMR and fumB), dicarboxylic acid transporter (DCT_02) and transformed with reference malate dehydrogenase (SEQ ID NO: 39) or mutant malate dehydrogenase, which contains mutations as compared to the reference sequence in the amino acid positions as indicated in Table 1. The malic acid titer was measured as described in General Materials and Methods and represents an average value obtained from three independent clones.
Figure 5C:
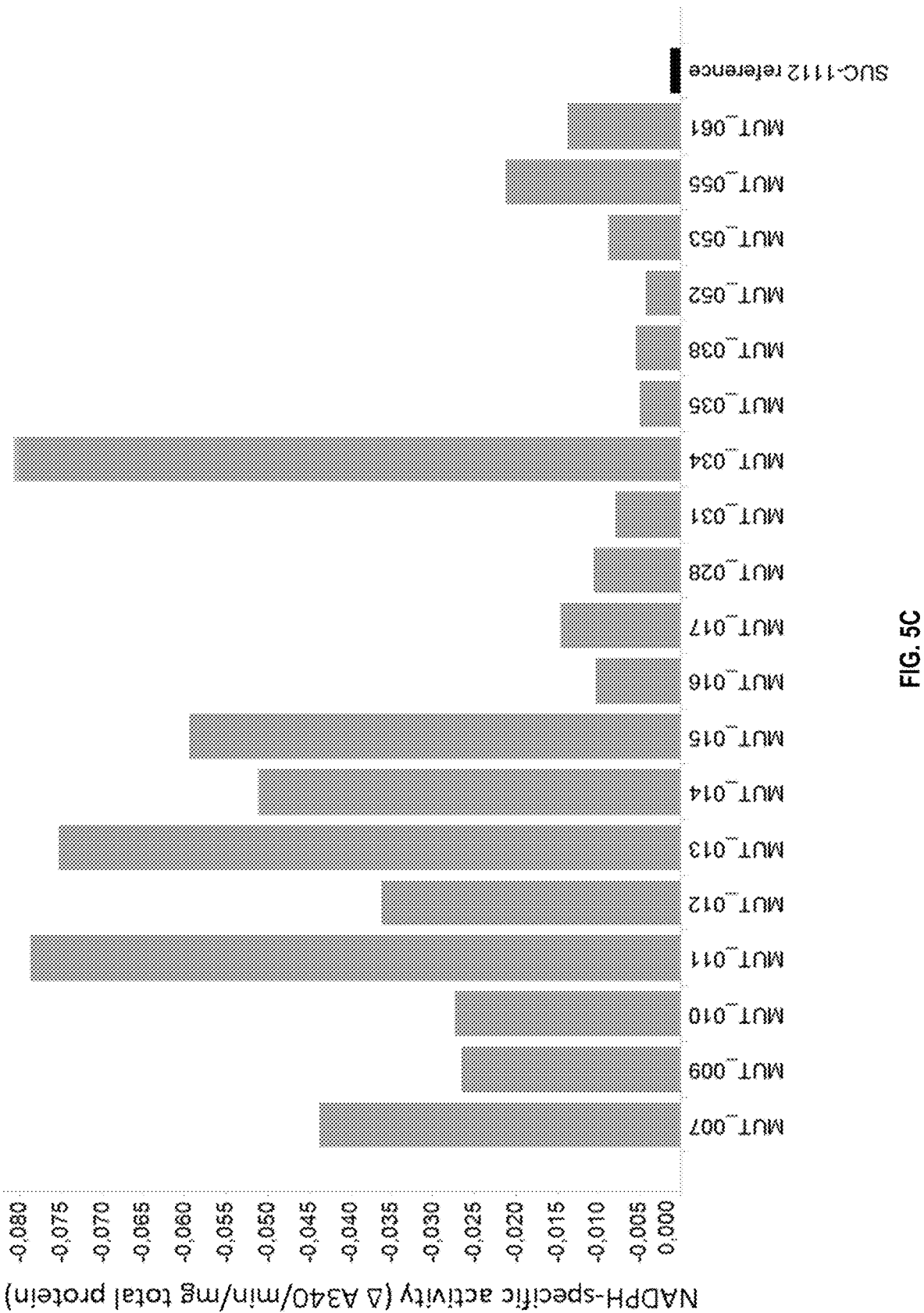
FIG. 5C: NADPH-specific malate dehydrogenase (MDH) activity of MDH mutants expressed in strain SUC-1112 (see Table 1 for specific mutations). Shown is activity, depicted as Δ A340/min/mg total protein. The value is negative as MDH-dependent NADPH oxidation results in a decrease in absorbance at 340 nm. A more negative value indicates more activity. The activity was measured as described in Example 5.
Figure 5D:
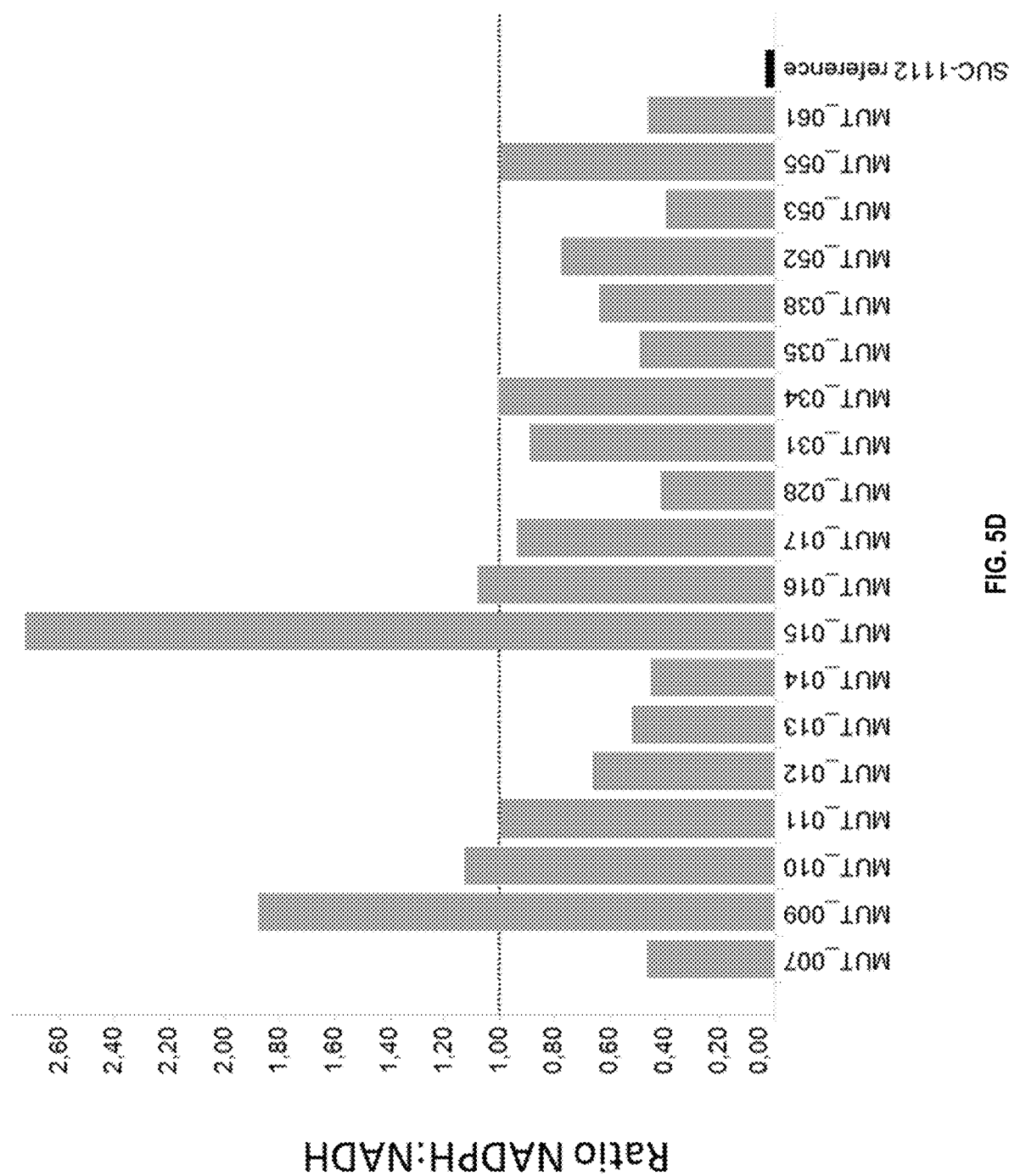
FIG. 5D: Ratio of NADPH:NADH dependent activity of MDH mutants expressed in strain SUC-1112 (see Table 1 for specific mutations). The activity was measured and the ratio was determined as described in Example 5. The dashed line indicates a NADPH:NADH ratio of 1.0.

To determine the ratio, slopes were used without normalization for amount of total protein as equal volumes of each mutant were used in the NADH and NADPH dependent MDH activity assays, The ratio was calculated for 19 mutants (FIG. 5D). An increased value for the ratio compared to the reference indicated that the cofactor specificity has been changed.

Supernatants of the 19 cultured mutants and the reference strain were analysed for malic acid titers as described in general materials and methods. The NADPH-specific and NADH-specific activities were measured as described above and normalized for total protein by dividing by the total protein concentration in the assay. The results are shown in FIGS. 5B-5C. Clearly, the 19 selected mutants have an enhanced NADPH-specific malate dehydrogenase activity. For most of the 19 mutants the NADH-specific malate dehydrogenase activity is decreased compared to the reference (FIG. 5B). Interestingly, in 6 mutants, the NADH-specific activity is increased (FIG. 5B), indicating that in these mutants both the NADH-specific activity and NADPH-specific activity is increased. In all mutants, the NADPH:NADH specificity ratio was increased (FIG. 5D).

Surprisingly, a substitution of aspartic acid by a glycine or serine residue at position 34 has a positive effect on the malic acid titer of SUC-1112 strains transformed with these malate dehydrogenase mutants (FIG. 5A).

Example 6: Construction of Strain REV-0001

Generation of PCR Fragments

Primer sequences described in SEQ ID NO: 54 and SEQ ID NO: 55 are used to generate PCR fragment 116 consisting of the 5' INT1 integration site, using genomic DNA of strain CEN.PK 113-7D as template.

PCR fragment 117 is generated by using the primer sequences described in SEQ ID NO: 56 and SEQ ID NO: 57, using SEQ ID NO: 38 as template. SEQ ID NO: 38 encodes a nourseothricin selection marker functional in *Saccharomyces cerevisiae* which was amplified from a modified version of plasmid pUG7-Nat. pUG7-Nat is a variant of plasmid pUG6 described by Gueldener et al., (Nucleic Acids Res. 1996 Jul. 1; 24(13):2519-24), in which the loxP sites present in pUG6 were changed into lox66 and lox71 sites (Lambert et al., Appl. Environ. Microbiol. 2007 February; 73(4):1126-35. Epub 2006 Dec. 1) and in which the KanMX marker was replaced by a nourseothricin marker (Goldstein and McCusker, Yeast. 1999 October; 15(14):1541-53).

PCR fragment 118 is generated by using the primer sequences described in SEQ ID NO: 60 and SEQ ID NO: 61, using SEQ ID NO: 62 as template. SEQ ID NO: 62 encodes fumarate reductase (FRDg) from *Trypanosoma brucei*, as disclosed in patent application WO2009/065778. This synthetic sequence, which includes promoter-gene-terminator sequence, including appropriate restriction sites, is synthesized by DNA 2.0 (Menlo Park, Calif., USA). The gene sequence is codon pair optimized for expression in *S. cerevisiae* as disclosed in patent application WO2008/000632. The synthetic gene is under control of (or operable linked to) a promoter from *S. cerevisiae*, i.e. the TDH3-promoter controls the expression of the FRDg-gene. Proper termination is controlled by a terminator sequence from *S. cerevisiae*, i.e. the TAL1-terminator. Primer sequences described in SEQ ID NO: 58 and SEQ ID NO: 59 are used to generate PCR fragment 119 consisting of the 3' INT1 integration site, using genomic DNA of strain CEN.PK 113-7D as template.

PCR fragments 116 to 119 are purified using the DNA Clean & Concentrator™-25 kit (Zymo Research, Irvine, Calif., USA) according to manufacturer's instructions.

Transformation of SUC-1029

Yeast transformation is performed by a method known by persons skilled in the art. *S. cerevisiae* strain SUC-1029 (Example 1) is transformed with purified PCR fragments 116 to 119. PCR fragments 117 and 118 contain overlaps at their 5' and 3' ends and PCR fragments 116 and 119 contain overlaps at their 3' and 5' end respectively, such that this allows homologous recombination of all four PCR fragments. The 5' end of PCR fragment 116 and the 3' end of PCR fragment 119 are homologous to the INT1 locus and enables integration of all four PCR fragments in the INT1 locus (see FIG. 6). This results in one linear fragment consisting of PCR fragments 116 to 119 integrated in the INT1 locus. This method of integration is described in patent application WO2013076280. The INT1 locus is located at chromosome XV, 659 bp downstream of YOR071c and 998 bp upstream of YOR070c. This approach results in expression of the fumarate reductase protein of 1139 amino acids as indicated in SEQ ID NO: 8, which lacks the C-terminal amino acid SKI as compared to the native sequence from *T. brucei*.

Transformation mixtures are plated on YEPh-agar (per liter: 10 grams yeast extract, 20 grams PhytonePeptone, 20 grams galactose, 20 grams agar)) containing 100 μg nourseothricin (Jena Bioscience, Germany) per ml. After three days of growth at 30° C., individual transformants are re-streaked on YEPh-agar plates containing 20 grams galactose per liter and 100 μg nourseothricin per ml. Presence of the introduced genes is confirmed by using PCR using primer sequences that can anneal to the coding sequences of the ORF's encoded by SEQ ID NO: 38 and SEQ ID NO: 62.

Example 7: Transformation of Genes Encoding Malate Dehydrogenase Mutants to Strain REV-0001 and Production of Succinic Acid in Resulting Transformants In order to determine if succinate levels are increased in strains expressing MDH mutants, MDH mutants are introduced in strain REV-0001 in which FRDg is expressed (Example 6). Based on the malic acid production results (Example 4) and the in vitro activity assay results (Example 5), 3 MDH mutants are selected: MUT_014, MUT_015 and MUT_034.

Generation of PCR Fragments

The amplification of PCR fragment 1, 2, 3, 4 and 5 is described in Example 2. In order to introduce the wild-type and diverse MDH mutants, PCR fragment 120 (wild-type MDH3, SEQ ID NO: 31), fragment 121 (MUT_014, SEQ ID NO: 64), fragment 122 (MUT_015, SEQ ID NO: 65) or fragment 123 (MUT_034, SEQ ID NO: 66) are used. The wild-type and mutant MDH3 genes are driven by the *S. cerevisiae* TDH3 terminator and termination is controlled by the *S. cerevisiae* GPM1 terminator. The cassettes are amplified by PCR using the primer sequences described in SEQ ID NO: 19 and SEQ ID NO: 20, to generate PCR fragments 120 to 123.

Primer sequences described in SEQ ID NO: 63 and SEQ ID NO: 41 are used to generate PCR fragment 124 consisting of the 3' INT59 integration site, using genomic DNA of strain CEN.PK 113-7D as template.

PCR fragments 1 to 5/120-123 and PCR fragment 124 are purified using the DNA Clean & Concentrator™-25 kit (Zymo Research, Irvine, Calif., USA) according to manufacturer's instructions.

Transformation to REV-0001

Yeast transformation is performed by a method known by persons skilled in the art. *S. cerevisiae* strain REV-0001 is transformed with purified PCR fragments 1 to 5 and 124 in combination with PCR fragments 120, 121, 122 or 123. PCR fragments 2 to 5/120-123 contain overlaps at their 5' and 3' ends and PCR fragments 1 and 124 at their 3' and 5' end respectively, such that this allows homologous recombination of all seven PCR fragments. The 5' end of PCR fragment 1 and the 3' end of PCR fragment 124 are homologous to the INT59 locus and enable integration of all seven PCR fragments in the INT59 locus (see FIG. 7). This results in one linear fragment consisting of PCR fragments 2 to 5/120-123 integrated in the INT59 locus. This method of integration is described in patent application WO2013076280. The INT59 locus is located at chromosome XI, 923 bp downstream of YKR092C and 922 bp upstream of YKR093W. Transformation mixtures are plated on YEPh-agar (per liter: 10 grams yeast extract, 20 grams PhytonePeptone, 20 grams agar) containing 20 grams galactose per liter and 200 μg G418 (Sigma Aldrich, Zwijndrecht, The Netherlands) per ml. After three days of growth at 30° C., individual transformants are re-streaked on YEPh-agar plates containing 20 grams galactose per liter and 200 μg G418 per ml. Presence of all introduced genes is confirmed by PCR.

Dicarboxylic Acid Production

To determine dicarboxylic acid production, REV-0001-derived transformants expressing the succinic acid production pathway with either wild-type MDH3 or individual MDH mutants are grown in micro titer plates and dicarboxylic acid concentrations are determined as described in General Materials and Methods.

Succinic acid titers of strains expressing MUT_014, MUT_015 and MUT_34 are respectively 1.3-, 1.2 and 1.4-fold higher than strains expressing MDH3, indicating that succinic acid production is also improved in strains expressing MDH mutants.

The invention claimed is:

1. A recombinant yeast host cell which is capable of producing a dicarboxylic acid and which comprises a nucleic acid sequence encoding a mutant polypeptide having malate dehydrogenase activity, wherein the mutant polypeptide comprises an amino acid sequence which, when aligned with the malate dehydrogenase comprising the sequence set out in SEQ ID NO: 39, comprises a mutation of an amino acid residue corresponding to amino acid 34 in SEQ ID NO: 39, wherein the polypeptide has at least 60% sequence identity with SEQ ID NO: 39; and, wherein the mutant polypeptide has an increase in the NADP(H)- relative to NAD(H)-dependent activity as compared to that of a reference polypeptide having NAD(H)-dependent malate dehydrogenase activity (EC 1.1.1.37), and wherein the reference polypeptide has an aspartic acid (D) at amino acid 34.

2. The recombinant host cell according to claim 1, wherein the mutation of the amino acid residue corresponding to amino acid 34 in SEQ ID NO: 39 is a substitution to a small amino acid.

3. The recombinant host cell according to claim 1, wherein the mutation of the amino acid residue corresponding to amino acid 34 in SEQ ID NO: 39 is selected from the group of substitutions corresponding to 34G and 34S.

4. The recombinant host cell according to claim 1, wherein the mutant polypeptide having malate dehydrogenase activity further comprises a mutation of an amino acid residue corresponding to amino acid 36 in SEQ ID NO: 39.

5. The recombinant host cell according to claim 4, wherein the mutation of the amino acid residue corresponding to amino acid 36 in SEQ ID NO: 39 is selected from the group of substitutions corresponding to 36R, 36Q, 36A, 36E, 36P and 36S.

6. The recombinant host cell according to claim 1, wherein the amino acid residue corresponding to amino acid 34 in SEQ ID NO: 39 is selected from glycine (G) or serine (S).

7. The recombinant host cell according to claim 1, wherein the NAD(H)- and NADP(H)-dependent activities of the mutant polypeptide having malate dehydrogenase activity are both increased.

8. The recombinant host cell according to claim 1, wherein the mutant polypeptide having malate dehydrogenase activity is a mutant NAD(H)-dependent malate dehydrogenase (EC 1.1.1.37).

9. The recombinant host cell according to claim 1, wherein the mutant polypeptide having malate dehydrogenase activity is a mutant peroxisomal NAD(H)-dependent malate dehydrogenase.

10. The recombinant host cell according to claim 1, wherein the mutant polypeptide having malate dehydrogenase activity is a mutant of a homologous polypeptide having malate dehydrogenase activity.

11. The recombinant host cell according to claim 1, wherein the mutant polypeptide having malate dehydrogenase activity is a mutant NAD(H)-dependent malate dehydrogenase from a yeast.

12. The recombinant yeast host cell according to claim 1, which is selected from the group consisting of *Candida, Hansenula, Kluyveromyces, Pichia, Issatchenkia, Saccharomyces, Schizosaccharomyces*, or *Yarrowia* strains.

13. The recombinant host cell according to claim 12, wherein the yeast cell is *Saccharomyces cerevisiae*.

14. The recombinant host cell according to claim 1, wherein the nucleic sequence encoding the mutant polypeptide having malate dehydrogenase activity is expressed in the cytosol and the mutant polypeptide having malate dehydrogenase activity is active in the cytosol.

15. The host cell according to claim 1, wherein the recombinant host cell further comprises one or more copies of a nucleic acid encoding one or more of a phosphoenolpyruvate carboxykinase, a phosphoenolpyruvate carboxylase, a pyruvate carboxylase, a fumarase, a fumarate reductase and/or a succinate transporter.

16. A method for production of a dicarboxylic acid, wherein the method comprises fermenting the recombinant host cell according to claim 1 under conditions suitable for production of the dicarboxylic acid.

17. The method according to claim 16, further comprising recovering the dicarboxylic acid from the fermentation medium.

18. The method according to claim 16, wherein the dicarboxylic acid is succinic acid, malic acid and/or fumaric acid.

* * * * *

SEQUENCE LISTING

```
<160> NUMBER OF SEQ ID NOS: 67

<210> SEQ ID NO 1
<211> LENGTH: 10504
<212> TYPE: DNA
<213> ORGANISM: Artificial Sequence
<220> FEATURE:
<223> OTHER INFORMATION: nucleotide sequence of fragment 2 (Figure 2),
      which includes PEP carboxykinase from Actinobacillus succinogenes
      codon pair optimized for expression in Saccharomyces cerevisiae

<400> SEQUENCE: 1
ttgcccatcg aacgtacaag tactcctctg ttctctcctt cctttgcttt gtgcgacacc        60
taactacata gtgtttaaag attacggata tttaacttac ttagaataat gccattttt       120
```

-continued

```
tgagttataa taatcctacg ttagtgtgag cgggatttaa actgtgagga ccttaataca      180
ttcagacact tctgcggtat caccctactt attcccttcg agattatatc taggaaccca      240
tcaggttggt ggaagattac ccgttctaag acttttcagc ttcctctatt gatgttacac      300
ctggacaccc cttttctggc atccagtttt taatcttcag tggcatgtga gattctccga      360
aattaattaa agcaatcaca caattctctc ggataccacc tcggttgaaa ctgacaggtg      420
gtttgttacg catgctaatg caaaggagcc tatatacctt tggctcggct gctgtaacag      480
ggaatataaa gggcagcata atttaggagt ttagtgaact tgcaacattt actattttcc      540
cttcttacgt aaatattttt ctttttaatt ctaaatcaat ctttttcaat tttttgtttg      600
tattcttttc ttgcttaaat ctataactac aaaaaacaca tacataaact aaaaatgact      660
gatttgaaca aattggtcaa ggaattgaat gatttgggtt tgactgacgt caaggaaatt      720
gtctacaacc catcttacga acaattattc gaagaagaaa ccaagccagg tttggaaggt      780
ttcgacaagg gtactttgac cactttaggt gctgttgctg ttgacaccgg tатttттcacc      840
ggtcgttctc caaaggacaa atacattgtt tgtgatgaaa ccaccaagga caccgtctgg      900
tggaactctg aagctgccaa gaacgataac aagccaatga ctcaagaaac ctggaaatct      960
ttgagagaat tggttgccaa gcaattgtct ggtaagagat tattcgttgt tgacgctttc     1020
tgtggtgctt ctgaaaagca cagaattggt gtcagaatgg tcactgaagt tgcttggcaa     1080
gctcatttcg tcaagaacat gttcatcaga ccaactgacg aagaattgaa gaacttcaag     1140
gctgacttca ccgttttgaa tggtgccaag tgtaccaacc caaactggaa ggaacaaggt     1200
ttgaactctg aaaactttgt tgctttcaac atcactgaag gtatccaatt gattggtggt     1260
acttggtacg gtggtgaaat gaagaagggt atgttctcca tgatgaacta tttcttgcca     1320
ttgaaaggtg ttgcttccat gcactgttct gccaatgtcg gtaaggatgg tgacgttgcc     1380
atcttcttcg gtctatccgg tactggtaag accactctat ccactgaccc aaagagacaa     1440
ttgattggta tgacgaaca cggttgggac gaatctggtg tctttaactt tgaaggtggt     1500
tgttacgcca agaccatcaa cttatctcaa gaaaacgaac cagatatcta cggtgccatc     1560
cgtcgtgatg ctttgttgga aaacgttgtt gtcagagctg acggttctgt tgacttcgac     1620
gacggttcca agactgaaaa caccagagtt tcttacccaa tctaccacat tgacaacatt     1680
gtcagacctg tttccaaggc tggtcacgct accaaggtta tcttcttgac tgctgatgct     1740
ttcggtgtct tgccacctgt ttccaaattg actccagaac aaaccgaata ctacttcttg     1800
tccggtttca ctgccaaatt ggctggtact gaaagaggtg tcactgaacc aactccaact     1860
ttctctgctt gtttcggtgc tgctttctta tctttgcacc caatccaata cgctgatgtc     1920
ttggttgaaa gatgaaggc ttctggtgct gaagcttact ggtcaacac cggttggaac     1980
ggtactggta agagaatctc catcaaggat accagaggta tcattgatgc tatcttggac     2040
ggttccattg aaaaggctga atgggtgaa ttgccaatct tcaacttggc cattccaaag     2100
gctttgccag tgttgacccc agccatctta gatccaagag acacctacgc tgacaaggct     2160
caatggcaag tcaaggctga agatttggct aacagattcg tcaagaactt tgtcaaatac     2220
actgctaacc cagaagctgc caaattgttt ggtgctggtc caaaggctta aaggagttaa     2280
aggcaaagtt ttcttttcta gagccgttcc cacaaataat tatacgtata tgcttctttt     2340
cgtttactat atatctatat ttacaagcct ttattcactg atgcaatttg ttttccaata     2400
cttttttgga gatctcataa ctagatatca tgatggcgca acttggcgct atcttaatta     2460
ctctggctgc caggcccgtg tagagggccg caagaccttc tgtacgccat atagtctcta     2520
```

```
agaacttgaa caagtttcta gacctattgc cgcctttcgg atcgctattg ttcctccgga   2580
tcgatgtaca caaccgactg cacccaaacg aacacaaatc ttagcattgc ccatcgaacg   2640
tacaagtact cctctgttct ctccttcctt tgctttgtgc gacacctaac tacatagtgt   2700
ttaaagatta cggatattta acttactag aataatgcca ttttttttgag ttataataat   2760 cctacgttag tgtgagcggg atttaaactg tgaggacctt aatacattca gacacttctg   2820
cggtatcacc ctacttattc ccttcgagat tatatctagg aacccatcag gttggtggaa   2880
gattacccgt tctaagactt ttcagcttcc tctattgatg ttacacctgg acacccttt    2940 tctggcatcc agtttttaat cttcagtggc atgtgagatt ctccgaaatt aattaaagca   3000
atcacacaat tctctcggat accacctcgg ttgaaactga caggtggttt gttacgcatg   3060
ctaatgcaaa ggagcctata tacctttggc tcggctgctg taacagggaa tataaagggc   3120
agcataattt aggagtttag tgaacttgca acatttacta ttttcccttc ttacgtaaat   3180 attttttcttt ttaattctaa atcaatcttt ttcaattttt tgtttgtatt cttttcttgc   3240
ttaaatctat aactacaaaa aacacataca taaactaaaa atgactgatt tgaacaaatt   3300
ggtcaaggaa ttgaatgatt tgggtttgac tgacgtcaag gaaattgtct acaacccatc   3360
ttacgaacaa ttattcgaag aagaaaccaa gccaggtttg gaaggtttcg acaagggtac   3420
tttgaccact ttaggtgctg ttgctgttga caccggtatt ttcaccggtc gttctccaaa   3480
ggacaaatac attgtttgtg atgaaaccac caaggacacc gtctggtgga actctgaagc   3540
tgccaagaac gataacaagc caatgactca agaaacctgg aaatctttga gagaattggt   3600
tgccaagcaa ttgtctggta agagattatt cgttgttgac gctttctgtg gtgcttctga   3660
aaagcacaga attggtgtca gaatggtcac tgaagttgct tggcaagctc atttcgtcaa   3720
gaacatgttc atcagaccaa ctgacgaaga attgaagaac ttcaaggctg acttcaccgt   3780
tttgaatggt gccaagtgta ccaacccaaa ctggaaggaa caaggtttga actctgaaaa   3840 cttttgttgct ttcaacatca ctgaaggtat ccaattgatt ggtggtactt ggtacggtgg   3900
tgaaatgaag aagggtatgt tctccatgat gaactatttc ttgccattga aaggtgttgc   3960
ttccatgcac tgttctgcca atgtcggtaa ggatggtgac gttgccatct tcttcggtct   4020
atccggtact ggtaagacca ctctatccac tgacccaaag agacaattga ttggtgatga   4080
cgaacacggt tgggacgaat ctggtgtctt aacttttgaa ggtggttgtt acgccaagac   4140
catcaactta tctcaagaaa acgaaccaga tatctacggt gccatccgtc gtgatgcttt   4200
gttggaaaac gttgttgtca gagctgacgg ttctgttgac ttcgacgacg gttccaagac   4260
tgaaaacacc agagtttctt acccaatcta ccacattgac aacattgtca gacctgtttc   4320
caaggctggt cacgctacca agttatcttc ttgactgct gatgctttcg gtgtcttgcc   4380 acctgttttcc aaattgactc cagaacaaac cgaatactac ttcttgtccg gtttcactgc   4440
caaattggct ggtactgaaa gaggtgtcac tgaaccaact ccaactttct ctgcttgttt   4500
cggtgctgct ttcttatctt tgcacccaat ccaatacgct gatgtcttgg ttgaaagaat   4560
gaaggcttct ggtgctgaag cttacttggt caacaccggt tggaacggta ctggtaagag   4620
aatctccatc aaggatacca gaggtatcat tgatgctatc ttggacggtt ccattgaaaa   4680
ggctgaaatg ggtgaattgc caatcttcaa cttggccatt ccaaaggctt gccaggtgt    4740 tgacccagcc atcttagatc caagagacac ctacgctgac aaggctcaat ggcaagtcaa   4800
ggctgaagat ttggctaaca gattcgtcaa gaactttgtc aaatacactg ctaacccaga   4860
```

```
agctgccaaa ttggttggtg ctggtccaaa ggcttaaagg agttaaaggc aaagttttct    4920
tttctagagc cgttcccaca ataattata cgtatatgct tcttttcgtt tactatatat     4980
ctatatttac aagcctttat tcactgatgc aatttgtttc caaatacttt tttggagatc    5040
tcataactag atatcatgat ggcgcaactt ggcgctatct taattactct ggctgccagg    5100
cccgtgtaga gggccgcaag accttctgta cgccatatag tctctaagaa cttgaacaag    5160
tttctagacc tattgccgcc tttcggatcg ctattgttcc tccggatcga tgtacacaac    5220
cgactgcacc caaacgaaca caaatcttag cattgcccat cgaacgtaca agtactcctc    5280
tgttctctcc ttcctttgct tgtgcgaca cctaactaca tagtgtttaa agattacgga     5340
tatttaactt acttagaata atgccatttt tttgagttat aataatccta cgttagtgtg    5400
agcgggattt aaactgtgag gaccttaata cattcagaca cttctgcggt atcaccctac    5460
ttattccctt cgagattata tctaggaacc catcaggttg gtggaagatt acccgttcta    5520
agacttttca gcttcctcta ttgatgttac acctggacac cccttttctg gcatccagtt    5580
tttaatcttc agtggcatgt gagattctcc gaaattaatt aaagcaatca cacaattctc    5640
tcggatacca cctcggttga aactgacagg tggtttgtta cgcatgctaa tgcaaaggag    5700
cctatatacc tttggctcgg ctgctgtaac agggaatata aagggcagca taatttagga    5760
gtttagtgaa cttgcaacat ttactatttt cccttcttac gtaaatattt ttcttttaa     5820 ttctaaatca atcttttca atttttgtt tgtattcttt tcttgcttaa atctataact      5880
acaaaaaaca catacataaa ctaaaaatga ctgatttgaa caaattggtc aaggaattga    5940
atgatttggg tttgactgac gtcaaggaaa ttgtctacaa cccatcttac gaacaattat    6000
tcgaagaaga aaccaagcca ggtttggaag gtttcgacaa gggtactttg accactttag    6060
gtgctgttgc tgttgacacc ggtattttca ccggtcgttc tccaaaggac aaatacattg    6120
tttgtgatga aaccaccaag gacaccgtct ggtggaactc tgaagctgcc aagaacgata    6180
acaagccaat gactcaagaa acctggaaat ctttgagaga attggttgcc aagcaattgt    6240
ctggtaagag attattcgtt gttgacgctt tctgtggtgc ttctgaaaag cacagaattg    6300
gtgtcagaat ggtcactgaa gttgcttggc aagctcattt cgtcaagaac atgttcatca    6360
gaccaactga cgaagaattg aagaacttca aggctgactt caccgttttg aatggtgcca    6420
agtgtaccaa cccaaactgg aaggaacaag gtttgaactc tgaaaacttt gttgctttca    6480
acatcactga aggtatccaa ttgattggtg gtacttggta cggtggtgaa atgaagaagg    6540
gtatgttctc catgatgaac tatttcttgc cattgaaagg tgttgcttcc atgcactgtt    6600
ctgccaatgt cggtaaggat ggtgacgttg ccatcttctt cggtctatcc ggtactggta    6660
agaccactct atccactgac ccaaagagac aattgattgg tgatgacgaa cacgttgggg    6720
acgaatctgg tgtcttaac tttgaaggtg gttgttacgc caagaccatc aacttatctc     6780 aagaaacga accagatatc tacggtgcca tccgtcgtga tgctttgttg gaaaacgttg     6840
ttgtcagagc tgacggttct gttgacttcg acgacggttc caagactgaa acaccagag     6900 tttcttaccc aatctaccac attgacaaca ttgtcagacc tgtttccaag gctggtcacg    6960
ctaccaaggt tatcttcttg actgctgatg ctttcggtgt cttgccacct gtttccaaat    7020
tgactccaga acaaaccgaa tactacttct tgtccggttt cactgccaaa ttggctggta    7080
ctgaaagagg tgtcactgaa ccaactccaa cttctctgc ttgtttcggt gctgctttct     7140
tatctttgca cccaatccaa tacgctgatg tcttggttga aagaatgaag gcttctggtg    7200
ctgaagctta cttggtcaac accggttgga acggtactgg taagagaatc tccatcaagg    7260
```

```
ataccagagg tatcattgat gctatcttgg acggttccat tgaaaaggct gaaatgggtg    7320
aattgccaat cttcaacttg gccattccaa aggctttgcc aggtgttgac ccagccatct    7380
tagatccaag agacacctac gctgacaagg ctcaatggca agtcaaggct gaagatttgg    7440
ctaacagatt cgtcaagaac tttgtcaaat acactgctaa cccagaagct gccaaattgg    7500
ttggtgctgg tccaaaggct taaggagtt aaaggcaaag ttttcttttc tagagccgtt     7560
cccacaaata attatacgta tatgcttctt ttcgtttact atatatctat atttacaagc    7620
ctttattcac tgatgcaatt tgtttccaaa tactttttg gagatctcat aactagatat     7680
catgatggcg caacttggcg ctatcttaat tactctggct gccaggcccg tgtagagggc    7740
cgcaagacct tctgtacgcc atatagtctc taagaacttg aacaagtttc tagacctatt    7800
gccgcctttc ggatcgctat tgttcctccg gatcgatgta cacaaccgac tgcacccaaa    7860
cgaacacaaa tcttagcatt gcccatcgaa cgtacaagta ctcctctgtt ctctccttcc    7920
tttgctttgt gcgacaccta actacatagt gtttaaagat tacggatatt taacttactt    7980
agaataatgc cattttttg agttataata atcctacgtt agtgtgagcg ggatttaaac     8040
tgtgaggacc ttaatacatt cagacacttc tgcggtatca ccctacttat tcccttcgag    8100
attatatcta ggaacccatc aggttggtgg aagattaccc gttctaagac ttttcagctt    8160
cctctattga tgttacacct ggacacccct tttctggcat ccagttttta atcttcagtg    8220
gcatgtgaga ttctccgaaa ttaattaaag caatcacaca attctctcgg ataccacctc    8280
ggttgaaact gacaggtggt tgttacgca tgctaatgca aaggagccta tacctttg       8340 gctcggctgc tgtaacaggg aatataaagg gcagcataat ttaggagttt agtgaacttg    8400
caacatttac tattttccct tcttacgtaa atatttttct ttttaattct aaatcaatct    8460
ttttcaattt tttgtttgta ttcttttctt gcttaaatct ataactacaa aaaacacata    8520
cataaactaa aaatgactga tttgaacaaa ttggtcaagg aattgaatga tttgggtttg    8580
actgacgtca aggaaattgt ctacaaccca tcttacgaac aattattcga agaagaaacc    8640
aagccaggtt tggaaggttt cgacaagggt actttgacca ctttaggtgc tgttgctgtt    8700
gacaccggta ttttcaccgg tcgttctcca aggacaaat acattgtttg tgatgaaacc     8760
accaaggaca ccgtctggtg gaactctgaa gctgccaaga acgataacaa gccaatgact    8820
caagaaacct ggaaatcttt gagagaattg gttgccaagc aattgtctgg taagagatta    8880
ttcgttgttg acgctttctg tggtgcttct gaaaagcaca gaattggtgt cagaatggtc    8940
actgaagttg cttggcaagc tcatttcgtc aagaacatgt tcatcagacc aactgacgaa    9000
gaattgaaga acttcaaggc tgacttcacc gttttgaatg gtgccaagtg taccaaccca    9060
aactggaagg aacaaggttt gaactctgaa aactttgttg ctttcaacat cactgaaggt    9120
atccaattga ttggtggtac ttggtacggt ggtgaaatga agaagggtat gttctccatg    9180
atgaactatt tcttgccatt gaaaggtgtt gcttccatgc actgttctgc caatgtcggt    9240
aaggatggtg acgttgccat cttcttcggt ctatccggta ctggtaagac cactctatcc    9300
actgacccaa agagacaatt gattggtgat gacgaacacg gttgggacga atctggtgtc    9360
tttaactttg aaggtggttg ttacgccaag accatcaact tatctcaaga aaacgaacca    9420
gatatctacg gtgccatccg tcgtgatgct tgttggaaa cgttgttgt cagagctgac     9480 ggttctgttg acttcgacga cggttccaag actgaaaaca ccagagtttc ttacccaatc    9540
taccacattg acaacattgt cagacctgtt tccaaggctg gtcacgctac caaggttatc    9600
```

-continued

| | |
|---|---|
| ttcttgactg ctgatgcttt cggtgtcttg ccacctgttt ccaaattgac tccagaacaa | 9660 |
| accgaatact acttcttgtc cggtttcact gccaaattgg ctggtactga aagaggtgtc | 9720 |
| actgaaccaa ctccaacttt tctctgcttgt ttcggtgctg ctttcttatc tttgcaccca | 9780 |
| atccaatacg ctgatgtctt ggttgaaaga atgaaggctt ctggtgctga agcttacttg | 9840 |
| gtcaacaccg gttggaacgg tactggtaag agaatctcca tcaaggatac cagaggtatc | 9900 |
| attgatgcta tcttggacgg ttccattgaa aaggctgaaa tgggtgaatt gccaatcttc | 9960 |
| aacttggcca ttccaaaggc tttgccaggt gttgacccag ccatcttaga tccaagagac | 10020 |
| acctacgctg acaaggctca atggcaagtc aaggctgaag atttggctaa cagattcgtc | 10080 |
| aagaactttg tcaaatacac tgctaaccca gaagctgcca aattggttgg tgctggtcca | 10140 |
| aaggcttaaa ggagttaaag gcaaagtttt cttttctaga gccgttccca caaataatta | 10200 |
| tacgtatatg cttcttttcg tttactatat atctatattt acaagccttt attcactgat | 10260 |
| gcaatttgtt tccaaatact ttttggaga tctcataact agatatcatg atggcgcaac | 10320 |
| ttggcgctat cttaattact ctggctgcca ggcccgtgta gagggccgca agaccttctg | 10380 |
| tacgccatat agtctctaag aacttgaaca agtttctaga cctattgccg cctttcggat | 10440 |
| cgctattgtt cctccggatc gatgtacaca accgactgca cccaaacgaa cacaaatctt | 10500 |
| agca | 10504 |

<210> SEQ ID NO 2
<211> LENGTH: 4552
<212> TYPE: DNA
<213> ORGANISM: Artificial Sequence
<220> FEATURE:
<223> OTHER INFORMATION: nucleotide sequence of fragment 3 (Figure 2), which includes pyruvate carboxylase (PYC2) from S. cerevisiae codon pair optimized for expression in S. cerevisiae

<400> SEQUENCE: 2

| | |
|---|---|
| cggatcgatg tacacaaccg actgcaccca aacgaacaca atcttagca gtgcgggcca | 60 |
| gaaaaaggaa gtgtttccct ccttcttgaa ttgatgttac cctcataaag cacgtggcct | 120 |
| cttatcgaga aagaaattac cgtcgctcgt gatttgtttg caaaaagaac aaaactgaaa | 180 |
| aaacccagac acgctcgact tcctgtcttc ctattgattg cagcttccaa tttcgtcaca | 240 |
| caacaaggtc ctagcgacgg ctcacaggtt ttgtaacaag caatcgaagg ttctggaatg | 300 |
| gcgggaaagg gtttagtacc acatgctatg atgcccactg tgatctccag agcaaagttc | 360 |
| gttcgatcgt actgttactc tctctctttc aaacagaatt gtccgaatcg tgtgacaaca | 420 |
| acagcctgtt ctcacacact cttttcttct aaccaagggg gtggtttagt ttagtagaac | 480 |
| ctcgtgaaac ttacatttac atatatataa acttgcataa attggtcaat gcaagaaata | 540 |
| catatttggt cttttctaat tcgtagtttt tcaagttctt agatgctttc ttttctctt | 600 |
| ttttacagat catcaaggaa gtaattatct actttttaca acaaatataa acaatgtcc | 660 |
| tcttccaaga tcttggctgg tttgagagac aacttttctt tgttgggtga aaagaacaag | 720 |
| attttggtcg ccaacagagg tgaaatccca atcagaattt tcagatctgc tcacgaattg | 780 |
| tctatgagaa ctatcgccat ctactctcac gaagatagat tatccatgca cagattgaag | 840 |
| gctgatgaag cctacgttat cggtgaagaa ggtcaataca ccccagtcgg tgcttacttg | 900 |
| gccatggacg aaatcatcga aattgccaag aagcacaagg tcgatttcat ccacccaggt | 960 |
| tacggttct tgtctgaaaa actctgaattt gctgacaagg ttgttaaggc tggtattacc | 1020 |
| tggattggtc caccagctga agtcattgaa tctgttggtg acaaggtttc tgccagacat | 1080 |

```
ttggctgctc gtgccaacgt tccaactgtc ccaggtactc caggtcctat cgaaaccgtt    1140
caagaagctc tagatttcgt caatgaatac ggttacccag ttatcatcaa ggctgctttc    1200
ggtggtggtg gtcgtggtat gagagttgtc agagaaggtg acgatgtcgc tgatgctttc    1260
caaagagcca cttctgaagc tagaactgct ttcggtaacg gtacttgttt cgtcgaaaga    1320
ttcttggaca agccaaagca cattgaagtt caattattag ctgacaacca cggtaacgtt    1380
gtccacttgt tcgaaagaga ctgttccgtc caaagacgtc accaaaaggt tgtcgaagtt    1440
gctccagcta agactttacc aagagaagtt agagatgcta tcttgaccga tgccgttaag    1500
ttggctaagg tttgtggtta cagaaacgct ggtactgctg aattcttggt tgacaaccaa    1560
aacagacatt acttcattga aatcaaccca agaattcaag tcgaacacac catcactgaa    1620
gaaatcactg gtattgacat tgtctccgct caaatccaaa tcgccgctgg tgctactttg    1680
actcaattag gtctattaca agacaaaatc accaccagag gtttctctat ccaatgtcgt    1740
atcaccactg aagatccatc caagaacttc caaccagaca ctggtcgttt ggaagtctac    1800
agatccgctg gtggtaacgg tgtcagattg gacggtggta acgcctacgc tggtgctacc    1860
atctctccac actacgactc catgttggtt aagtgttcct gttctggttc tacctacgaa    1920
attgtcagaa gaaagatgat cagagctttg attgaattca gaatcagagg tgtcaagacc    1980
aacatcccat tcttgttgac tttgttgacc aacccagttt tcattgaagg tacctactgg    2040
accactttca tcgatgacac tccacaattg ttccaaatgg tttcctctca aaacagagct    2100
caaaaattgt tgcactactt ggctgacttg gccgtcaacg ttcctctat caagggtcaa    2160 atcggtttac caaagttgaa gtccaaccct tccgttccac atttgcacga tgctcaaggt    2220
aatgtcatca acgttaccaa atctgcccca ccatccggtt ggagacaagt cttgttggaa    2280
aagggtccat ccgaatttgc caagcaagtc agacaattca acggtacttt gttgatggac    2340
accacctgga gagatgctca ccaatctttg ctagctacca gagtcagaac tcacgatttg    2400
gccaccattg ctccaaccac tgctcacgct ttggctggtg cctttgcttt ggaatgttgg    2460
ggtggtgcta ctttcgatgt cgccatgaga ttcttgcatg aggacccatg gaaagattg    2520 agaaaattga gatctttggt cccaaacatt ccattccaaa tgttgttgag aggtgctaac    2580
ggtgttgctt actcctcttt gccagacaac gccattgacc atttcgttaa gcaagccaag    2640
gacaatggtg ttgacatttt cagagtcttt gacgctttga cgacttgga acaattgaag    2700 gttggtgtta atgctgtcaa gaaggctggt ggtgttgtcg aagctaccgt tgttactct    2760 ggtgacatgt tgcaaccagg taagaaatac aacttggact actacttaga agttgtcgaa    2820
aagatcgttc aaatgggtac tcacatcttg ggtatcaagg acatggctgg taccatgaag    2880
ccagctgctg ccaaattgtt gattggttct ttacgtacca gatacccaga cttgccaatc    2940
cacgttcact ctcatgactc cgctggtact gctgttgctt ccatgactgc ttgtgctttg    3000
gccggtgctg atgttgttga cgttgccatt aactccatgt ccggtttgac ctctcaacca    3060
tctattaacg ctttgttggc ctccttggaa ggtaacattg acactggtat caacgtcgaa    3120
cacgttagag aattggacgc ttactgggct gaaatgagat tattatactc ttgtttcgaa    3180
gctgacttga agggtccaga ccctgaagtt taccaacacg aaattccagg tggtcaattg    3240
accaacttgt tgttccaagc tcaacaatta ggtctaggtg aacaatgggc tgaaaccaag    3300
agagcttaca gagaagctaa ctacttgttg ggtgacattg ttaaggtcac cccaacttct    3360
aaggtcgttg gtgatttggc tcaattcatg gttctaacaa aattgacttc tgatgacatc    3420
```

```
agaagattag ctaactcttt ggacttccca gactccgtta tggacttctt cgaaggtttg      3480
atcggtcaac catacggtgg tttcccagaa ccattgagat ccgatgtttt gagaaacaag      3540
cgtcgtaaat tgacttgtag accaggttta gaattggaac cattcgattt ggaaaagatc      3600
agagaagatt tgcaaaacag attcggtgat atcgatgaat gtgatgttgc ctcctacaac      3660
atgtatcctc gtgtctacga agatttccaa aagattagag aaacttacgg tgacttgtct      3720
gtcttaccaa ccaagaactt cttggctcca gctgaaccag acgaagaaat cgaagtcacc      3780
attgaacaag gtaagacttt gattatcaaa ttacaagctg ttggtgattt gaacaagaaa      3840
accggtcaaa gagaagtcta cttcgaattg aacggtgaat tgagaaagat cagagttgct      3900
gacaaatctc aaaacattca atctgttgcc aagccaaagg ctgatgtcca cgacacccac      3960
caaatcggtg ctccaatggc tggtgtcatc attgaagtca aggttcacaa gggttctttg      4020
gtcaagaagg gtgaatctat cgccgttttg tctgctatga agatggaaat ggttgtttcc      4080
tctccagctg atggtcaagt caaagatgtc tttatccgtg acggtgaatc cgtcgatgct      4140
tctgacttgt tggttgtttt ggaagaagaa actctaccac cttctcaaaa gaaataaagc      4200
gaatttctta tgatttatga ttttattat taaataagtt ataaaaaaaa taagtgtata      4260
caaattttaa agtgactctt aggttttaaa acgaaaattc ttattcttga gtaactcttt      4320
cctgtaggtc aggttgcttt ctcaggtata gcatgaggtc gctcttattg accacacctc      4380
taccggcatg ccgagcaaat gcctgcaaat cgctccccat ttcacccaat gtagatatg       4440 ctaactccag caatgagttg atgaatctcg gtgtgtattt tatgtcctca gaggacaacc      4500
tcacgctttc cggcatcttc cagaccacag tatatccatc cgcctcctgt tg              4552
```

<210> SEQ ID NO 3
<211> LENGTH: 1572
<212> TYPE: DNA
<213> ORGANISM: Artificial Sequence
<220> FEATURE:
<223> OTHER INFORMATION: nucleotide sequence of the PCR template for
      fragment 4 (Figure 2), which includes a KanMX selection marker
      functional in S. cerevisiae

<400> SEQUENCE: 3

```
tcgtacgctg caggtcgacg aattctaccg ttcgtataat gtatgctata cgaagttata        60
gatctgttta gcttgcctcg tccccgccgg gtcacccggc cagcgacatg gaggcccaga       120
ataccctcct tgacagtctt gacgtgcgca gctcaggggc atgatgtgac tgtcgcccgt       180
acatttagcc catacatccc catgtataat catttgcatc catacatttt gatggccgca       240
cggcgcgaag caaaaattac ggctcctcgc tgcagacctg cgagcaggga acgctcccc       300 tcacagacgc gttgaattgt ccccacgccg cgcccctgta gagaaatata aaggttagg       360 atttgccact gaggttcttc tttcatatac ttcctttaa aatcttgcta ggatacagtt       420
ctcacatcac atccgaacat aaacaaccat gggtaaggaa aagactcacg tttcgaggcc       480
gcgattaaat tccaacatgg atgctgattt atatgggtat aaatgggctc gcgataatgt       540
cgggcaatca ggtgcgacaa tctatcgatt gtatgggaag cccgatgcgc cagagttgtt       600
tctgaaacat ggcaaaggta gcgttgccaa tgatgttaca gatgagatgg tcagactaaa       660
ctggctgacg gaatttatgc ctcttccgac catcaagcat tttatccgta ctcctgatga       720
tgcatggtta ctcaccactg cgatccccgg caaaacagca ttccaggtat tagaagaata       780
tcctgattca ggtgaaaata ttgttgatgc gctggcagtg ttcctgcgcc ggttgcattc       840
gattcctgtt tgtaattgtc cttttaacag cgatcgcgta tttcgtctcg ctcaggcgca       900
```

```
atcacgaatg aataacggtt tggttgatgc gagtgatttt gatgacgagc gtaatggctg    960
gcctgttgaa caagtctgga aagaaatgca taagcttttg ccattctcac cggattcagt   1020
cgtcactcat ggtgatttct cacttgataa ccttattttt gacgagggga aattaatagg   1080
ttgtattgat gttggacgag tcggaatcgc agaccgatac caggatcttg ccatcctatg   1140
gaactgcctc ggtgagtttt ctccttcatt acagaaacgg cttttttcaaa aatatggtat   1200 tgataatcct gatatgaata aattgcagtt tcatttgatg ctcgatgagt ttttctaatc   1260
agtactgaca ataaaaagat tcttgttttc aagaacttgt catttgtata gttttttat    1320 attgtagttg ttctatttta atcaaatgtt agcgtgattt ataTttttt tcgcctcgac    1380 atcatctgcc cagatgcgaa gttaagtgcg cagaaagtaa tatcatgcgt caatcgtatg   1440
tgaatgctgg tcgctatact gctgtcgatt cgatactaac gccgccatcc agtgtcgaaa   1500
acgagctcat aacttcgtat aatgtatgct atacgaacgg tagaattcga tatcagatcc   1560
actagtggcc ta                                                       1572
```

<210> SEQ ID NO 4
<211> LENGTH: 2260
<212> TYPE: DNA
<213> ORGANISM: Artificial Sequence
<220> FEATURE:
<223> OTHER INFORMATION: nucleotide sequence of fragment 5 (Figure 2), which includes a putative dicarboxylic acid transporter from Aspergillus niger codon pair optimized for expression in S. cerevisiae

<400> SEQUENCE: 4

```
aacgttgtcc aggtttgtat ccacgtgtgt ccgttccgcc aatattccgc gtgcccgcgg     60
aaccgccaga tattcattac ttgacgcaaa agcgtttgaa ataatgacga aaagaagga    120 agaaaaaaaa agaaaaatac cgcttctagg cgggttatct actgatccga gcttccacta   180
ggatagcacc caaacacctg catatttgga cgacctttac ttacaccacc aaaaaccact   240
ttcgcctctc ccgcccctga taacgtccac taattgagcg attacctgag cggtcctctt   300
ttgtttgcag catgagactt gcatactgca atcgtaagt agcaacgtgt caaggtcaaa    360
actgtatgga aaccttgtca cctcacttaa ttctagctag cctaccctgc aagtcaagag   420
gtgtccgtga ttcctagcca cctcaaggta tgcctctccc cggaaactgt ggccttttct   480
ggcacacatg atctccacga tttcaacata taaatagctt ttgataatgg caatattaat   540
caaatttatt ttacttcttt cttgtaacat ctctcttgta atcccttatt ccttctagct   600
atttttcata aaaaccaag caactgctta tcaacacaca aacactaaat caaaatgaac    660
gttgaaactt ctttgccagg ttcttctggt tctgacttgg aaactttcca ccacgaaacc   720
aagaagcatg ccaaccacga ctctggtatt tccgtcaacc atgaagctga aattggtgtt   780
aaccacactt tcgaaaagcc aggtccagtt ggtatcagag aaagattacg tcacttcacc   840
tgggcttggt acactttgac catgtcctgt ggtggtttgg ctttgttgat tgtcaaccaa   900
ccacacgact tcaagggttt gaaagatatt gccagagttg tctactgttt gaacttggct   960
ttctttgtta tcgttaccct ctttgatggc catcagattca tcttgcacaa gaacatgtgg  1020
gaatccttgg gtcacgacag agaaggtttg ttttttcccaa ctttctggtt atccattgct  1080
accatgatca ctggttttgta caagtgtttc ggtgatgatg ctaacgaaaa gttcaccaag  1140
tgtttgcaag ttttgttctg gatctactgt ggttgtacca tgatcactgc tgtcggtcaa  1200 tactcttttcg tctttgctac ccacaaatac gaattgcaca ccatgatgcc atcctggatc  1260
```

```
ttgccagctt tcccagttat gttgtctggt actatcgcct ccgtcatcgg ttctggtcaa    1320
ccagcttccg atggtattcc aattattatt gctggtatca ctttccaagg tttaggtttc    1380
tccatctcct tcatgatgta cgctcactac attggtagat tgatggaagt tggtttacca    1440
tctccagaac acagaccagg tatgttcatc tgtgttggtc ctccagcttt caccgctttg    1500
gctttggtcg gtatggccaa ggctttacca gacgacttcc aaattgtcgg tgaccctcac    1560
gctgtcattg acggtcgtgt tatgttgttc ttggctgtct ctgctgccat cttcttatgg    1620
gctttgtctt tctggttctt ctgtatcgct gttgttgctg ttgtcagatc tccaccaaag    1680
ggtttccatt tgaactggtt tgccatggtt ttcccaaaca ctggtttcac cttggctacc    1740
atcactttgg ctaacatgtt cgaatctcca ggtgtcaagg gtgttgccac tgctatgtcc    1800
ctatgtgtca tcatcatgtt tattttcgtc ttggtttctg ccatcagagc tgtcatcaga    1860
aaggacatca tgtggccagg tcaagatgaa gatgtttctg aataaagagt aataattatt    1920
gcttccatat aatatttta tacctcttt atttttatgt attagttaat taagtattt    1980 tatctatctg cttatcattt tcttttcata taggggggt tggtgttttc ttgcccatca    2040
gattgatgtc ctccaactcg gcactatttt acaaagggtt ttttgtaag agaaggagaa    2100 gacagatact aaaccatacg ttactcgaaa caaaaaaaaa aaaatggaa aaagctgcta    2160 tcaacaaaag acggcctcat caaacctaaa gaaccatgt cagcgtcctc aaataaccac    2220
aaacatcctt cccatatgct cggtcgtgct tgttgtacct                          2260
```

<210> SEQ ID NO 5
<211> LENGTH: 2432
<212> TYPE: DNA
<213> ORGANISM: Artificial Sequence
<220> FEATURE:
<223> OTHER INFORMATION: nucleotide sequence of fragment 6 (Figure 2),
    which includes malate dehydrogenase (MDH3) from S. cerevisiae
    codon pair optimized for expression in S. cerevisiae

<400> SEQUENCE: 5

```
aaataaccac aaacatcctt cccatatgct cggtcgtgct tgttgtacct gtgcttttct     60
ttttttgcgg tcaccccat gtggcgggga ggcagaggag taggtagagc aacgaatcct    120
actatttatc caaattagtc taggaactct ttttctagat tttttagatt tgagggcaag    180
cgctgttaac gactcagaaa tgtaagcact acggagtaga acgagaaatc cgccataggt    240
ggaaatccta gcaaaatctt gcttacccta gctagcctca ggtaagctag ccttagcctg    300
tcaaattttt ttcaaaattt ggtaagtttc tactagcaaa gcaaacacgg ttcaacaaac    360
cgaaaactcc actcattata cgtggaaacc gaaacaaaaa aacaaaaacc aaaatactcg    420
ccaatgagaa agttgctgcg tttctacttt cgaggaagag gaactgagag gattgactac    480
gaaaggggca aaaacgagtc gtattctccc attattgtct gctaccacgc ggtctagtag    540
aataagcaac cagtcaacgc taagacaggt aatcaaaata ccagtctgct ggctacgggc    600
tagtttttac ctcttttaga acccactgta aaagtccgtt gtaaagcccg ttctcactgt    660
tggcgttttt ttttttttgg tttagttct tattttcat ttttttcttt catgaccaaa    720
aacaaacaaa tctcgcgatt tgtactgcgg ccactggggc gtggccaaaa aaatgacaaa    780
tttagaaacc ttagtttctg atttttcctg ttatgaggag atatgataaa aaatattact    840
gctttattgt ttttttta tctactgaaa tagagaaact tacccaagga ggaggcaaaa    900
aaaagagtat atatacagca ggtaccattc agattttaat atattctttt ctcttcttct    960
```

| | |
|---|---|
| acactattat tataataatt ttactatatt cattttttagc ttaaaacctc atagaatatt | 1020 |
| attcttcagt cactcgctta aatacttatc aaaaatggtt aaggttgcca tcttaggtgc | 1080 |
| ttctggtggt gtcggtcaac cattatctct attattgaaa ttgtctccat acgtttctga | 1140 |
| attggctttg tacgatatca gagctgctga aggtattggt aaggatttgt cccacatcaa | 1200 |
| caccaactcc tcttgtgttg gttacgacaa ggattccatc gaaaacactt tgtccaatgc | 1260 |
| tcaagttgtc ttgattccag ctggtgttcc aagaaagcca ggtttgacca gagatgattt | 1320 |
| gttcaagatg aacgctggta tcgttaagtc tttggttact gctgtcggta aatttgcccc | 1380 |
| aaacgctcgt atcttagtca tctccaaccc tgttaactct ttggttccaa ttgccgttga | 1440 |
| aactttgaag aagatgggta agttcaagcc aggtaacgtt atgggtgtca ccaacttgga | 1500 |
| tttggtcaga gctgaaactt tcttggttga ctacttgatg ttgaagaacc aaagatcgg | 1560 |
| tcaagaacaa gacaagacca ccatgcacag aaaggtcacc gtcatcggtg gtcactctgg | 1620 |
| tgaaaccatc attccaatca tcactgacaa atccttggtt ttccaattgg acaagcaata | 1680 |
| cgaacatttc atccacagag tccaattcgg tggtgacgaa attgtcaagg ccaagcaagg | 1740 |
| tgccggttct gctaccttgt ccatggcttt cgctggtgcc aaatttgctg aagaagtctt | 1800 |
| acgttctttc cacaacgaaa agccagaaac tgaatctttg tctgctttcg tctacttgcc | 1860 |
| aggtttgaag aacggtaaga aggctcaaca attagtcggt gacaactcca ttgaatactt | 1920 |
| ctctttgcca attgttttga gaaacggttc cgttgtttcc attgacactt ctgttttgga | 1980 |
| aaaattgtct ccaagagaag aacaattggt caacactgct gtcaaggaat gagaaagaa | 2040 |
| cattgaaaag ggtaagtctt tcatcttgga cagttaaagt ctgaagaatg aatgatttga | 2100 |
| tgatttcttt ttccctccat ttttcttact gaatatatca atgatataga cttgtatagt | 2160 |
| ttattatttc aaattaagta gctatatata gtcaagataa cgtttgtttg acacgattac | 2220 |
| attattcgtc gacatctttt ttcagcctgt cgtggtagca atttgaggag tattattaat | 2280 |
| tgaataggtt cattttgcgc tcgcataaac agttttcgtc agggacagta tgttggaatg | 2340 |
| agtggtaatt aatggtgaca tgacatgtta tagcaatacc tcgaaaacctt cgaatccagc | 2400 |
| cagcatgtcg acacccacaa gatgtagtgc ac | 2432 |

<210> SEQ ID NO 6
<211> LENGTH: 2656
<212> TYPE: DNA
<213> ORGANISM: Artificial Sequence
<220> FEATURE:
<223> OTHER INFORMATION: nucleotide sequence of fragment 7 (Figure 2), which includes fumarase (fumB) from Escherichia coli codon pair optimized for expression in S. cerevisiae

<400> SEQUENCE: 6

| | |
|---|---|
| gaaaccttcg aatccagcca gcatgtcgac acccacaaga tgtagtgcac gtgcttagtc | 60 |
| aaaaaattag cctttttaatt ctgctgtaac ccgtacatgc ccaaaatagg gggcgggtta | 120 |
| cacagaatat ataacatcgt aggtgtctgg gtgaacagtt tattcctggc atccactaaa | 180 |
| tataatggag cccgcttttt aagctggcat ccagaaaaaa aaagaatccc agcaccaaaa | 240 |
| tattgttttc ttcaccaacc atcagttcat aggtccattc tcttagcgca actacagaga | 300 |
| acaggggcac aaacaggcaa aaacgggca caacctcaat ggagtgatgc aacctgcctg | 360 |
| gagtaaatga tgcacacaagg caattgaccc acgcatgtat ctatctcatt ttcttacacc | 420 |
| ttctattacc ttctgctctc tctgatttgg aaaaagctga aaaaaaggt tgaaccagt | 480 |
| tccctgaaat tattccccta cttgactaat aagtatataa agacggtagg tattgattgt | 540 |

```
aattctgtaa atctatttct taaacttctt aaattctact tttatagtta gtctttttt    600 tagttttaaa acaccaagaa cttagtttcg aataaacaca cataaacaaa caaaatgtcc   660
aacaagcctt tcatctacca agctccattc ccaatgggta aggacaacac tgaatactac   720
ttgttgactt ctgactacgt ttccgttgct gatttcgatg gtgaaaccat cttgaaggtt   780
gaaccagaag ccttgacttt gttggctcaa caagccttcc acgatgcttc tttcatgttg   840
cgtccagctc accaaaagca agttgctgcc attttgcacg acccagaagc ctccgaaaac   900
gacaaatacg ttgctttgca attcttgaga aactctgaaa ttgctgccaa gggtgtctta   960
ccaacttgtc aagacactgg tactgccatc attgtcggta agaagggtca aagagtctgg  1020
accggtggtg gtgacgaaga aactctatcc aagggtgttt acaacactta cattgaagat  1080
aatttacgtt actctcaaaa tgctgctttg gacatgtaca aggaagtcaa cactggtact  1140
aacttgccag ctcaaatcga cttatacgct gttgacggtg acgaatacaa gttcttgtgt  1200
gttgccaagg tggtggttc tgctaacaag acctacttgt accaagaaac caaggctttg  1260
ttgactccag gtaaattgaa gaacttcttg gtcgaaaaga tgagaacttt gggtactgct  1320
gcttgtccac ataccacat tgctttcgtt atcggtggta cttccgctga aaccaacttg  1380
aaaaccgtca aattggcttc cgctcactac tacgatgaat tgccaactga aggtaacgaa  1440
cacggtcaag ccttcagaga tgtccaattg gaacaagaat tgttggaaga agctcaaaaa  1500
ttaggtttgg gtgctcaatt tggtggtaaa actttgctc acgatatcag agttatcaga  1560
ttaccaagac atggtgcttc ttgtccagtt ggtatgggtg tttcctgttc tgctgacaga  1620
aacatcaagg ccaagatcaa cagagaaggt atctggattg aaaaattgga acacaaccca  1680
ggtcaataca tcccacaaga attgagacaa gctggtgaag tgaagctgt caaggttgac  1740 ttgaacagac caatgaagga atcttggct caattatctc aatacccagt tccaccaga   1800 ttatctttga ccggtactat cattgtcggt cgtgacattg ctcatgccaa gttgaaggaa  1860
ttgattgatg ctggtaagga attgcctcaa tacatcaagg accatccaat ctactacgct  1920
ggtccagcca agaccccagc tggttaccca tctggttctt gggtccaac caccgctggt  1980 agaatggact cttacgttga cttgctacaa tctcacggtg gttccatgat catgttggct  2040
aagggtaaca gatctcaaca agtcaccgat gcttgtcaca agcacggtgg tttctatttg  2100
ggttccattg gtggtccagc tgctgtcttg gctcaacaat ctatcaagca cttggaatgt  2160
gttgcttacc cagaattggg tatggaagcc atctggaaga ttgaagtcga agatttccca  2220
gctttcatct tagtcgatga caagggtaac gacttcttcc aacaaattgt caacaagcaa  2280
tgtgccaact gtaccaagta aaataaagca atcttgatga ggataatgat tttttttga   2340 atatacataa atactaccgt ttttctgcta gattttgtga agacgtaaat aagtacatat  2400
tactttttaa gccaagacaa gattaagcat taacttacc ctttttctctt ctaagtttca  2460 atactagtta tcactgttta aaagttatgg cgagaacgtc ggcggttaaa atatattacc  2520
ctgaacgtgg tgaattgaag ttctaggatg gtttaaagat ttttccttt tgggaaataa   2580 gtaaacaata tattgctgcc ttcctcaaag ccaaagttcg cgttccgacc ttgcctccca  2640
aatccgagtt gcgatt                                                  2656
```

<210> SEQ ID NO 7
<211> LENGTH: 4429
<212> TYPE: DNA
<213> ORGANISM: Artificial Sequence
<220> FEATURE:

<223> OTHER INFORMATION: nucleotide sequence of fragment 8 (Figure 2), which includes fumarate reductase from Trypanosoma brucei (FRDg) codon pair optimized for expression in S. cerevisiae

<400> SEQUENCE: 7

| | | | | | |
|---|---|---|---|---|---|
| aaagccaaag | ttcgcgttcc | gaccttgcct | cccaaatccg | agttgcgatt | gtgcttggct | 60 |
| gataatagcg | tataaacaat | gcatactttg | tacgttcaaa | atacaatgca | gtagatatat | 120 |
| ttatgcatat | tacatataat | acatatcaca | taggaagcaa | caggcgcgtt | ggactttaa | 180 |
| ttttcgagga | ccgcgaatcc | ttacatcaca | cccaatcccc | cacaagtgat | ccccacaca | 240 |
| ccatagcttc | aaaatgtttc | tactcctttt | ttactcttcc | agattttctc | ggactccgcg | 300 |
| catcgccgta | ccacttcaaa | acacccaagc | acagcatact | aaatttcccc | tctttcttcc | 360 |
| tctagggtgt | cgttaattac | ccgtactaaa | ggtttggaaa | agaaaaaaga | caccgcctcg | 420 |
| tttctttttc | ttcgtcgaaa | aaggcaataa | aaattttat | cacgtttctt | tttcttgaaa | 480 |
| atttttttt | ttgatttttt | tctctttcga | tgacctccca | ttgatattta | agttaataaa | 540 |
| cggtcttcaa | tttctcaagt | ttcagtttca | tttttcttgt | tctattacaa | cttttttac | 600 |
| ttcttgctca | ttagaaagaa | agcatagcaa | tctaatctaa | gttttaatta | caaaatggtt | 660 |
| gatggtagat | cttctgcttc | cattgttgcc | gttgacccag | aaaagagctgc | cagagaaaga | 720 |
| gatgctgctg | ccagagcttt | gttgcaagac | tctccattgc | acaccaccat | gcaatacgct | 780 |
| acctctggtt | tggaattgac | tgttccatac | gctttgaagg | ttgttgcttc | tgctgacact | 840 |
| ttcgacagag | ccaaggaagt | tgctgatgaa | gtcttgagat | gtgcctggca | attggctgac | 900 |
| accgttttga | actcttcaa | cccaaactct | gaagtctctt | tagtcggtag | attaccagtc | 960 |
| ggtcaaaagc | atcaaatgtc | tgctccattg | aaacgtgtca | tggcttgttg | tcaaagagtc | 1020 |
| tacaactcct | ctgctggttg | tttcgaccca | tccactgctc | cagttgccaa | ggctttgaga | 1080 |
| gaaattgctt | tgggtaagga | agaaacaat | gcttgtttgg | aagctttgac | tcaagcttgt | 1140 |
| accttgccaa | actcttttcgt | cattgattc | gaagctggta | ctatctccag | aaagcacgaa | 1200 |
| cacgcttctt | tggatttggg | tggtgtttcc | aagggttaca | tcgtcgatta | cgtcattgac | 1260 |
| aacatcaatg | ctgctggttt | ccaaaacgtt | ttctttgact | ggggtggtga | ctgtcgtgcc | 1320 |
| tccggtatga | acgccagaaa | cactccatgg | gttgtcggta | tcactagacc | tccttccttg | 1380 |
| gacatgttgc | caaaccctcc | aaaggaagct | tcttacatct | ccgtcatctc | tttggacaat | 1440 |
| gaagctttgg | ctacctctgg | tgattacgaa | aacttgatct | acactgctga | cgataaacca | 1500 |
| ttgacctgta | cctacgattg | gaaaggtaag | gaattgatga | agccatctca | atccaatatc | 1560 |
| gctcaagttt | ccgtcaagtg | ttactctgcc | atgtacgctg | acgctttggc | taccgcttgt | 1620 |
| ttcatcaagc | gtgacccagc | caaggtcaga | caattgttgg | atggttggag | atacgttaga | 1680 |
| gacaccgtca | gagattaccg | tgtctacgtc | agagaaaacg | aaagagttgc | caagatgttc | 1740 |
| gaaattgcca | ctgaagatgc | tgaaatgaga | aagagaagaa | tttccaacac | tttaccagct | 1800 |
| cgtgtcattg | ttgttggtgg | tggtttggct | ggtttgtccg | ctgccattga | agctgctggt | 1860 |
| tgtggtgctc | aagttgtttt | gatggaaaag | gaagccaagt | gggtggtaa | ctctgccaag | 1920 |
| gctacctctg | gtatcaacgg | ttggggtact | agagcccaag | ctaaggcttc | cattgtcgat | 1980 |
| ggtggtaagt | acttcgaaag | agatacctac | aagtctggta | tcggtggtaa | caccgatcca | 2040 |
| gctttggtta | agacttttgtc | catgaaatct | gctgacgcta | tcggttggtt | gacttctcta | 2100 |
| ggtgttccat | tgactgtttt | gtcccaatta | ggtggtcact | ccagaaagag | aactcacaga | 2160 |
| gccccagaca | agaaggatgg | tactccattg | ccaattggtt | tcaccatcat | gaaaactta | 2220 |

-continued

```
gaagatcatg ttagaggtaa cttgtccggt agaatcacca tcatggaaaa ctgttccgtt    2280
acctctttgt tgtctgaaac caaggaaaga ccagacggta ctaagcaaat cagagttacc    2340
ggtgtcgaat tcactcaagc tggttctggt aagaccacca ttttggctga tgctgttatc    2400
ttggccaccg gtggtttctc caacgacaag actgctgatt ctttgttgag agaacatgcc    2460
ccacacttgg ttaacttccc aaccaccaac ggtccatggg ctactggtga tggtgtcaag    2520
ttggctcaaa gattaggtgc tcaattggtc gatatgcaca aggttcaatt gcacccaact    2580
ggtttgatca acccaaagga cccagccaac ccaaccaaat tcttgggtcc agaagctcta    2640
agaggttctg gtggtgtttt gttgaacaaa caaggtaaga gatttgtcaa cgaattggat    2700
ttgagatctg ttgtttccaa ggccatcatg aacaaggtg ctgaataccc aggttctggt    2760
ggttccatgt ttgcttactg tgtcttgaac gctgctgctc aaaaattgtt tggtgtttcc    2820
tctcacgaat tctactggaa gaagatgggt ttgttcgtca aggctgacac catgagagac    2880
ttggctgctt tgattggttg tccagttgaa tccgttcaac aaactttaga agaatacgaa    2940
agattatcca tctctcaaag atcttgtcca attaccagaa aatctgttta cccatgtgtt    3000
ttgggtacta aggtccata ctatgtcgcc tttgtcactc catctatcca ctacaccatg    3060
ggtggttgtt tgatttctcc atctgctgaa atccaaatga gaacacttc ttccagagcc    3120 ccattgtccc actccaaccc aatcttgggt ttattcggtg ctggtgaagt caccggtggt    3180
gtccacggtg gtaacagatt aggtggtaac tctttgttgg aatgtgttgt tttcggtaga    3240
attgccggtg acagagcttc taccattttg caaagaaagt cctctgcttt gtctttcaag    3300
gtctggacca ctgttgtttt gagagaagtc agagaaggtg gtgtctacgg tgctggttcc    3360
cgtgtcttga gattcaactt accaggtgct ctacaaagat ctggtctatc cttgggtcaa    3420
ttcattgcca tcagaggtga ctgggacggt caacaattga ttggttacta ctctccaatc    3480
actttgccag acgatttggg tatgattgac attttggcca gatctgacaa gggtacttta    3540
cgtgaatgga tctctgcttt ggaaccaggt gacgctgtcg aaatgaaggc ttgtggtggt    3600
ttggtcatcg aaagaagatt atctgacaag cacttcgttt tcatgggtca cattatcaac    3660
aagctatgtt tgattgctgg tggtactggt gttgctccaa tgttgcaaat catcaaggcc    3720
gctttcatga agccattcat cgacactttg gaatccgtcc acttgatcta cgctgctgaa    3780
gatgtcactg aattgactta cagagaagtt ttggaagaac gtcgtcgtga atccagaggt    3840
aaattcaaga aaactttcgt tttgaacaga cctcctccat tatggactga cggtgtcggt    3900
ttcatcgacc gtggtatctt gaccaaccac gttcaaccac catctgacaa cttattggtt    3960
gccatctgtg gtccaccagt tatgcaaaga attgtcaagg ccactttaaa gactttaggt    4020
tacaacatga acttggtcag aaccgttgac gaaactgaac catctggaag ttaaaggaag    4080
tatctcggaa atattaattt aggccatgtc cttatgcacg tttcttttga tacttacggg    4140
tacatgtaca caagtatatc tatatatata aattaatgaa aatcccctat ttatatatat    4200
gactttaacg agacagaaca gttttttatt ttttatccta tttgatgaat gatacagttt    4260
cttattcacg tgttataccc acaccaaatc caatagcaat accggccatc acaatcactg    4320
tttcggcagc ccctaagatc agacaaaaca tccggaacca ccttaaatca acgtccctca    4380
gaaagcctgt atgcgaagcc acaatccttt ccaacagacc atactaagt              4429
```

<210> SEQ ID NO 8
<211> LENGTH: 1138
<212> TYPE: PRT

<213> ORGANISM: Trypanosoma brucei
<220> FEATURE:
<221> NAME/KEY: MISC_FEATURE
<222> LOCATION: (1)..(1138)
<223> OTHER INFORMATION: Fumarate reductase (FRDg)

<400> SEQUENCE: 8

```
Met Val Asp Gly Arg Ser Ser Ala Ser Ile Val Ala Val Asp Pro Glu
1               5                   10                  15

Arg Ala Ala Arg Glu Arg Asp Ala Ala Ala Arg Ala Leu Leu Gln Asp
            20                  25                  30

Ser Pro Leu His Thr Thr Met Gln Tyr Ala Thr Ser Gly Leu Glu Leu
        35                  40                  45

Thr Val Pro Tyr Ala Leu Lys Val Val Ala Ser Ala Asp Thr Phe Asp
50                  55                  60

Arg Ala Lys Glu Val Ala Asp Glu Val Leu Arg Cys Ala Trp Gln Leu
65                  70                  75                  80

Ala Asp Thr Val Leu Asn Ser Phe Asn Pro Asn Ser Glu Val Ser Leu
                85                  90                  95

Val Gly Arg Leu Pro Val Gly Gln Lys His Gln Met Ser Ala Pro Leu
            100                 105                 110

Lys Arg Val Met Ala Cys Cys Gln Arg Val Tyr Asn Ser Ser Ala Gly
        115                 120                 125

Cys Phe Asp Pro Ser Thr Ala Pro Val Ala Lys Ala Leu Arg Glu Ile
130                 135                 140

Ala Leu Gly Lys Glu Arg Asn Asn Ala Cys Leu Glu Ala Leu Thr Gln
145                 150                 155                 160

Ala Cys Thr Leu Pro Asn Ser Phe Val Ile Asp Phe Glu Ala Gly Thr
                165                 170                 175

Ile Ser Arg Lys His Glu His Ala Ser Leu Asp Leu Gly Gly Val Ser
            180                 185                 190

Lys Gly Tyr Ile Val Asp Tyr Val Ile Asp Asn Ile Asn Ala Ala Gly
        195                 200                 205

Phe Gln Asn Val Phe Phe Asp Trp Gly Gly Asp Cys Arg Ala Ser Gly
210                 215                 220

Met Asn Ala Arg Asn Thr Pro Trp Val Val Gly Ile Thr Arg Pro Pro
225                 230                 235                 240

Ser Leu Asp Met Leu Pro Asn Pro Pro Lys Glu Ala Ser Tyr Ile Ser
                245                 250                 255

Val Ile Ser Leu Asp Asn Glu Ala Leu Ala Thr Ser Gly Asp Tyr Glu
            260                 265                 270

Asn Leu Ile Tyr Thr Ala Asp Asp Lys Pro Leu Thr Cys Thr Tyr Asp
        275                 280                 285

Trp Lys Gly Lys Glu Leu Met Lys Pro Ser Gln Ser Asn Ile Ala Gln
290                 295                 300

Val Ser Val Lys Cys Tyr Ser Ala Met Tyr Ala Asp Ala Leu Ala Thr
305                 310                 315                 320

Ala Cys Phe Ile Lys Arg Asp Pro Ala Lys Val Arg Gln Leu Leu Asp
                325                 330                 335

Gly Trp Arg Tyr Val Arg Asp Thr Val Arg Asp Tyr Arg Val Tyr Val
            340                 345                 350

Arg Glu Asn Glu Arg Val Ala Lys Met Phe Glu Ile Ala Thr Glu Asp
        355                 360                 365

Ala Glu Met Arg Lys Arg Ile Ser Asn Thr Leu Pro Ala Arg Val
370                 375                 380
```

```
Ile Val Val Gly Gly Gly Leu Ala Gly Leu Ser Ala Ile Glu Ala
385                 390                 395                 400

Ala Gly Cys Gly Ala Gln Val Val Leu Met Glu Lys Glu Ala Lys Leu
        405                 410                 415

Gly Gly Asn Ser Ala Lys Ala Thr Ser Gly Ile Asn Gly Trp Gly Thr
            420                 425                 430

Arg Ala Gln Ala Lys Ala Ser Ile Val Asp Gly Gly Lys Tyr Phe Glu
        435                 440                 445

Arg Asp Thr Tyr Lys Ser Gly Ile Gly Gly Asn Thr Asp Pro Ala Leu
        450                 455                 460

Val Lys Thr Leu Ser Met Lys Ser Ala Asp Ala Ile Gly Trp Leu Thr
465                 470                 475                 480

Ser Leu Gly Val Pro Leu Thr Val Leu Ser Gln Leu Gly Gly His Ser
                485                 490                 495

Arg Lys Arg Thr His Arg Ala Pro Asp Lys Lys Asp Gly Thr Pro Leu
            500                 505                 510

Pro Ile Gly Phe Thr Ile Met Lys Thr Leu Glu Asp His Val Arg Gly
        515                 520                 525

Asn Leu Ser Gly Arg Ile Thr Ile Met Glu Asn Cys Ser Val Thr Ser
530                 535                 540

Leu Leu Ser Glu Thr Lys Glu Arg Pro Asp Gly Thr Lys Gln Ile Arg
545                 550                 555                 560

Val Thr Gly Val Glu Phe Thr Gln Ala Gly Ser Gly Lys Thr Thr Ile
                565                 570                 575

Leu Ala Asp Ala Val Ile Leu Ala Thr Gly Gly Phe Ser Asn Asp Lys
            580                 585                 590

Thr Ala Asp Ser Leu Leu Arg Glu His Ala Pro His Leu Val Asn Phe
        595                 600                 605

Pro Thr Thr Asn Gly Pro Trp Ala Thr Gly Asp Gly Val Lys Leu Ala
        610                 615                 620

Gln Arg Leu Gly Ala Gln Leu Val Asp Met Asp Lys Val Gln Leu His
625                 630                 635                 640

Pro Thr Gly Leu Ile Asn Pro Lys Asp Pro Ala Asn Pro Thr Lys Phe
                645                 650                 655

Leu Gly Pro Glu Ala Leu Arg Gly Ser Gly Gly Val Leu Leu Asn Lys
            660                 665                 670

Gln Gly Lys Arg Phe Val Asn Glu Leu Asp Leu Arg Ser Val Val Ser
        675                 680                 685

Lys Ala Ile Met Glu Gln Gly Ala Glu Tyr Pro Gly Ser Gly Gly Ser
        690                 695                 700

Met Phe Ala Tyr Cys Val Leu Asn Ala Ala Gln Lys Leu Phe Gly
705                 710                 715                 720

Val Ser Ser His Glu Phe Tyr Trp Lys Lys Met Gly Leu Phe Val Lys
                725                 730                 735

Ala Asp Thr Met Arg Asp Leu Ala Ala Leu Ile Gly Cys Pro Val Glu
            740                 745                 750

Ser Val Gln Gln Thr Leu Glu Glu Tyr Glu Arg Leu Ser Ile Ser Gln
        755                 760                 765

Arg Ser Cys Pro Ile Thr Arg Lys Ser Val Tyr Pro Cys Val Leu Gly
        770                 775                 780

Thr Lys Gly Pro Tyr Tyr Val Ala Phe Val Thr Pro Ser Ile His Tyr
785                 790                 795                 800
```

```
Thr Met Gly Gly Cys Leu Ile Ser Pro Ser Ala Glu Ile Gln Met Lys
            805                 810                 815

Asn Thr Ser Ser Arg Ala Pro Leu Ser His Ser Asn Pro Ile Leu Gly
        820                 825                 830

Leu Phe Gly Ala Gly Glu Val Thr Gly Val His Gly Gly Asn Arg
        835                 840                 845

Leu Gly Gly Asn Ser Leu Leu Glu Cys Val Val Phe Gly Arg Ile Ala
    850                 855                 860

Gly Asp Arg Ala Ser Thr Ile Leu Gln Arg Lys Ser Ser Ala Leu Ser
865                 870                 875                 880

Phe Lys Val Trp Thr Thr Val Val Leu Arg Glu Val Arg Glu Gly Gly
                885                 890                 895

Val Tyr Gly Ala Gly Ser Arg Val Leu Arg Phe Asn Leu Pro Gly Ala
            900                 905                 910

Leu Gln Arg Ser Gly Leu Ser Leu Gly Gln Phe Ile Ala Ile Arg Gly
        915                 920                 925

Asp Trp Asp Gly Gln Gln Leu Ile Gly Tyr Tyr Ser Pro Ile Thr Leu
    930                 935                 940

Pro Asp Asp Leu Gly Met Ile Asp Ile Leu Ala Arg Ser Asp Lys Gly
945                 950                 955                 960

Thr Leu Arg Glu Trp Ile Ser Ala Leu Glu Pro Gly Asp Ala Val Glu
                965                 970                 975

Met Lys Ala Cys Gly Gly Leu Val Ile Glu Arg Arg Leu Ser Asp Lys
            980                 985                 990

His Phe Val Phe Met Gly His Ile Ile Asn Lys Leu Cys Leu Ile Ala
        995                 1000                1005

Gly Gly Thr Gly Val Ala Pro Met Leu Gln Ile Ile Lys Ala Ala
    1010                1015                1020

Phe Met Lys Pro Phe Ile Asp Thr Leu Glu Ser Val His Leu Ile
    1025                1030                1035

Tyr Ala Ala Glu Asp Val Thr Glu Leu Thr Tyr Arg Glu Val Leu
    1040                1045                1050

Glu Glu Arg Arg Arg Glu Ser Arg Gly Lys Phe Lys Lys Thr Phe
    1055                1060                1065

Val Leu Asn Arg Pro Pro Leu Trp Thr Asp Gly Val Gly Phe
    1070                1075                1080

Ile Asp Arg Gly Ile Leu Thr Asn His Val Gln Pro Pro Ser Asp
    1085                1090                1095

Asn Leu Leu Val Ala Ile Cys Gly Pro Pro Val Met Gln Arg Ile
    1100                1105                1110

Val Lys Ala Thr Leu Lys Thr Leu Gly Tyr Asn Met Asn Leu Val
    1115                1120                1125

Arg Thr Val Asp Glu Thr Glu Pro Ser Gly
    1130                1135
```

<210> SEQ ID NO 9
<211> LENGTH: 20
<212> TYPE: DNA
<213> ORGANISM: Artificial Sequence
<220> FEATURE:
<223> OTHER INFORMATION: nucleotide sequence of the primer used to generate fragment 1 (Figure 2)

<400> SEQUENCE: 9
cattatatcg aggaaagccc                                              20

<210> SEQ ID NO 10
<211> LENGTH: 75
<212> TYPE: DNA
<213> ORGANISM: Artificial Sequence
<220> FEATURE:
<223> OTHER INFORMATION: nucleotide sequence of the primer used to generate fragment 1 (Figure 2)

<400> SEQUENCE: 10
aaagcaaagg aaggagagaa cagaggagta cttgtacgtt cgatgggcaa agaaagagac    60
acaaaactac gtggg                                                    75

<210> SEQ ID NO 11
<211> LENGTH: 20
<212> TYPE: DNA
<213> ORGANISM: Artificial Sequence
<220> FEATURE:
<223> OTHER INFORMATION: nucleotide sequence of the primer used to generate fragment 2 (Figure 2)

<400> SEQUENCE: 11
ttgcccatcg aacgtacaag                                               20

<210> SEQ ID NO 12
<211> LENGTH: 23
<212> TYPE: DNA
<213> ORGANISM: Artificial Sequence
<220> FEATURE:
<223> OTHER INFORMATION: nucleotide sequence of the primer used to generate fragment 2 (Figure 2)

<400> SEQUENCE: 12
tgctaagatt tgtgttcgtt tgg                                           23

<210> SEQ ID NO 13
<211> LENGTH: 20
<212> TYPE: DNA
<213> ORGANISM: Artificial Sequence
<220> FEATURE:
<223> OTHER INFORMATION: nucleotide sequence of the primer used to generate fragment 3 (Figure 2)

<400> SEQUENCE: 13
cggatcgatg tacacaaccg                                               20

<210> SEQ ID NO 14
<211> LENGTH: 23
<212> TYPE: DNA
<213> ORGANISM: Artificial Sequence
<220> FEATURE:
<223> OTHER INFORMATION: nucleotide sequence of the primer used to generate fragment 3 (Figure 2)

<400> SEQUENCE: 14
caacaggagg cggatggata tac                                           23

<210> SEQ ID NO 15
<211> LENGTH: 79
<212> TYPE: DNA
<213> ORGANISM: Artificial Sequence
<220> FEATURE:
<223> OTHER INFORMATION: nucleotide sequence of the primer used to generate fragment 4 (Figure 2)

<400> SEQUENCE: 15
acgctttccg gcatcttcca gaccacagta tatccatccg cctcctgttg tcgtacgctg    60
caggtcgacg aattctacc 79

<210> SEQ ID NO 16
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 4 (Figure 2)

<400> SEQUENCE: 16
gcggaatatt ggcggaacgg acacacgtgg atacaaacct ggacaacgtt taggccacta    60
gtggatctga tatcg                                                    75

<210> SEQ ID NO 17
<211> LENGTH: 22
<212> TYPE: DNA
<213> ORGANISM: Artificial Sequence
<220> FEATURE:
<223> OTHER INFORMATION: nucleotide sequence of the primer used to
      generate fragment 5 (Figure 2)

<400> SEQUENCE: 17
aacgttgtcc aggtttgtat cc                                            22

<210> SEQ ID NO 18
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 5 (Figure 2)

<400> SEQUENCE: 18
aggtacaaca agcacgaccg                                               20

<210> SEQ ID NO 19
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 6 (Figure 2) and fragments 120, 121, 122 and 123
      (Figure 7)

<400> SEQUENCE: 19
aaataaccac aaacatcctt ccc                                           23

<210> SEQ ID NO 20
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 6 (Figure 2) and fragments 120, 121, 122 and 123
      (Figure 7)

<400> SEQUENCE: 20
gtgcactaca tcttgtgggt gtc                                           23

<210> SEQ ID NO 21
<211> LENGTH: 22
<212> TYPE: DNA
<213> ORGANISM: Artificial Sequence
<220> FEATURE:
<223> OTHER INFORMATION: nucleotide sequence of the primer used to -continued generate fragment 7 (Figure 2)

<400> SEQUENCE: 21
gaaaccttcg aatccagcca gc                                                22

<210> SEQ ID NO 22
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 7 (Figure 2)

<400> SEQUENCE: 22
aatcgcaact cggatttggg                                                   20

<210> SEQ ID NO 23
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 8 (Figure 2)

<400> SEQUENCE: 23
aaagccaaag ttcgcgttcc                                                   20

<210> SEQ ID NO 24
<211> LENGTH: 24
<212> TYPE: DNA
<213> ORGANISM: Artificial Sequence
<220> FEATURE:
<223> OTHER INFORMATION: nucleotide sequence of the primer used to
      generate fragment 8 (Figure 2)

<400> SEQUENCE: 24
acttagtatg gtctgttgga aagg                                              24

<210> SEQ ID NO 25
<211> LENGTH: 25
<212> TYPE: DNA
<213> ORGANISM: Artificial Sequence
<220> FEATURE:
<223> OTHER INFORMATION: nucleotide sequence of the primer used to
      generate fragment 13 (Figure 3)

<400> SEQUENCE: 25
cggcattatt gtgtatggct caata                                             25

<210> SEQ ID NO 26
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 13 (Figure 3)

<400> SEQUENCE: 26
gaacttcgac ctgttgcaat acttcgggtt cggcacaaac gtgtacggat agggtttcaa       60
agatccatac ttctc                                                        75

<210> SEQ ID NO 27
<211> LENGTH: 79
<212> TYPE: DNA
<213> ORGANISM: Artificial Sequence
<220> FEATURE:

```
<223> OTHER INFORMATION: nucleotide sequence of the primer used to
      generate fragment 14 (Figure 4)

<400> SEQUENCE: 27
atccgtacac gtttgtgccg aacccgaagt attgcaacag gtcgaagttc tcgtacgctg    60
caggtcgacg aattctacc                                                  79

<210> SEQ ID NO 28
<211> LENGTH: 74
<212> TYPE: DNA
<213> ORGANISM: Artificial Sequence
<220> FEATURE:
<223> OTHER INFORMATION: nucleotide sequence of the primer used to
      generate fragment 115 (Figure 3) and fragment 14 (Figure 4)

<400> SEQUENCE: 28
aggtacaaca agcacgaccg agcatatggg aaggatgttt gtggttattt aggccactag    60
tggatctgat atcg                                                       74

<210> SEQ ID NO 29
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 15 (Figure 3) and fragments 17 to 110 (Figure 4)

<400> SEQUENCE: 29
aaataaccac aaacatcctt ccc                                             23

<210> SEQ ID NO 30
<211> LENGTH: 23
<212> TYPE: DNA
<213> ORGANISM: Artificial Sequence
<220> FEATURE:
<223> OTHER INFORMATION: nucleotide sequence of the primer used to
      generate fragment 15 (Figure 3) and fragments 17 to 110 (Figure 4)

<400> SEQUENCE: 30
gtgcactaca tcttgtgggt gtc                                             23

<210> SEQ ID NO 31
<211> LENGTH: 2033
<212> TYPE: DNA
<213> ORGANISM: Artificial Sequence
<220> FEATURE:
<223> OTHER INFORMATION: nucleotide sequence of fragment 15 (Figure 3)
      and fragment 120 (Figure 7), which includes the nucleotide
      sequence encoding SEQ ID NO: 39 codon pair optimized for
      expression in S. cerevisiae

<400> SEQUENCE: 31
taaataacca caaacatcct tcccatatgc tcggtcgtgc ttgttgtacc tgtgcttagt    60
caaaaaatta gccttttaat tctgctgtaa cccgtacatg cccaaaatag ggggcgggtt   120
acacagaata tataacatcg taggtgtctg ggtgaacagt ttattcctgg catccactaa   180
atataatgga gcccgctttt taagctggca tccagaaaaa aaagaatcc cagcaccaaa   240 atattgtttt cttcaccaac catcagttca taggtccatt ctcttagcgc aactacagag   300
aacaggggca caaacaggca aaaacgggc acaacctcaa tggagtgatg caacctgcct   360
ggagtaaatg atgacacaag gcaattgacc cacgcatgta tctatctcat tttcttacac   420
cttctattac cttctgctct ctctgatttg gaaaaagctg aaaaaaaagg ttgaaaccag   480
```

```
ttccctgaaa ttattcccct acttgactaa taagtatata aagacggtag gtattgattg       540
taattctgta aatctatttc ttaaacttct taaattctac ttttatagtt agtcttttt        600 ttagttttaa aacaccaaga acttagtttc gaataaacac acataaacaa acaaaatggt      660
taaggttgcc atcttaggtg cttctggtgg tgtcggtcaa ccattatctc tattattgaa      720
attgtctcca tacgtttctg aattggcttt gtacgatatc agagctgctg aaggtattgg      780
taaggatttg tcccacatca acaccaactc ctcttgtgtt ggttacgaca aggattccat      840
cgaaaacact ttgtccaatg ctcaagttgt cttgattcca gctggtgttc caagaaagcc      900
aggtttgacc agagatgatt tgttcaagat gaacgctggt atcgttaagt ctttggttac      960
tgctgtcggt aaatttgccc caaacgctcg tatcttagtc atctccaacc ctgttaactc     1020
tttggttcca attgccgttg aaactttgaa gaagatgggt aagttcaagc caggtaacgt     1080
tatgggtgtc accaacttgg atttggtcag agctgaaact ttcttggttg actacttgat     1140
gttgaagaac ccaaagatcg gtcaagaaca agacaagacc accatgcaca gaaaggtcac     1200
cgtcatcggt ggtcactctg gtgaaaccat cattccaatc atcactgaca aatccttggt     1260
tttccaattg gacaagcaat acgaacattt catccacaga gtccaattcg gtggtgacga     1320
aattgtcaag gccaagcaag gtgccggttc tgctaccttg tccatggctt tcgctggtgc     1380
caaatttgct gaagaagtct tacgttcttt ccacaacgaa aagccagaaa ctgaatcttt     1440
gtctgctttc gtctacttgc caggtttgaa gaacggtaag aaggctcaac aattagtcgg     1500
tgacaactcc attgaatact tctctttgcc aattgttttg agaaacggtt ccgttgtttc     1560
cattgacact tctgttttgg aaaaattgtc tccaagagaa gaacaattgg tcaacactgc     1620
tgtcaaggaa ttgagaaaga acattgaaaa gggtaagtct ttcatcttgg acagttaaag     1680
tctgaagaat gaatgatttg atgatttctt tttccctcca ttttcttac tgaatatatc      1740 aatgatatag acttgtatag tttattattt caaattaagt agctatatat agtcaagata     1800
acgtttgttt gacacgatta cattattcgt cgacatcttt tttcagcctg tcgtggtagc     1860
aatttgagga gtattattaa ttgaataggt tcattttgcg ctcgcataaa cagttttcgt     1920
cagggacagt atgttggaat gagtggtaat taatggtgac atgacatgtt atagcaaatac    1980 ctcgaaacct tcgaatccag ccagcatgtc gacacccaca agatgtagtg cac            2033
```

<210> SEQ ID NO 32
<211> LENGTH: 78
<212> TYPE: DNA
<213> ORGANISM: Artificial Sequence
<220> FEATURE:
<223> OTHER INFORMATION: nucleotide sequence of the primer used to
      generate fragment 16 (Figure 3)

<400> SEQUENCE: 32

```
gaaaccttcg aatccagcca gcatgtcgac acccacaaga tgtagtgcac acttttttta    60
gaatgacctg ttcccgac                                                   78
```

<210> SEQ ID NO 33
<211> LENGTH: 24
<212> TYPE: DNA
<213> ORGANISM: Artificial Sequence
<220> FEATURE:
<223> OTHER INFORMATION: nucleotide sequence of the primer used to
      generate fragment 16 (Figure 3)

<400> SEQUENCE: 33

```
cacaagctta ttcttccaaa aatc                                            24
```

<210> SEQ ID NO 34
<211> LENGTH: 3534
<212> TYPE: DNA
<213> ORGANISM: Artificial Sequence
<220> FEATURE:
<223> OTHER INFORMATION: nucleotide sequence of fragment 9 (Figure 1),
which includes fumarase from Rhizopus oryzae codon pair optimized
for expression in Saccharomyces cerevisiae

<400> SEQUENCE: 34

```
aaaggaggtg cacgcattat ggagaccact acgatacgat agctgcgttg ttgttgaagg      60
ggtttcttaa ggttgttttc gttgaaggta aatattggtc gttttttgtgc agcatattgt    120
cctctagatg caaactctgc aggtccattt gcagtaaagt gagttgcctc tcgaagaatc    180
attaatttcg tataaccgtc actattaaag tcagaaaata aattctgtcg tagacaatgt    240
taccataatg ttcttgtcca ttttgcatac actttaaata ttcatttgat ttctcagggt    300
tcatgatcat aataaattgc gcattcgcaa ggcggtagta ttataatggg gtccatcatt    360
ctgtagcaag aagttacagt acgctgttca agcgttaaac aagataagta atctcgaatg    420
aaacattcat atttcgcatg agccaacata cagttgctga gtaatcttca ttgcgcttat    480
ttatcggcat tgagattgta aaggaagtaa aacgcatttt tgcagatctg ttctcttatg    540
tatttttaat cgtccttgta tggaagtatc aaaggggacg ttcttcacct ccttggaagg    600
atcccttccc ttttacagtg cttcggaaaa gcacagcgtt gtccaaggga caaattttc     660
ttcaagttaa tgcataagaa atatcttttt ttatgtttag ctaagtaaaa gcagcttgga    720
gtaaaaaaaa aaatgagtaa atttctcgat ggattagttt ctcacaggta acataacaaa    780
aaccaagaaa agcccgcttc tgaaaactac agttgacttg tatgctaaag gccagacta    840
atgggaggag aaaaagaaac gaatgtatat gctcatttac actctatatc accatatgga    900
ggataagttg gctgagctt ctgatccaat ttattctatc cattagttgc tgatatgtcc    960
caccagccaa cacttgatag tatctactcg ccattcactt ccagcagcgc cagtagggtt   1020
gttgagctta gtaaaaatgt gcgcaccaca agcctacatg actccacgtc acatgaaacc   1080
acaccgtggg gccttgttgc gctaggaata ggatatgcga cgaagacgct tctgcttagt   1140
aaccacacca cattttcagg gggtcgatct gcttgcttcc tttactgtca cgagcggccc   1200
ataatcgcgc tttttttta aaaggcgcga dacagcaaac aggaagctcg ggtttcaacc   1260
ttcggagtgg tcgcagatct ggagactgga tctttacaat acagtaaggc aagccaccat   1320
ctgcttctta ggtgcatgcg acggtatcca cgtcagaac aacatagtct gaagaagggg   1380
gggaggagca tgttcattct ctgtagcagt aagagcttgg tgataatgac caaaactgga   1440
gtctcgaaat catataaata gacaatatat tttcacacaa tgagatttgt agtacagttc   1500
tattctctct cttgcataaa taagaaattc atcaagaact tggtttgata tttcaccaac   1560
acacacaaaa aacagtactt cactaaattt acacacaaaa caaatgtcc tctgcttctg    1620
ctgctttgca aaaattcaga gctgaaagag ataccttcgg tgacttgcaa gttccagctg   1680
accgttactg gggtgctcaa actcaaagat ctttgcaaaa ctttgacatt ggtggtccaa   1740
ctgaaagaat gccagaacca ttaatcagag ctttcggtgt tttgaagaag ctgctgcca    1800
ccgtcaacat gacctacggt ttggacccaa aggttggtga agccatccaa aaggctgctg   1860
acgaagttat cgatggttct ttgattgacc atttccatt ggttgtctgg caaaccggtt    1920
ctggtactca aaccaagatg aacgtcaatg aagtcatctc caacagagcc attgaattgt   1980
```

-continued

```
tgggtggtga attaggttcc aaggctccag tccacccaaa cgatcatgtc aacatgtctc    2040
aatcttccaa cgacactttc ccaactgcca tgcacgttgc tgccgttgtt gaaattcacg    2100
gtagattgat tccagctttg accactttga gagatgcttt gcaagccaaa tctgctgaat    2160
tcgaacacat catcaagatt ggtagaaccc acttgcaaga tgctaccccca ttgactttag    2220 gtcaagaatt ctccggttac actcaacaat tgacctacgg tattgctcgt gttcaaggta    2280
ctttggaaag attatacaac ttggctcaag gtgtactgc tgtcggtact ggtttgaaca    2340
ccagaaaggg tttcgatgcc aaggttgctg aagccattgc ttccatcact ggtttaccat    2400
tcaagaccgc tccaaacaaa ttcgaagctt ggctgctca cgacgctttg gttgaagctc    2460
acggtgcttt gaacaccgtt gcttgttctt tgatgaagat tgccaacgat atccgttact    2520
tgggttctgg tccaagatgt ggtttaggtg aattgtctct accagaaaac gaaccaggtt    2580
cttccatcat gccaggtaag gtcaacccaa ctcaatgtga agctatgacc atggtttgtg    2640
ctcaagtcat gggtaacaac actgccatct ctgttgctgg ttccaacggt caattcgaat    2700
tgaatgtctt taaccagtc atgatcaaga acttgatcca atccatcaga ttaatctctg    2760
acgcttccat ctcttttcacc aagaactgtg ttgtcggtat tgaagctaac gaaaagaaga    2820
tctcctccat catgaacgaa tctttgatgt tggtcactgc tttgaacccct cacattggtt    2880 acgacaaggc tgccaagtgt gccaagaagg ctcacaagga aggtaccact ttgaaagaag    2940
ctgctctatc tttggttac ttgacctctg aagaattcga ccaatgggtt agacctgagg    3000
acatgatttc tgccaaggat taaggcccgg gcataaagca atcttgatga ggataatgat    3060
ttttttttga atatacataa atactaccgt ttttctgcta gattttgtga agacgtaaat    3120
aagtacatat tactttttaa gccaagacaa gattaagcat taactttacc cttttctctt    3180
ctaagtttca atactagtta tcactgttta aaagttatgg cgagaacgtc ggcggttaaa    3240
atatattacc ctgaacgtgg tgaattgaag ttctaggatg gtttaaagat ttttccttt    3300 tgggaaataa gtaaacaata tattgctgcc tttgcaaaac gcacataccc acaatatgtg    3360
actattggca agaacgcat atcctttga agaggtggat actgatacta agagagtctc    3420
tattccggct ccacttttag tccagagatt acttgtcttc ttacgtatca gaacaagaaa    3480
gcatttccaa agtaattgca tttgcccttg agcagtatat atatactaag aagg         3534
```

<210> SEQ ID NO 35
<211> LENGTH: 2578
<212> TYPE: DNA
<213> ORGANISM: Artificial Sequence
<220> FEATURE:
<223> OTHER INFORMATION: nucleotide sequence of fragment 10 (Figure 1), which includes the 5' part of the Cre-recombinase

<400> SEQUENCE: 35

```
ttccaaagta attgcatttg cccttgagca gtatatatat actaagaagg tcgacctcga     60
gtaccgttcg tataatgtat gctatacgaa gttatattta aatcagtata gcgaccagca    120
ttcacatacg attgacgcat gatattactt tctgcgcact taacttcgca tctgggcaga    180
tgatgtcgag gcgaaaaaaa atataaatca cgctaacatt tgattaaaat agaacaacta    240
caatataaaa aaactataca aatgacaagt tcttgaaaac aagaatcttt ttattgtcag    300
tactgattag aaaaactcat cgagcatcaa atgaaactgc aatttattca tatcaggatt    360
atcaatacca tatttttgaa aaagccgttt ctgtaatgaa ggagaaaact caccgaggca    420
gttccatagg atggcaagat cctggtatcg gtctgcgatt ccgactcgtc caacatcaat    480
```

```
acaacctatt aatttcccct cgtcaaaaat aaggttatca agtgagaaat caccatgagt      540
gacgactgaa tccggtgaga atggcaaaag cttatgcatt tctttccaga cttgttcaac      600
aggccagcca ttacgctcgt catcaaaatc actcgcatca accaaaccgt tattcattcg      660
tgattgcgcc tgagcgagac gaaatacgcg atcgctgtta aaaggacaat acaaacagg       720 aatcgaatgc aaccggcgca ggaacactgc cagcgcatca acaatatttt caccctgaatc     780 aggatattct tctaatacct ggaatgctgt tttgccgggg atcgcagtgg tgagtaacca      840
tgcatcatca ggagtacgga taaaatgctt gatggtcgga agaggcataa attccgtcag      900
ccagtttagt ctgaccatct catctgtaac atcattggca acgctacctt tgccatgttt      960
cagaaacaac tctggcgcat cgggcttccc atacaatcga tagattgtcg cacctgattg     1020
cccgacatta tcgcgagccc atttatacccc atataaatca gcatccatgt tggaatttaa    1080
tcgcggcctc gaaacgtgag tcttttcctt acccatggtt gtttatgttc ggatgtgatg     1140
tgagaactgt atcctagcaa gattttaaaa ggaagtatat gaaagaagaa cctcagtggc     1200
aaatcctaac cttttatatt tctctacagg ggcgcggcgt ggggacaatt caacgcgtct     1260
gtgaggggag cgtttccctg ctcgcaggtc tgcagcgagg agccgtaatt tttgcttcgc     1320
gccgtgcggc catcaaaatg tatggatgca aatgattata catggggatg tatgggctaa     1380
atgtacgggc gacagtcaca tcatgccccct gagctgcgca cgtcaagact gtcaaggagg    1440
gtattctggg cctccatgtc atttaaatct agtacggatt agaagccgcc gagcgggtga     1500
cagccctccg aaggaagact ctcctccgtg cgtcctcgtc ttcaccggtc gcgttcctga     1560
aacgcagatg tgcctcgcgc cgcactgctc cgaacaataa agattctaca atactagctt     1620
ttatggttat gaagaggaaa aattggcagt aacctggccc cacaaacctt caaatgaacg     1680
aatcaaatta acaaccatag gatgataatg cgattagttt tttagcctta tttctggggt     1740
aattaatcag cgaagcgatg attttgatc tattaacaga tatataaatg caaaaactgc      1800
ataaccactt taactaatac tttcaacatt ttcggtttgt attacttctt attcaaatgt     1860
aataaaagta tcaacaaaaa attgttaata tacctctata ctttaacgtc aaggagaaaa     1920
aaccccggat tctagaacta gtggatcccc cgggctgcag gaattcgata tcaagcttat     1980
cgataccgtc gaggggcaga gccgatcctg tacactttac ttaaaaccat tatctgagtg     2040
ttaaatgtcc aatttactga ccgtacacca aaatttgcct gcattaccgg tcgatgcaac     2100
gagtgatgag gttcgcaaga acctgatgga catgttcagg gatcgccagg cgttttctga    2160
gcatacctgg aaaatgcttc tgtccgtttg ccggtcgtgg gcggcatggt gcaagttgaa     2220
taaccggaaa tggtttcccg cagaacctga agatgttcgc gattatcttc tatatcttca     2280
ggcgcgcggt ctggcagtaa aaactatcca gcaacatttg gccagctaa acatgcttca      2340 tcgtcggtcc gggctgccac gaccaagtga cagcaatgct gtttcactgg ttatgcggcg     2400
gatccgaaaa gaaaacgttg atgccggtga acgtgcaaaa caggctctag cgttcgaacg     2460
cactgatttc gaccaggttc gttcactcat ggaaaatagc gatcgctgcc aggatatacg     2520
taatctggca tttctgggga ttgcttataa caccctgtta cgtatagccg aaattgcc      2578
```

<210> SEQ ID NO 36
<211> LENGTH: 1263
<212> TYPE: DNA
<213> ORGANISM: Artificial Sequence
<220> FEATURE:
<223> OTHER INFORMATION: nucleotide sequence of fragment 11 (Figure 1),
      which includes the 3' part of the Cre-recombinase

<400> SEQUENCE: 36

```
cgttcactca tggaaaatag cgatcgctgc caggatatac gtaatctggc atttctgggg      60
attgcttata acaccctgtt acgtatagcc gaaattgcca ggatcagggt taaagatatc     120
tcacgtactg acggtgggag aatgttaatc catattggca gaacgaaaac gctggttagc     180
accgcaggtg tagagaaggc acttagcctg ggggtaacta aactggtcga gcgatggatt     240
tccgtctctg gtgtagctga tgatccgaat aactacctgt tttgccgggt cagaaaaaat     300
ggtgttgccg cgccatctgc caccagccag ctatcaactc gcgccctgga agggattttt     360
gaagcaactc atcgattgat ttacggcgct aaggatgact ctggtcagag atacctggcc     420
tggtctggac acagtgcccg tgtcggagcc gcgcgagata tgcccgcgc tggagtttca     480
ataccggaga tcatgcaagc tggtggctgg accaatgtaa atattgtcat gaactatatc     540
cgtaccctgg atagtgaaac aggggcaatg gtgcgcctgc tggaagatgg cgattagcca     600
ttaacgcgta aatgattgct ataattattt gatatttatg gtgacatatg agaaaggatt     660
tcaacatcga cggaaaatat gtagtgctgt ctgtaagcac taatattcag tcgccagccg     720
tcattgtcac tgtaaagctg agcgatagaa tgcctgatat tgactcaata tccgttgcgt     780
ttcctgtcaa agtatgcgt agtgctgaac atttcgtgat gaatgccacc gaggaagaag     840
cacggcgcgg ttttgcttaa agtgatgtct gagtttggcg aactcttggg taaggttgga     900
attgtcgacc tcgagtcatg taattagtta tgtcacgctt acattcacgc cctcccccca     960
catccgctct aaccgaaaag gaaggagtta gacaacctga agtctaggtc cctatttatt    1020
tttttatagt tatgttagta ttaagaacgt tatttatatt tcaaattttt ctttttttc    1080
tgtacagacg cgtgtacgca tgtaacatta tactgaaaac cttgcttgag aaggttttgg    1140
gacgctcgaa ggctttaatt tgcggccggt acataacttc gtataatgta tgctatacga    1200
acggtaggat ccggatggga cgtcagcact gtacttgttt ttgcgactag attgtaaatc    1260
att                                                                  1263
```

<210> SEQ ID NO 37
<211> LENGTH: 631
<212> TYPE: DNA
<213> ORGANISM: Artificial Sequence
<220> FEATURE:
<223> OTHER INFORMATION: nucleotide sequence of fragment 12 (Figure 1), which includes a region homologous to the YPRCtau3 locus

<400> SEQUENCE: 37

```
gatgggacgt cagcactgta cttgttttg cgactagatt gtaaatcatt ctttatttaa      60
tctctttctt taactactgc ttaaagtata atttggtccg tagtttaata actatactaa     120
gcgtaacaat gcatactgac attataagcc tgaacattac gagtttaagt tgtatgtagg     180
cgttctgtaa gaggttactg cgtaaattat caacgaatgc attggtgtat ttgcgaaagc     240
tacttctttt aacaagtatt tacataagaa taatggtgat ctgctcaact gatttggtga     300
taactctaac ttttttagca acaatttaaa agataattcg aacatatata acagtaggaa     360
gaatttgtgt acgtcaaatt aagataattt agcattacca agttattaa cctaaacata     420
aaatatatat gagacacatg tggaaatcgt atgaaacaac tgttatgaaa ctgacaagaa     480
tgaatatata gagtaagctc cgcttgtaaa gaggaatcac ttaagtgtat aaatgtctcg     540
acgattactt tagatccaag attgatgatt gatattactc tgtaatactt aagctctttt     600
aatagctcac tgttgtatta cgggctcgag t                                    631
```

<210> SEQ ID NO 38
<211> LENGTH: 1334
<212> TYPE: DNA
<213> ORGANISM: Artificial Sequence
<220> FEATURE:
<223> OTHER INFORMATION: nucleotide sequence of the PCR template for fragment 115 (Figure 3), fragment 14 (Figure 4) and fragment 117 (Figure 6), which includes the nourseothricin selection marker

<400> SEQUENCE: 38

```
tcgtacgctg caggtcgacg aattctaccg ttcgtataat gtatgctata cgaagttata      60
gatctgttta gcttgcctcg tccccgccgg gtcacccggc cagcgacatg gaggcccaga     120
ataccctcct tgacagtctt gacgtgcgca gctcaggggc atgatgtgac tgtcgcccgt     180
acatttagcc catacatccc catgtataat catttgcatc catacatttt gatggccgca     240
cggcgcgaag caaaaattac ggctcctcgc tgcagacctg cgagcaggga aacgctcccc     300
tcacagacgc gttgaattgt ccccacgccg cgcccctgta gagaaatata aaaggttagg     360
atttgccact gaggttcttc tttcatatac ttccttttaa aatcttgcta ggatacagtt     420
ctcacatcac atccgaacat aaacaaccat gggtaccact cttgacgaca cggcttaccg     480
gtaccgcacc agtgtcccgg gggacgccga ggccatcgag gcactggatg gtccttcac     540
caccgacacc gtcttccgcg tcaccgccac cggggacggc ttcacccttgc gggaggtgcc     600
ggtggacccg cccctgacca aggtgttccc cgacgacgaa tcggacgacg aatcggacga     660
cggggaggac ggcgacccgg actcccggac gttcgtcgcg tacggggacg acggcgacct     720
ggcgggcttc gtggtcgtct cgtactccgg ctggaaccgc cggctgaccg tcgaggacat     780
cgaggtcgcc ccggagcacc gggggcacgg ggtcgggcgc gcgttgatgg ggctcgcgac     840
ggagttcgcc cgcgagcggg gcgccgggca cctctggctg gaggtcacca acgtcaacgc     900
accggcgatc cacgcgtacc ggcggatggg gttcaccctc tgcggcctgg acaccgccct     960
gtacgacggc accgcctcgg acggcgagca ggcgctctac atgagcatgc cctgccccta    1020
atcagtactg acaataaaaa gattcttgtt ttcaagaact tgtcatttgt atagtttttt    1080
tatattgtag ttgttctatt ttaatcaaat gttagcgtga tttatatttt ttttcgcctc    1140
gacatcatct gcccagatgc gaagttaagt gcgcagaaag taatatcatg cgtcaatcgt    1200
atgtgaatgc tggtcgctat actgctgtcg attcgatact aacgccgcca tccagtgtcg    1260
aaaacgagct cataacttcg tataatgtat gctatacgaa cggtagaatt cgatatcaga    1320
tccactagtg gcct                                                      1334
```

<210> SEQ ID NO 39
<211> LENGTH: 340
<212> TYPE: PRT
<213> ORGANISM: Artificial Sequence
<220> FEATURE:
<223> OTHER INFORMATION: MDH3 lacking 3C-terminal peroxisomal targeting sequence

<400> SEQUENCE: 39

```
Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
        35                  40                  45

Asn Thr Asn Ser Ser Cys Val Gly Tyr Asp Lys Asp Ser Ile Glu Asn
```

```
            50                  55                  60
Thr Leu Ser Asn Ala Gln Val Val Leu Ile Pro Ala Gly Val Pro Arg
 65                  70                  75                  80

Lys Pro Gly Leu Thr Arg Asp Asp Leu Phe Lys Met Asn Ala Gly Ile
                 85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
            115                 120                 125

Glu Thr Leu Lys Lys Met Gly Lys Phe Lys Pro Gly Asn Val Met Gly
130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175

Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
            195                 200                 205

Tyr Glu His Phe Ile His Arg Val Gln Phe Gly Gly Asp Glu Ile Val
210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
            275                 280                 285

Phe Ser Leu Pro Ile Val Leu Arg Asn Gly Ser Val Val Ser Ile Asp
            290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 40
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 113 (Figure 2)

<400> SEQUENCE: 40
agaaagcctg tatgcgaagc cacaatcctt ccaacagac catactaagt acaggtgatt    60
gtatgtgggc ttatg                                                   75

<210> SEQ ID NO 41
<211> LENGTH: 29
<212> TYPE: DNA
<213> ORGANISM: Artificial Sequence
<220> FEATURE:
<223> OTHER INFORMATION: nucleotide sequence of the primer used to
      generate fragment 113 (Figure 2)
```

<400> SEQUENCE: 41
acattattgt aaaaacggag tagaaaggg                                29

<210> SEQ ID NO 42
<211> LENGTH: 2927
<212> TYPE: DNA
<213> ORGANISM: Artificial Sequence
<220> FEATURE:
<223> OTHER INFORMATION: nucleotide sequence of fragment 114 (Figure 3),
      which includes the expression cassette of ZWF1 from S. cerevisiae
      codon pair optimized for expression in S. cerevisiae

<400> SEQUENCE: 42

```
atccgtacac gtttgtgccg aacccgaagt attgcaacag gtcgaagttc gtgccaaagg      60
ggggcaggg acagggatac gacaagggct ggggaaaaaa aaaaagatag atacgattgg     120
ccgggtaagc ctggggaaat gtagcaagtg cgggtaagtt aaaaggtaac cacgtgactc     180
cggaagagtc acgtggttac ggacttttttt ctctagatct cagcttttta tcggtcttac    240
cctgccctcc tgcccctgc cccttccctt tgcccaaaa agaaaggaaa tctgttggat       300
ttcgctcagg ccatcccttt cgttaatatc ggttatcgct ttacacactg cacatccttc    360
tgtccaaaag gaatccagaa gtttagcttt tccttccttt cccacagaca ttagcctagg    420
ccctctctca tcatttgcat gcctcagcca atgtaccaag aataacgcaa cgaggttggg    480
aaattttaac ccaacaatcg atgcagatgt gacaagagat tagacacgtt ccagatacca    540
gattacacag cttgtgctag cagagtgaca tatggtggtg ttgtgtctcg tttagtacct    600
gtaatcgaga gtgttcaaat cagtcgattt gaacacccctt actgccactg aatattgatt    660
gaataccgtt tattgaaggt tttatgagtg atcttctttc ggtccaggac aatttgttga    720
gcttttttcta tgtagagttc cgtccctttt ttttttttttt ttgctttctc gcacttacta    780
gcactatttt tttttcacac actaaaacac tttattttaa tctatatata tatatatata    840
tatatgtagg aatggaatca cagacatttg atactcatcc tcatccttat taattcttgt    900
tttaatttgt ttgacttagc caaaccacca atctcaaccc atcgtatttc aggtattgtg    960
tgtctagtgt gtctctggta tacggaaata agtgccagaa gtaaggaaga aacaaagaac   1020
aagtgtctga atactactag cctctctttt cataatgagt gaaggccccg tcaaattcga   1080
aaaaaatacc gtcatatctg tctttggtgc gtcaggtgat ctggcaaaga agaagacttt   1140
tcccgcctta tttgggcttt tcagagaagg ttaccttgat ccatctacca agatcttcgg   1200
ttatgcccgg tccaaattgt ccatggagga ggacctgaag tcccgtgtcc taccccactt   1260
gaaaaaacct cacggtgaag ccgatgactc taaggtcgaa cagttcttca agatggtcag   1320
ctacatttcg ggaaattacg acacagatga aggcttcgac gaattaagaa cgcagatcga   1380
gaaattcgag aaaagtgcca acgtcgatgt cccacaccgt ctcttctatc tggccttgcc   1440
gccaagcgtt tttttgacgg tggccaagca gatcaagagt cgtgtgtacg cagagaatgg   1500
catcacccgt gtaatcgtag agaaaccttt cggccacgac ctggcctctg ccagggagct   1560
gcaaaaaaac ctggggcccc tctttaaaga agaagagttg tacagaattg accattactt   1620
gggtaaagag ttggtcaaga atcttttagt cttgaggttc ggtaaccagt ttttgaatgc   1680
ctcgtggaat agagacaaca ttcaaagcgt tcagatttcg tttaaagaga ggttcggcac   1740
cgaaggccgt ggcggctatt tcgactctat aggcataatc agagacgtga tgcagaacca   1800
tctgttacaa atcatgactc tcttgactat ggaaagaccg gtgtcttttg acccggaatc   1860
```

```
tattcgtgac gaaaaggtta aggttctaaa ggccgtggcc cccatcgaca cggacgacgt      1920
cctcttgggc cagtacggta aatctgagga cgggtctaag cccgcctacg tggatgatga      1980
cactgtagac aaggactcta aatgtgtcac ttttgcagca atgactttca acatcgaaaa      2040
cgagcgttgg gagggcgtcc ccatcatgat gcgtgccggt aaggctttga atgagtccaa      2100
ggtggagatc agactgcagt acaaagcggt cgcatcgggt gtcttcaaag acattccaaa      2160
taacgaactg gtcatcagag tgcagcccga tgccgctgtg tacctaaagt ttaatgctaa      2220 gaccectggt ctgtcaaatg ctacccaagt cacagatctg aatctaactt acgcaagcag      2280
gtaccaagac ttttggattc cagaggctta cgaggtgttg ataagagacg ccctactggg      2340
tgaccattcc aactttgtca gagatgacga attggatatc agttggggca tattcaccce      2400 attactgaag cacatagagc gtccggacgg tccaacaccg gaaatttacc cctacggatc      2460
aagaggtcca aagggattga aggaatatat gcaaaaacac aagtatgtta tgcccgaaaa      2520 gcaccettac gcttggcccg tgactaagcc agaagatacg aaggataatt aaaggagatt      2580
gataagactt ttctagttgc atatctttta tatttaaatc ttatctatta gttaattttt      2640
tgtaatttat ccttatatat agtctggtta ttctaaaata tcatttcagt atctaaaaat      2700 tccectcttt tttcagttat atcttaacag gcgacagtcc aaatgttgat ttatcccagt      2760
ccgattcatc agggttgtga agcattttgt caatggtcga aatcacatca gtaatagtgc      2820
ctcttacttg cctcatagaa tttctttctc ttaacgtcac cgtttggtct tttcctcacc      2880
cgatcccgaa gaaagtccaa ctccagttcg attccctgct ttcgagt                  2927
```

<210> SEQ ID NO 43
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 114 (Figure 3)

<400> SEQUENCE: 43
atccgtacac gtttgtgccg                                                    20

<210> SEQ ID NO 44
<211> LENGTH: 22
<212> TYPE: DNA
<213> ORGANISM: Artificial Sequence
<220> FEATURE:
<223> OTHER INFORMATION: nucleotide sequence of the primer used to
      generate fragment 114 (Figure 3)

<400> SEQUENCE: 44
actcgaaagc agggaatcga ac                                                 22

<210> SEQ ID NO 45
<211> LENGTH: 79
<212> TYPE: DNA
<213> ORGANISM: Artificial Sequence
<220> FEATURE:
<223> OTHER INFORMATION: nucleotide sequence of the primer used to
      generate fragment 115 (Figure 3)

<400> SEQUENCE: 45
acccgatccc gaagaaagtc caactccagt tcgattccct gctttcgagt tcgtacgctg      60
caggtcgacg aattctacc                                                     79

<210> SEQ ID NO 46

```
<211> LENGTH: 1180
<212> TYPE: PRT
<213> ORGANISM: Saccharomyces cerevisiae

<400> SEQUENCE: 46

Met Ser Ser Ser Lys Ile Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Gly Gln Tyr Thr Pro Val Gly Ala
65                  70                  75                  80

Tyr Leu Ala Met Asp Glu Ile Ile Glu Ile Ala Lys Lys His Lys Val
                85                  90                  95

Asp Phe Ile His Pro Gly Tyr Gly Phe Leu Ser Glu Asn Ser Glu Phe
                100                 105                 110

Ala Asp Lys Val Val Lys Ala Gly Ile Thr Trp Ile Gly Pro Pro Ala
            115                 120                 125

Glu Val Ile Glu Ser Val Gly Asp Lys Val Ser Ala Arg His Leu Ala
130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
            180                 185                 190

Arg Glu Gly Asp Asp Val Ala Asp Ala Phe Gln Arg Ala Thr Ser Glu
        195                 200                 205

Ala Arg Thr Ala Phe Gly Asn Gly Thr Cys Phe Val Glu Arg Phe Leu
    210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg His
                245                 250                 255

Gln Lys Val Val Glu Val Ala Pro Ala Lys Thr Leu Pro Arg Glu Val
                260                 265                 270

Arg Asp Ala Ile Leu Thr Asp Ala Val Lys Leu Ala Lys Val Cys Gly
            275                 280                 285

Tyr Arg Asn Ala Gly Thr Ala Glu Phe Leu Val Asp Asn Gln Asn Arg
        290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln
                325                 330                 335

Ala Ala Gly Ala Thr Leu Thr Gln Leu Gly Leu Leu Gln Asp Lys Ile
            340                 345                 350

Thr Thr Arg Gly Phe Ser Ile Gln Cys Arg Ile Thr Thr Glu Asp Pro
        355                 360                 365

Ser Lys Asn Phe Gln Pro Asp Thr Gly Arg Leu Glu Val Tyr Arg Ser
    370                 375                 380

Ala Gly Gly Asn Gly Val Arg Leu Asp Gly Gly Asn Ala Tyr Ala Gly
```

-continued

```
              385                 390                 395                 400
Ala Thr Ile Ser Pro His Tyr Asp Ser Met Leu Val Lys Cys Ser Cys
                    405                 410                 415

Ser Gly Ser Thr Tyr Glu Ile Val Arg Arg Lys Met Ile Arg Ala Leu
                    420                 425                 430

Ile Glu Phe Arg Ile Arg Gly Val Lys Thr Asn Ile Pro Phe Leu Leu
                    435                 440                 445

Thr Leu Leu Thr Asn Pro Val Phe Ile Glu Gly Thr Tyr Trp Thr Thr
                    450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
                    485                 490                 495

Ser Ser Ile Lys Gly Gln Ile Gly Leu Pro Lys Leu Lys Ser Asn Pro
                    500                 505                 510

Ser Val Pro His Leu His Asp Ala Gln Gly Asn Val Ile Asn Val Thr
                    515                 520                 525

Lys Ser Ala Pro Pro Ser Gly Trp Arg Gln Val Leu Leu Glu Lys Gly
                    530                 535                 540

Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
                    565                 570                 575

Val Arg Thr His Asp Leu Ala Thr Ile Ala Pro Thr Thr Ala His Ala
                    580                 585                 590

Leu Ala Gly Ala Phe Ala Leu Glu Cys Trp Gly Gly Ala Thr Phe Asp
                    595                 600                 605

Val Ala Met Arg Phe Leu His Glu Asp Pro Trp Glu Arg Leu Arg Lys
                    610                 615                 620

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
                    645                 650                 655

Phe Val Lys Gln Ala Lys Asp Asn Gly Val Asp Ile Phe Arg Val Phe
                    660                 665                 670

Asp Ala Leu Asn Asp Leu Glu Gln Leu Lys Val Gly Val Asn Ala Val
                    675                 680                 685

Lys Lys Ala Gly Gly Val Val Glu Ala Thr Val Cys Tyr Ser Gly Asp
                    690                 695                 700

Met Leu Gln Pro Gly Lys Lys Tyr Asn Leu Asp Tyr Tyr Leu Glu Val
705                 710                 715                 720

Val Glu Lys Ile Val Gln Met Gly Thr His Ile Leu Gly Ile Lys Asp
                    725                 730                 735

Met Ala Gly Thr Met Lys Pro Ala Ala Ala Lys Leu Leu Ile Gly Ser
                    740                 745                 750

Leu Arg Thr Arg Tyr Pro Asp Leu Pro Ile His Val His Ser His Asp
                    755                 760                 765

Ser Ala Gly Thr Ala Val Ala Ser Met Thr Ala Cys Ala Leu Ala Gly
                    770                 775                 780

Ala Asp Val Val Asp Val Ala Ile Asn Ser Met Ser Gly Leu Thr Ser
785                 790                 795                 800

Gln Pro Ser Ile Asn Ala Leu Leu Ala Ser Leu Glu Gly Asn Ile Asp
                    805                 810                 815
```

```
Thr Gly Ile Asn Val Glu His Val Arg Glu Leu Asp Ala Tyr Trp Ala
            820                 825                 830

Glu Met Arg Leu Leu Tyr Ser Cys Phe Glu Ala Asp Leu Lys Gly Pro
            835                 840                 845

Asp Pro Glu Val Tyr Gln His Glu Ile Pro Gly Gly Gln Leu Thr Asn
            850                 855                 860

Leu Leu Phe Gln Ala Gln Gln Leu Gly Leu Gly Glu Gln Trp Ala Glu
865                 870                 875                 880

Thr Lys Arg Ala Tyr Arg Glu Ala Asn Tyr Leu Leu Gly Asp Ile Val
            885                 890                 895

Lys Val Thr Pro Thr Ser Lys Val Val Gly Asp Leu Ala Gln Phe Met
            900                 905                 910

Val Ser Asn Lys Leu Thr Ser Asp Asp Ile Arg Arg Leu Ala Asn Ser
            915                 920                 925

Leu Asp Phe Pro Asp Ser Val Met Asp Phe Phe Glu Gly Leu Ile Gly
            930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
            965                 970                 975

Phe Asp Leu Glu Lys Ile Arg Glu Asp Leu Gln Asn Arg Phe Gly Asp
            980                 985                 990

Ile Asp Glu Cys Asp Val Ala Ser Tyr Asn Met Tyr Pro Arg Val Tyr
            995                 1000                1005

Glu Asp Phe Gln Lys Ile Arg Glu Thr Tyr Gly Asp Leu Ser Val
            1010                1015                1020

Leu Pro Thr Lys Asn Phe Leu Ala Pro Ala Glu Pro Asp Glu Glu
            1025                1030                1035

Ile Glu Val Thr Ile Glu Gln Gly Lys Thr Leu Ile Ile Lys Leu
            1040                1045                1050

Gln Ala Val Gly Asp Leu Asn Lys Lys Thr Gly Gln Arg Glu Val
            1055                1060                1065

Tyr Phe Glu Leu Asn Gly Glu Leu Arg Lys Ile Arg Val Ala Asp
            1070                1075                1080

Lys Ser Gln Asn Ile Gln Ser Val Ala Lys Pro Lys Ala Asp Val
            1085                1090                1095

His Asp Thr His Gln Ile Gly Ala Pro Met Ala Gly Val Ile Ile
            1100                1105                1110

Glu Val Lys Val His Lys Gly Ser Leu Val Lys Lys Gly Glu Ser
            1115                1120                1125

Ile Ala Val Leu Ser Ala Met Lys Met Glu Met Val Val Ser Ser
            1130                1135                1140

Pro Ala Asp Gly Gln Val Lys Asp Val Phe Ile Arg Asp Gly Glu
            1145                1150                1155

Ser Val Asp Ala Ser Asp Leu Leu Val Val Leu Glu Glu Glu Thr
            1160                1165                1170

Leu Pro Pro Ser Gln Lys Lys
            1175                1180

<210> SEQ ID NO 47
<211> LENGTH: 538
<212> TYPE: PRT
<213> ORGANISM: Artificial Sequence
<220> FEATURE:
```

<223> OTHER INFORMATION: amino acid sequence of phosphoenolpyruvate
carboxykinase from Actinobacillus succinogenes, with EGY to DAF
modification at position 120-122

<400> SEQUENCE: 47

```
Met Thr Asp Leu Asn Lys Leu Val Lys Glu Leu Asn Asp Leu Gly Leu
1               5                   10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Asp Ala Phe Cys Gly Ala Ser Glu Lys
        115                 120                 125

His Arg Ile Gly Val Arg Met Val Thr Glu Val Ala Trp Gln Ala His
130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
        275                 280                 285

Asn Leu Ser Gln Glu Asn Glu Pro Asp Ile Tyr Gly Ala Ile Arg Arg
290                 295                 300

Asp Ala Leu Leu Glu Asn Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
            340                 345                 350

Thr Lys Val Ile Phe Leu Thr Ala Asp Ala Phe Gly Val Leu Pro Pro
        355                 360                 365

Val Ser Lys Leu Thr Pro Glu Gln Thr Glu Tyr Tyr Phe Leu Ser Gly
370                 375                 380

Phe Thr Ala Lys Leu Ala Gly Thr Glu Arg Gly Val Thr Glu Pro Thr
```

```
                385                 390                 395                 400
Pro Thr Phe Ser Ala Cys Phe Gly Ala Ala Phe Leu Ser Leu His Pro
                    405                 410                 415

Ile Gln Tyr Ala Asp Val Leu Val Glu Arg Met Lys Ala Ser Gly Ala
                420                 425                 430

Glu Ala Tyr Leu Val Asn Thr Gly Trp Asn Gly Thr Gly Lys Arg Ile
            435                 440                 445

Ser Ile Lys Asp Thr Arg Gly Ile Ile Asp Ala Ile Leu Asp Gly Ser
        450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                    485                 490                 495

Thr Tyr Ala Asp Lys Ala Gln Trp Gln Val Lys Ala Glu Asp Leu Ala
                500                 505                 510

Asn Arg Phe Val Lys Asn Phe Val Lys Tyr Thr Ala Asn Pro Glu Ala
            515                 520                 525

Ala Lys Leu Val Gly Ala Gly Pro Lys Ala
        530                 535
```

<210> SEQ ID NO 48
<211> LENGTH: 548
<212> TYPE: PRT
<213> ORGANISM: Escherichia coli

<400> SEQUENCE: 48

```
Met Ser Asn Lys Pro Phe Ile Tyr Gln Ala Pro Phe Pro Met Gly Lys
1               5                   10                  15

Asp Asn Thr Glu Tyr Tyr Leu Leu Thr Ser Asp Tyr Val Ser Val Ala
                20                  25                  30

Asp Phe Asp Gly Glu Thr Ile Leu Lys Val Glu Pro Glu Ala Leu Thr
            35                  40                  45

Leu Leu Ala Gln Gln Ala Phe His Asp Ala Ser Phe Met Leu Arg Pro
        50                  55                  60

Ala His Gln Lys Gln Val Ala Ile Leu His Asp Pro Glu Ala Ser
65                  70                  75                  80

Glu Asn Asp Lys Tyr Val Ala Leu Gln Phe Leu Arg Asn Ser Glu Ile
                85                  90                  95

Ala Ala Lys Gly Val Leu Pro Thr Cys Gln Asp Thr Gly Thr Ala Ile
            100                 105                 110

Ile Val Gly Lys Lys Gly Gln Arg Val Trp Thr Gly Gly Gly Asp Glu
        115                 120                 125

Glu Thr Leu Ser Lys Gly Val Tyr Asn Thr Tyr Ile Glu Asp Asn Leu
130                 135                 140

Arg Tyr Ser Gln Asn Ala Ala Leu Asp Met Tyr Lys Glu Val Asn Thr
145                 150                 155                 160

Gly Thr Asn Leu Pro Ala Gln Ile Asp Leu Tyr Ala Val Asp Gly Asp
                165                 170                 175

Glu Tyr Lys Phe Leu Cys Val Ala Lys Gly Gly Gly Ser Ala Asn Lys
            180                 185                 190

Thr Tyr Leu Tyr Gln Glu Thr Lys Ala Leu Leu Thr Pro Gly Lys Leu
        195                 200                 205

Lys Asn Phe Leu Val Glu Lys Met Arg Thr Leu Gly Thr Ala Ala Cys
    210                 215                 220
```

```
Pro Pro Tyr His Ile Ala Phe Val Ile Gly Gly Thr Ser Ala Glu Thr
225                 230                 235                 240

Asn Leu Lys Thr Val Lys Leu Ala Ser Ala His Tyr Tyr Asp Glu Leu
                245                 250                 255

Pro Thr Glu Gly Asn Glu His Gly Gln Ala Phe Arg Asp Val Gln Leu
            260                 265                 270

Glu Gln Glu Leu Leu Glu Glu Ala Gln Lys Leu Gly Leu Gly Ala Gln
        275                 280                 285

Phe Gly Gly Lys Tyr Phe Ala His Asp Ile Arg Val Ile Arg Leu Pro
    290                 295                 300

Arg His Gly Ala Ser Cys Pro Val Gly Met Gly Val Ser Cys Ser Ala
305                 310                 315                 320

Asp Arg Asn Ile Lys Ala Lys Ile Asn Arg Glu Gly Ile Trp Ile Glu
                325                 330                 335

Lys Leu Glu His Asn Pro Gly Gln Tyr Ile Pro Gln Glu Leu Arg Gln
                340                 345                 350

Ala Gly Glu Gly Glu Ala Val Lys Val Asp Leu Asn Arg Pro Met Lys
            355                 360                 365

Glu Ile Leu Ala Gln Leu Ser Gln Tyr Pro Val Ser Thr Arg Leu Ser
370                 375                 380

Leu Thr Gly Thr Ile Ile Val Gly Arg Asp Ile Ala His Ala Lys Leu
385                 390                 395                 400

Lys Glu Leu Ile Asp Ala Gly Lys Glu Leu Pro Gln Tyr Ile Lys Asp
                405                 410                 415

His Pro Ile Tyr Tyr Ala Gly Pro Ala Lys Thr Pro Ala Gly Tyr Pro
            420                 425                 430

Ser Gly Ser Leu Gly Pro Thr Thr Ala Gly Arg Met Asp Ser Tyr Val
            435                 440                 445

Asp Leu Leu Gln Ser His Gly Gly Ser Met Ile Met Leu Ala Lys Gly
            450                 455                 460

Asn Arg Ser Gln Gln Val Thr Asp Ala Cys His Lys His Gly Gly Phe
465                 470                 475                 480

Tyr Leu Gly Ser Ile Gly Gly Pro Ala Ala Val Leu Ala Gln Gln Ser
                485                 490                 495

Ile Lys His Leu Glu Cys Val Ala Tyr Pro Glu Leu Gly Met Glu Ala
                500                 505                 510

Ile Trp Lys Ile Glu Val Glu Asp Phe Pro Ala Phe Ile Leu Val Asp
            515                 520                 525

Asp Lys Gly Asn Asp Phe Phe Gln Gln Ile Val Asn Lys Gln Cys Ala
530                 535                 540

Asn Cys Thr Lys
545

<210> SEQ ID NO 49
<211> LENGTH: 472
<212> TYPE: PRT
<213> ORGANISM: Artificial Sequence
<220> FEATURE:
<223> OTHER INFORMATION: amino acid sequence of fumarase from Rhizopus
      oryzae, lacking the first 23 N-terminal amino acids

<400> SEQUENCE: 49

Met Ser Ser Ala Ser Ala Ala Leu Gln Lys Phe Arg Ala Glu Arg Asp
1               5                   10                  15

Thr Phe Gly Asp Leu Gln Val Pro Ala Asp Arg Tyr Trp Gly Ala Gln
                20                  25                  30
```

```
Thr Gln Arg Ser Leu Gln Asn Phe Asp Ile Gly Gly Pro Thr Glu Arg
         35                  40                  45

Met Pro Glu Pro Leu Ile Arg Ala Phe Gly Val Leu Lys Lys Ala Ala
 50                  55                  60

Ala Thr Val Asn Met Thr Tyr Gly Leu Asp Pro Lys Val Gly Glu Ala
 65                  70                  75                  80

Ile Gln Lys Ala Ala Asp Glu Val Ile Asp Gly Ser Leu Ile Asp His
                 85                  90                  95

Phe Pro Leu Val Val Trp Gln Thr Gly Ser Gly Thr Gln Thr Lys Met
                100                 105                 110

Asn Val Asn Glu Val Ile Ser Asn Arg Ala Ile Glu Leu Leu Gly Gly
                115                 120                 125

Glu Leu Gly Ser Lys Ala Pro Val His Pro Asn Asp His Val Asn Met
130                 135                 140

Ser Gln Ser Ser Asn Asp Thr Phe Pro Thr Ala Met His Val Ala Ala
145                 150                 155                 160

Val Val Glu Ile His Gly Arg Leu Ile Pro Ala Leu Thr Thr Leu Arg
                165                 170                 175

Asp Ala Leu Gln Ala Lys Ser Ala Glu Phe Glu His Ile Ile Lys Ile
                180                 185                 190

Gly Arg Thr His Leu Gln Asp Ala Thr Pro Leu Thr Leu Gly Gln Glu
                195                 200                 205

Phe Ser Gly Tyr Thr Gln Gln Leu Thr Tyr Gly Ile Ala Arg Val Gln
210                 215                 220

Gly Thr Leu Glu Arg Leu Tyr Asn Leu Ala Gln Gly Gly Thr Ala Val
225                 230                 235                 240

Gly Thr Gly Leu Asn Thr Arg Lys Gly Phe Asp Ala Lys Val Ala Glu
                245                 250                 255

Ala Ile Ala Ser Ile Thr Gly Leu Pro Phe Lys Thr Ala Pro Asn Lys
                260                 265                 270

Phe Glu Ala Leu Ala Ala His Asp Ala Leu Val Glu Ala His Gly Ala
                275                 280                 285

Leu Asn Thr Val Ala Cys Ser Leu Met Lys Ile Ala Asn Asp Ile Arg
290                 295                 300

Tyr Leu Gly Ser Gly Pro Arg Cys Gly Leu Gly Glu Leu Ser Leu Pro
305                 310                 315                 320

Glu Asn Glu Pro Gly Ser Ser Ile Met Pro Gly Lys Val Asn Pro Thr
                325                 330                 335

Gln Cys Glu Ala Met Thr Met Val Cys Ala Gln Val Met Gly Asn Asn
                340                 345                 350

Thr Ala Ile Ser Val Ala Gly Ser Asn Gly Gln Phe Glu Leu Asn Val
                355                 360                 365

Phe Lys Pro Val Met Ile Lys Asn Leu Ile Gln Ser Ile Arg Leu Ile
370                 375                 380

Ser Asp Ala Ser Ile Ser Phe Thr Lys Asn Cys Val Val Gly Ile Glu
385                 390                 395                 400

Ala Asn Glu Lys Lys Ile Ser Ser Ile Met Asn Glu Ser Leu Met Leu
                405                 410                 415

Val Thr Ala Leu Asn Pro His Ile Gly Tyr Asp Lys Ala Ala Lys Cys
                420                 425                 430

Ala Lys Lys Ala His Lys Glu Gly Thr Thr Leu Lys Glu Ala Ala Leu
                435                 440                 445
```

-continued

```
Ser Leu Gly Tyr Leu Thr Ser Glu Glu Phe Asp Gln Trp Val Arg Pro
    450                 455                 460

Glu Asp Met Ile Ser Ala Lys Asp
465                 470

<210> SEQ ID NO 50
<211> LENGTH: 416
<212> TYPE: PRT
<213> ORGANISM: Aspergillus niger

<400> SEQUENCE: 50

Met Asn Val Glu Thr Ser Leu Pro Gly Ser Gly Ser Asp Leu Glu
1               5                   10                  15

Thr Phe His His Glu Thr Lys Lys His Ala Asn His Asp Ser Gly Ile
                20                  25                  30

Ser Val Asn His Glu Ala Glu Ile Gly Val Asn His Thr Phe Glu Lys
            35                  40                  45

Pro Gly Pro Val Gly Ile Arg Glu Arg Leu Arg His Phe Thr Trp Ala
        50                  55                  60

Trp Tyr Thr Leu Thr Met Ser Cys Gly Gly Leu Ala Leu Leu Ile Val
65                  70                  75                  80

Asn Gln Pro His Asp Phe Lys Gly Leu Lys Asp Ile Ala Arg Val Val
                85                  90                  95

Tyr Cys Leu Asn Leu Ala Phe Phe Val Ile Val Thr Ser Leu Met Ala
            100                 105                 110

Ile Arg Phe Ile Leu His Lys Asn Met Trp Glu Ser Leu Gly His Asp
        115                 120                 125

Arg Glu Gly Leu Phe Phe Pro Thr Phe Trp Leu Ser Ile Ala Thr Met
    130                 135                 140

Ile Thr Gly Leu Tyr Lys Cys Phe Gly Asp Asp Ala Asn Glu Lys Phe
145                 150                 155                 160

Thr Lys Cys Leu Gln Val Leu Phe Trp Ile Tyr Cys Gly Cys Thr Met
                165                 170                 175

Ile Thr Ala Val Gly Gln Tyr Ser Phe Val Phe Ala Thr His Lys Tyr
            180                 185                 190

Glu Leu His Thr Met Met Pro Ser Trp Ile Leu Pro Ala Phe Pro Val
        195                 200                 205

Met Leu Ser Gly Thr Ile Ala Ser Val Ile Gly Ser Gly Gln Pro Ala
    210                 215                 220

Ser Asp Gly Ile Pro Ile Ile Ala Gly Ile Thr Phe Gln Gly Leu
225                 230                 235                 240

Gly Phe Ser Ile Ser Phe Met Met Tyr Ala His Tyr Ile Gly Arg Leu
                245                 250                 255

Met Glu Val Gly Leu Pro Ser Pro Glu His Arg Pro Gly Met Phe Ile
            260                 265                 270

Cys Val Gly Pro Pro Ala Phe Thr Ala Leu Ala Leu Val Gly Met Ala
        275                 280                 285

Lys Ala Leu Pro Asp Asp Phe Gln Ile Val Gly Asp Pro His Ala Val
    290                 295                 300

Ile Asp Gly Arg Val Met Leu Phe Leu Ala Val Ser Ala Ala Ile Phe
305                 310                 315                 320

Leu Trp Ala Leu Ser Phe Trp Phe Cys Ile Ala Val Val Ala Val
                325                 330                 335

Val Arg Ser Pro Pro Lys Gly Phe His Leu Asn Trp Phe Ala Met Val
            340                 345                 350
```

```
Phe Pro Asn Thr Gly Phe Thr Leu Ala Thr Ile Thr Leu Ala Asn Met
            355                 360                 365

Phe Glu Ser Pro Gly Val Lys Gly Val Ala Thr Ala Met Ser Leu Cys
        370                 375                 380

Val Ile Ile Met Phe Ile Phe Val Leu Val Ser Ala Ile Arg Ala Val
385                 390                 395                 400

Ile Arg Lys Asp Ile Met Trp Pro Gly Gln Asp Glu Asp Val Ser Glu
                405                 410                 415

<210> SEQ ID NO 51
<211> LENGTH: 542
<212> TYPE: PRT
<213> ORGANISM: Kluyveromyces lactis

<400> SEQUENCE: 51

Met Val Ser Val Lys Ala Ser Ala Ala Glu Lys Lys Glu Phe Leu Gln
1               5                   10                  15

Ser Gln Ile Asp Glu Ile Glu Lys Trp Trp Ser Glu Pro Arg Trp Lys
            20                  25                  30

Asp Thr Lys Arg Ile Tyr Ser Ala Tyr Glu Ile Ala Lys Arg Arg Gly
        35                  40                  45

Ser Val Lys Pro Asn Thr Phe Pro Ser Thr Val Met Ser Gln Lys Leu
    50                  55                  60

Phe Lys Ile Leu Gly Glu His Ala Lys Asn Gly Thr Val Ser Lys Thr
65                  70                  75                  80

Phe Gly Ala Leu Asp Pro Val Gln Val Thr Gln Met Ser Lys Tyr Leu
                85                  90                  95

Asp Thr Ile Tyr Val Ser Gly Trp Gln Cys Ser Ser Thr Ala Ser Thr
            100                 105                 110

Ser Asn Glu Pro Gly Pro Asp Leu Ala Asp Tyr Pro Met Asp Thr Val
        115                 120                 125

Pro Asn Lys Val Glu His Leu Phe Lys Ala Gln Phe His Asp Arg
    130                 135                 140

Lys Gln Trp Glu Arg Ile Cys Asp Gly Thr Ile Glu Glu Ser Glu Ile
145                 150                 155                 160

Ile Asp Tyr Leu Thr Pro Ile Val Ala Asp Gly Asp Ala Gly His Gly
                165                 170                 175

Gly Leu Thr Ala Val Phe Lys Leu Thr Lys Met Phe Ile Glu Arg Gly
            180                 185                 190

Ala Ala Gly Ile His Ile Glu Asp Gln Thr Ser Thr Asn Lys Lys Cys
        195                 200                 205

Gly His Met Ala Gly Arg Cys Val Ile Pro Val Gln Glu His Ile Asn
    210                 215                 220

Arg Leu Ile Thr Cys Arg Met Ala Ala Asp Val Leu Gly Ser Asp Leu
225                 230                 235                 240

Ile Leu Val Ala Arg Thr Asp Ser Glu Ala Thr Leu Leu Ser Ser
                245                 250                 255

Thr Ala Asp Ser Arg Asp His Tyr Phe Ile Leu Gly Ala Ser Asn Pro
            260                 265                 270

Ala Val Lys Gly Lys Pro Leu Asn Asp Leu Leu Asn Lys Ala Ile Leu
        275                 280                 285

Asp Gly Ala Thr Ile Asp Leu Gln Thr Ile Glu Lys Glu Trp Leu
    290                 295                 300

Ala Lys Ala Asp Val Lys Leu Phe His Glu Val Phe Ala Asp Ala Ala
```

```
                         305                 310                 315
                                                                     320

Lys Ala Ala Gly Lys Asp Gln Ser Val Ile Asp Gln Phe Asn Ser Lys
                325                 330                 335

Val Asn Pro Leu Ser Glu Thr Ser Ile Tyr Glu Met Gln Ala Leu Ala
                340                 345                 350

Lys Glu Leu Leu Gly Thr Glu Leu Phe Phe Asp Trp Asp Leu Pro Arg
                355                 360                 365

Gly Arg Glu Gly Leu Tyr Arg Tyr Gln Gly Gly Thr Gln Cys Ser Val
            370                 375                 380

Met Arg Ala Arg Ala Phe Ala Pro Tyr Ala Asp Leu Cys Trp Met Glu
385                 390                 395                 400

Ser Asn Tyr Pro Asp Tyr Glu Gln Ala Lys Glu Phe Ala Glu Gly Val
                405                 410                 415

Thr Ala Lys Phe Pro Gly Lys Trp Met Ala Tyr Asn Leu Ser Pro Ser
                420                 425                 430

Phe Asn Trp Thr Lys Ala Met Ser Val Asp Glu Gln Glu Thr Phe Ile
            435                 440                 445

Gln Arg Leu Gly Asp Leu Gly Tyr Ile Trp Gln Phe Ile Thr Leu Ala
        450                 455                 460

Gly Leu His Thr Ser Gly Leu Ala Ile Glu Gln Phe Ser Lys Asn Phe
465                 470                 475                 480

Ala Lys Leu Gly Met Lys Ala Tyr Ala Gln Asp Ile Gln Lys Lys Glu
                485                 490                 495

Leu Asp Asn Gly Ile Asp Met Val Lys His Gln Lys Trp Ser Gly Ala
                500                 505                 510

Glu Tyr Ile Asp Gly Leu Leu Arg Leu Ala Gln Gly Leu Ala Ala
            515                 520                 525

Thr Ala Ala Met Gly Gln Gly Val Thr Glu Asp Gln Phe Lys
        530                 535                 540

<210> SEQ ID NO 52
<211> LENGTH: 551
<212> TYPE: PRT
<213> ORGANISM: Artificial Sequence
<220> FEATURE:
<223> OTHER INFORMATION: amino acid sequence of Saccharomyces cerevisiae
      peroxisomal malate synthase (Mls1) amino acid sequence, lacking
      the 3 C-terminal peroxisomal targeting sequence

<400> SEQUENCE: 52

Met Val Lys Val Ser Leu Asp Asn Val Lys Leu Leu Val Asp Val Asp
1               5                   10                  15

Lys Glu Pro Phe Phe Lys Pro Ser Ser Thr Val Gly Asp Ile Leu
                20                  25                  30

Thr Lys Asp Ala Leu Glu Phe Ile Val Leu Leu His Arg Thr Phe Asn
            35                  40                  45

Asn Lys Arg Lys Gln Leu Leu Glu Asn Arg Gln Val Val Gln Lys Lys
        50                  55                  60

Leu Asp Ser Gly Ser Tyr His Leu Asp Phe Leu Pro Glu Thr Ala Asn
65                  70                  75                  80

Ile Arg Asn Asp Pro Thr Trp Gln Gly Pro Ile Leu Ala Pro Gly Leu
                85                  90                  95

Ile Asn Arg Ser Thr Glu Ile Thr Gly Pro Pro Leu Arg Asn Met Leu
            100                 105                 110

Ile Asn Ala Leu Asn Ala Pro Val Asn Thr Tyr Met Thr Asp Phe Glu
        115                 120                 125
```

```
Asp Ser Ala Ser Pro Thr Trp Asn Asn Met Val Tyr Gly Gln Val Asn
        130                 135                 140

Leu Tyr Asp Ala Ile Arg Asn Gln Ile Asp Phe Asp Thr Pro Arg Lys
145                 150                 155                 160

Ser Tyr Lys Leu Asn Gly Asn Val Ala Asn Leu Pro Thr Ile Ile Val
                165                 170                 175

Arg Pro Arg Gly Trp His Met Val Glu Lys His Leu Tyr Val Asp Asp
            180                 185                 190

Glu Pro Ile Ser Ala Ser Ile Phe Asp Phe Gly Leu Tyr Phe Tyr His
        195                 200                 205

Asn Ala Lys Glu Leu Ile Lys Leu Gly Lys Gly Pro Tyr Phe Tyr Leu
    210                 215                 220

Pro Lys Met Glu His His Leu Glu Ala Lys Leu Trp Asn Asp Val Phe
225                 230                 235                 240

Cys Val Ala Gln Asp Tyr Ile Gly Ile Pro Arg Gly Thr Ile Arg Ala
                245                 250                 255

Thr Val Leu Ile Glu Thr Leu Pro Ala Ala Phe Gln Met Glu Glu Ile
                260                 265                 270

Ile Tyr Gln Leu Arg Gln His Ser Ser Gly Leu Asn Cys Gly Arg Trp
            275                 280                 285

Asp Tyr Ile Phe Ser Thr Ile Lys Arg Leu Arg Asn Asp Pro Asn His
        290                 295                 300

Ile Leu Pro Asn Arg Asn Gln Val Thr Met Thr Ser Pro Phe Met Asp
305                 310                 315                 320

Ala Tyr Val Lys Arg Leu Ile Asn Thr Cys His Arg Gly Val His
                325                 330                 335

Ala Met Gly Gly Met Ala Ala Gln Ile Pro Ile Lys Asp Asp Pro Ala
            340                 345                 350

Ala Asn Glu Lys Ala Met Thr Lys Val Arg Asn Asp Lys Ile Arg Glu
        355                 360                 365

Leu Thr Asn Gly His Asp Gly Ser Trp Val Ala His Pro Ala Leu Ala
    370                 375                 380

Pro Ile Cys Asn Glu Val Phe Ile Asn Met Gly Thr Pro Asn Gln Ile
385                 390                 395                 400

Tyr Phe Ile Pro Glu Asn Val Val Thr Ala Ala Asn Leu Leu Glu Thr
                405                 410                 415

Lys Ile Pro Asn Gly Glu Ile Thr Thr Glu Gly Ile Val Gln Asn Leu
                420                 425                 430

Asp Ile Gly Leu Gln Tyr Met Glu Ala Trp Leu Arg Gly Ser Gly Cys
        435                 440                 445

Val Pro Ile Asn Asn Leu Met Glu Asp Ala Ala Thr Ala Glu Val Ser
    450                 455                 460

Arg Cys Gln Leu Tyr Gln Trp Val Lys His Gly Val Thr Leu Lys Asp
465                 470                 475                 480

Thr Gly Glu Lys Val Thr Pro Glu Leu Thr Glu Lys Ile Leu Lys Glu
                485                 490                 495

Gln Val Glu Arg Leu Ser Lys Ala Ser Pro Leu Gly Asp Lys Asn Lys
            500                 505                 510

Phe Ala Leu Ala Ala Lys Tyr Phe Leu Pro Glu Ile Arg Gly Glu Lys
        515                 520                 525

Phe Ser Glu Phe Leu Thr Thr Leu Leu Tyr Asp Glu Ile Val Ser Thr
    530                 535                 540
```

```
Lys Ala Thr Pro Thr Asp Leu
545                 550
```

<210> SEQ ID NO 53
<211> LENGTH: 343
<212> TYPE: PRT
<213> ORGANISM: Saccharomyces cerevisiae

<400> SEQUENCE: 53

```
Met Val Lys Val Ala Ile Leu Gly Ala Ser Gly Gly Val Gly Gln Pro
1               5                   10                  15

Leu Ser Leu Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
            35                  40                  45

Asn Thr Asn Ser Ser Cys Val Gly Tyr Asp Lys Asp Ser Ile Glu Asn
        50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
                85                  90                  95

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
            115                 120                 125

Glu Thr Leu Lys Lys Met Gly Lys Phe Lys Pro Gly Asn Val Met Gly
        130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Gln Asp Lys Thr Thr
                165                 170                 175

Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
            195                 200                 205

Tyr Glu His Phe Ile His Arg Val Gln Phe Gly Gly Asp Glu Ile Val
        210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
            275                 280                 285

Phe Ser Leu Pro Ile Val Leu Arg Asn Gly Ser Val Val Ser Ile Asp
        290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser Ser Lys Leu
            340
```

<210> SEQ ID NO 54

```
<211> LENGTH: 25
<212> TYPE: DNA
<213> ORGANISM: Artificial Sequence
<220> FEATURE:
<223> OTHER INFORMATION: nucleotide sequence of the primer used to
      generate fragment 116 (Figure 6)

<400> SEQUENCE: 54
cggcattatt gtgtatggct caata                                          25

<210> SEQ ID NO 55
<211> LENGTH: 75
<212> TYPE: DNA
<213> ORGANISM: Artificial Sequence
<220> FEATURE:
<223> OTHER INFORMATION: nucleotide sequence of the primer used to
      generate fragment 116 (Figure 6)

<400> SEQUENCE: 55
gaacttcgac ctgttgcaat acttcgggtt cggcacaaac gtgtacggat agggtttcaa    60
agatccatac ttctc                                                     75

<210> SEQ ID NO 56
<211> LENGTH: 79
<212> TYPE: DNA
<213> ORGANISM: Artificial Sequence
<220> FEATURE:
<223> OTHER INFORMATION: nucleotide sequence of the primer used to
      generate fragment 117 (Figure 6)

<400> SEQUENCE: 56
atccgtacac gtttgtgccg aacccgaagt attgcaacag gtcgaagttc tcgtacgctg    60
caggtcgacg aattctacc                                                 79

<210> SEQ ID NO 57
<211> LENGTH: 74
<212> TYPE: DNA
<213> ORGANISM: Artificial Sequence
<220> FEATURE:
<223> OTHER INFORMATION: nucleotide sequence of the primer used to
      generate fragment 117 (Figure 6)

<400> SEQUENCE: 57
aatcgcaact cggatttggg aggcaaggtc ggaacgcgaa ctttggcttt aggccactag    60
tggatctgat atcg                                                      74

<210> SEQ ID NO 58
<211> LENGTH: 90
<212> TYPE: DNA
<213> ORGANISM: Artificial Sequence
<220> FEATURE:
<223> OTHER INFORMATION: nucleotide sequence of the primer used to
      generate fragment 119 (Figure 6)

<400> SEQUENCE: 58
agaaagcctg tatgcgaagc cacaatcctt ccaacagac catactaagt attttatttt     60
acttttttta gaatgacctg ttcccgacac                                     90

<210> SEQ ID NO 59
<211> LENGTH: 24
<212> TYPE: DNA
<213> ORGANISM: Artificial Sequence
<220> FEATURE:
<223> OTHER INFORMATION: nucleotide sequence of the primer used to
      generate fragment 119 (Figure 6)
```

-continued

<400> SEQUENCE: 59
cacaagctta ttcttccaaa aatc                                           24

<210> SEQ ID NO 60
<211> LENGTH: 20
<212> TYPE: DNA
<213> ORGANISM: Artificial Sequence
<220> FEATURE:
<223> OTHER INFORMATION: nucleotide sequence of the primer used to
      generate fragment 118 (Figure 6)

<400> SEQUENCE: 60
aaagccaaag ttcgcgttcc                                                20

<210> SEQ ID NO 61
<211> LENGTH: 24
<212> TYPE: DNA
<213> ORGANISM: Artificial Sequence
<220> FEATURE:
<223> OTHER INFORMATION: nucleotide sequence of the primer used to
      generate fragment 118 (Figure 6)

<400> SEQUENCE: 61
acttagtatg gtctgttgga aagg                                           24

<210> SEQ ID NO 62
<211> LENGTH: 4429
<212> TYPE: DNA
<213> ORGANISM: Artificial Sequence
<220> FEATURE:
<223> OTHER INFORMATION: nucleotide sequence of fragment 118 (Figure 6)
      which includes coding sequence for fumarate reductase from
      Trypanosoma brucei (FRDg) codon pair optimized for expression in
      S. cerevisiae

<400> SEQUENCE: 62
aaagccaaag ttcgcgttcc gaccttgcct cccaaatccg agttgcgatt gtgcttagtc      60
aaaaaattag cctttaatt ctgctgtaac ccgtacatgc ccaaatagg gggcgggtta      120 cacagaatat ataacatcgt aggtgtctgg gtgaacagtt tattcctggc atccactaaa    180
tataatggag cccgcttttt aagctggcat ccagaaaaaa aaagaatccc agcaccaaaa    240
tattgttttc ttcaccaacc atcagttcat aggtccattc tcttagcgca actacagaga    300 acagggggcac aaacaggcaa aaacgggca caacctcaat ggagtgatgc aacctgcctg     360
gagtaaatga tgacacaagg caattgaccc acgcatgtat ctatctcatt tcttacacc    420 ttctattacc ttctgctctc tctgatttgg aaaaagctga aaaaaaaggt tgaaaccagt    480
tccctgaaat tattccccta cttgactaat aagtatataa agacggtagg tattgattgt    540
aattctgtaa atctatttct taaacttctt aaattctact tttatagtta gtcttttttt    600
tagttttaaa acaccaagaa cttagtttcg aataaacaca cataaacaaa caaaatggtt    660
gatggtagat cttctgcttc cattgttgcc gttgacccag aaagagctgc cagagaaaga    720
gatgctgctg ccagagcttt gttgcaagac tctccattgc acaccaccat gcaatacgct    780
acctctggtt tggaattgac tgttccatac gctttgaagg ttgttgcttc tgctgacact    840
ttcgacagag ccaaggaagt tgctgatgaa gtcttgagat gtgcctggca attggctgac    900 accgtttttga actctttcaa cccaaactct gaagtctctt tagtcggtag attaccagtc    960
ggtcaaaagc atcaaatgtc tgctccattg aaacgtgtca tggcttgttg tcaaagagtc   1020
tacaactcct ctgctggttg tttcgaccca tccactgctc cagttgccaa ggctttgaga   1080

```
gaaattgctt tgggtaagga aagaaacaat gcttgtttgg aagctttgac tcaagcttgt   1140
accttgccaa actctttcgt cattgatttc gaagctggta ctatctccag aaagcacgaa   1200
cacgcttctt tggatttggg tggtgtttcc aagggttaca tcgtcgatta cgtcattgac   1260
aacatcaatg ctgctggttt ccaaaacgtt ttctttgact ggggtggtga ctgtcgtgcc   1320
tccggtatga acgccagaaa cactccatgg gttgtcggta tcactagacc tccttccttg   1380
gacatgttgc caaaccctcc aaaggaagct tcttacatct ccgtcatctc tttggacaat   1440
gaagctttgg ctacctctgg tgattacgaa aacttgatct acactgctga cgataaacca   1500
ttgacctgta cctacgattg gaaaggtaag gaattgatga agccatctca atccaatatc   1560
gctcaagttt ccgtcaagtg ttactctgcc atgtacgctg acgctttggc taccgcttgt   1620
ttcatcaagc gtgacccagc caaggtcaga caattgttgg atggttggag atacgttaga   1680
gacaccgtca gagattaccg tgtctacgtc agagaaaacg aaagagttgc caagatgttc   1740
gaaattgcca ctgaagatgc tgaaatgaga aagagaagaa tttccaacac tttaccagct   1800
cgtgtcattg ttgttggtgg tggtttggct ggtttgtccg ctgccattga agctgctggt   1860
tgtggtgctc aagttgtttt gatggaaaag gaagccaagt tgggtggtaa ctctgccaag   1920
gctacctctg gtatcaacgg ttggggtact agagcccaag ctaaggcttc cattgtcgat   1980
ggtggtaagt acttcgaaag agatacctac aagtctggta tcggtggtaa caccgatcca   2040
gctttggtta agactttgtc catgaaatct gctgacgcta tcggttggtt gacttctcta   2100
ggtgttccat tgactgtttt gtcccaatta ggtggtcact ccagaaagag aactcacaga   2160
gccccagaca agaaggatgg tactccattg ccaattggtt tcaccatcat gaaaactta   2220 gaagatcatg ttagaggtaa cttgtccggt agaatcacca tcatggaaaa ctgttccgtt   2280
acctctttgt tgtctgaaac caaggaaaga ccagacggta ctaagcaaat cagagttacc   2340
ggtgtcgaat tcactcaagc tggttctggt aagaccacca ttttggctga tgctgttatc   2400
ttggccaccg gtggtttctc caacgacaag actgctgatt ctttgttgag agaacatgcc   2460
ccacacttgg ttaacttccc aaccaccaac ggtccatggg ctactggtga tggtgtcaag   2520
ttggctcaaa gattaggtgc tcaattggtc gatatggaca aggttcaatt gcacccaact   2580
ggtttgatca acccaaagga cccagccaac ccaaccaaat tcttgggtcc agaagctcta   2640
agaggttctg tggtgttttt gttgaacaaa caaggtaaga gatttgtcaa cgaattggat   2700
ttgagatctg ttgttccaa ggccatcatg aacaaggtg ctgaatacc aggttctggt   2760 ggttccatgt tgcttactg tgtcttgaac gctgctgctc aaaaattgtt tggtgtttcc   2820
tctcacgaat tctactggaa gaagatgggt ttgttcgtca aggctgacac catgagagac   2880
ttggctgctt tgattggttg tccagttgaa tccgttcaac aaactttaga gaatacgaa   2940 agattatcca tctctcaaag atcttgtcca attaccagaa aatctgttta cccatgtgtt   3000
ttgggtacta aagtccata ctatgtcgcc tttgtcactc catctatcca ctacaccatg   3060
ggtggttgtt tgatttctcc atctgctgaa atccaaatga gaacacttc ttccagagcc   3120 ccattgtccc actccaaccc aatcttgggt ttattcggtg ctggtgaagt caccggtggt   3180
gtccacggtg gtaacagatt aggtggtaac tctttgttgg aatgtgttgt tttcggtaga   3240
attgccggtg acagagcttc taccattttg caaagaaagt cctctgcttt gtctttcaag   3300
gtctggacca ctgttgtttt gagagaagtc agagaaggtc gtgtctacgg tgctggttcc   3360
cgtgtcttga gattcaactt accaggtgct ctacaaagat ctggtctatc cttgggtcaa   3420
```

| | |
|---|---|
| ttcattgcca tcagaggtga ctgggacggt caacaattga ttggttacta ctctccaatc | 3480 |
| actttgccag acgatttggg tatgattgac attttggcca gatctgacaa gggtacttta | 3540 |
| cgtgaatgga tctctgcttt ggaaccaggt gacgctgtcg aaatgaaggc ttgtggtggt | 3600 |
| ttggtcatcg aaagaagatt atctgacaag cacttcgttt tcatgggtca cattatcaac | 3660 |
| aagctatgtt tgattgctgg tggtactggt gttgctccaa tgttgcaaat catcaaggcc | 3720 |
| gctttcatga agccattcat cgacactttg gaatccgtcc acttgatcta cgctgctgaa | 3780 |
| gatgtcactg aattgactta cagagaagtt ttggaagaac gtcgtcgtga atccagaggt | 3840 |
| aaattcaaga aaactttcgt tttgaacaga cctcctccat tatggactga cggtgtcggt | 3900 |
| ttcatcgacc gtggtatctt gaccaaccac gttcaaccac catctgacaa cttattggtt | 3960 |
| gccatctgtg gtccaccagt tatgcaaaga attgtcaagg ccactttaaa gactttaggt | 4020 |
| tacaacatga acttggtcag aaccgttgac gaaactgaac catctggaag ttaaaggaag | 4080 |
| tatctcggaa atattaattt aggccatgtc cttatgcacg tttctttttga tacttacggg | 4140 |
| tacatgtaca caagtatatc tatatatata aattaatgaa aatcccctat ttatatatat | 4200 |
| gactttaacg agacagaaca gttttttatt ttttatccta tttgatgaat gatacagttt | 4260 |
| cttattcacg tgttataccc acaccaaatc caatagcaat accggccatc acaatcactg | 4320 |
| tttcggcagc ccctaagatc agacaaaaca tccggaacca ccttaaatca acgtccctca | 4380 |
| gaaagcctgt atgcgaagcc acaatccttt ccaacagacc atactaagt | 4429 |

<210> SEQ ID NO 63
<211> LENGTH: 75
<212> TYPE: DNA
<213> ORGANISM: Artificial Sequence
<220> FEATURE:
<223> OTHER INFORMATION: nucleotide sequence of the primer used to
    generate fragment 124 (Figure 7)

<400> SEQUENCE: 63

| | |
|---|---|
| gaaaccttcg aatccagcca gcatgtcgac acccacaaga tgtagtgcac acaggtgatt | 60 |
| gtatgtgggc ttatg | 75 |

<210> SEQ ID NO 64
<211> LENGTH: 2032
<212> TYPE: DNA
<213> ORGANISM: Artificial Sequence
<220> FEATURE:
<223> OTHER INFORMATION: nucleotide sequence of fragment 121 (Figure 7)
    which includes coding sequence for S. cerevisiae MDH3 mutant
    MUT_014 codon pair optimized for expression in S. cerevisiae

<400> SEQUENCE: 64

| | |
|---|---|
| aaataaccac aaacatcctt cccatatgct cggtcgtgct tgttgtacct gtgcttagtc | 60 |
| aaaaaattag cctttttaatt ctgctgtaac ccgtacatgc ccaaaatagg gggcgggtta | 120 |
| cacagaatat ataacatcgt aggtgtctgg gtgaacagtt tattcctggc atccactaaa | 180 |
| tataatggag cccgcttttt aagctggcat ccagaaaaaa aagaatccc agcaccaaaa | 240 |
| tattgttttc ttcaccaacc atcagttcat aggtccattc tcttagcgca actacagaga | 300 |
| acagggcac aaacaggcaa aaaacgggca caacctcaat ggagtgatgc aacctgcctg | 360 |
| gagtaaatga tgcacaagg caattgaccc acgcatgtat ctatctcatt tcttacacc | 420 |
| ttctattacc ttctgctctc tctgatttgg aaaaagctga aaaaaaggt tgaaaccagt | 480 |
| tccctgaaat tattcccta cttgactaat aagtatataa agacggtagg tattgattgt | 540 |

-continued

```
aattctgtaa atctatttct taaacttctt aaattctact tttatagtta gtcttttttt    600
tagttttaaa acaccaagaa cttagtttcg aataaacaca cataaacaaa caaaatggtt    660
aaggttgcca tcttaggtgc ttctggtggt gtcggtcaac cattatctct attattgaaa    720
ttgtctccat acgttctga attggctttg tacggtatct ctgctgctga aggtattggt    780
aaggatttgt cccacatcaa caccaactcc tcttgtgttg ttacgacaa ggattccatc    840
gaaaacactt tgtccaatgc tcaagttgtc ttgattccag ctggtgttcc aagaaagcca    900
ggtttgacca gagatgattt gttcaagatg aacgctggta tcgttaagtc tttggttact    960
gctgtcggta aatttgcccc aaacgctcgt atcttagtca tctccaaccc tgttaactct   1020
ttggttccaa ttgccgttga aactttgaag aagatgggta agttcaagcc aggtaacgtt   1080
atgggtgtca ccaacttgga tttggtcaga gctgaaactt tcttggttga ctacttgatg   1140
ttgaagaacc caaagatcgg tcaagaacaa gacaagacca ccatgcacag aaaggtcacc   1200
gtcatcggtg tcactctggg tgaaaccatc attccaatca tcactgacaa atccttggtt   1260
ttccaattgg acaagcaata cgaacatttc atccacagag tccaattcgg tggtgacgaa   1320
attgtcaagg ccaagcaagg tgccggttct gctaccttgt ccatggcttt cgctggtgcc   1380
aaatttgctg aagaagtctt acgttctttc cacaacgaaa agccagaaac tgaatctttg   1440
tctgctttcg tctacttgcc aggttttgaag aacggtaaga aggctcaaca attagtcggt   1500
gacaactcca ttgaatactt ctctttgcca attgttttga aaacggttc cgttgtttcc   1560
attgacactt ctgttttgga aaaattgtct ccaagagaag aacaattggt caacactgct   1620
gtcaaggaat tgagaaagaa cattgaaaag ggtaagtctt tcatcttgga cagttaaagt   1680
ctgaagaatg aatgatttga tgatttcttt ttccctccat ttttcttact gaatatatca   1740
atgatataga cttgtatagt ttattattttc aaattaagta gctatatata gtcaagataa   1800
cgtttgtttg acacgattac attattcgtc gacatctttt ttcagcctgt cgtggtagca   1860
atttgaggag tattattaat tgaataggtt cattttgcgc tcgcataaac agttttcgtc   1920
agggacagta tgttggaatg agtggtaatt aatggtgaca tgacatgtta tagcaatacc   1980
tcgaaacctt cgaatccagc cagcatgtcg acacccacaa gatgtagtgc ac          2032
```

<210> SEQ ID NO 65
<211> LENGTH: 2032
<212> TYPE: DNA
<213> ORGANISM: Artificial Sequence
<220> FEATURE:
<223> OTHER INFORMATION: nucleotide sequence of fragment 122 (Figure 7) which includes coding sequence for S. cerevisiae MDH3 mutant MUT_015 codon pair optimized for expression in S. cerevisiae

<400> SEQUENCE: 65

```
aaataaccac aaacatcctt cccatatgct cggtcgtgct tgttgtacct gtgcttagtc     60
aaaaaattag cctttttaatt ctgctgtaac ccgtacatgc ccaaaatagg gggcgggtta    120
cacagaatat ataacatcgt aggtgtctgg gtgaacagtt tattcctggc atccactaaa    180
tataatggag cccgcttttt aagctggcat ccagaaaaaa aaagaatccc agcaccaaaa    240
tattgtttc ttcaccaacc atcagttcat aggtccattc tcttagcgca actacagaga    300
acaggggcac aaacaggcaa aaacgggca caacctcaat ggagtgatgc aacctgcctg    360
gagtaaatga tgcacaagg caattgaccc acgcatgtat ctatctcatt ttcttacacc    420
ttctattacc ttctgctctc tctgatttgg aaaaagctga aaaaaaaggt tgaaccagt    480
tccctgaaat tattccccta cttgactaat aagtatataa agacggtagg tattgattgt    540
```

```
aattctgtaa atctatttct taaacttctt aaattctact tttatagtta gtctttttt     600 tagttttaaa acaccaagaa cttagtttcg aataaacaca cataaacaaa caaaatggtt    660
aaggttgcca tcttaggtgc ttctggtggt gtcggtcaac cattatctct attattgaaa    720
ttgtctccat acgtttctga attggctttg tacggttcca gagctgctga aggtattggt    780
aaggatttgt cccacatcaa caccaactcc tcttgtgttg ttacgacaa ggattccatc     840 gaaaacactt gtccaatgc tcaagttgtc ttgattccag ctggtgttcc aagaaagcca     900
ggtttgacca gagatgattt gttcaagatg aacgctggta tcgttaagtc tttggttact    960
gctgtcggta aatttgcccc aaacgctcgt atcttagtca tctccaaccc tgttaactct   1020
ttggttccaa ttgccgttga aactttgaag aagatgggta agttcaagcc aggtaacgtt   1080
atgggtgtca ccaacttgga tttggtcaga gctgaaactt tcttggttga ctacttgatg   1140
ttgaagaacc caaagatcgg tcaagaacaa gacaagacca ccatgcacag aaaggtcacc   1200
gtcatcggtg tcactctgg tgaaaccatc attccaatca tcactgacaa atccttggtt    1260
ttccaattgg acaagcaata cgaacatttc atccacagag tccaattcgg tggtgacgaa   1320
attgtcaagg ccaagcaagg tgccggttct gctaccttgt ccatggcttt cgctggtgcc   1380
aaatttgctg aagaagtctt acgttctttc cacaacgaaa agccagaaac tgaatctttg   1440
tctgctttcg tctacttgcc aggtttgaag aacggtaaga aggctcaaca attagtcggt   1500
gacaactcca ttgaatactt ctctttgcca attgttttga gaaacggttc cgttgtttcc   1560
attgacactt ctgttttgga aaaattgtct ccaagagaag aacaattggt caacactgct   1620
gtcaaggaat tgagaaagaa cattgaaaag ggtaagtctt tcatcttgga cagttaaagt   1680
ctgaagaatg aatgatttga tgatttcttt ttccctccat ttttcttact gaatatatca   1740
atgatataga cttgtatagt ttattattc aaattaagta gctatatata gtcaagataa     1800
cgtttgtttg acacgattac attattcgtc gacatcttt ttcagcctgt cgtggtagca     1860
atttgaggag tattattaat tgaataggtt cattttgcgc tcgcataaac agttttcgtc   1920
agggacagta tgttggaatg agtggtaatt aatggtgaca tgacatgtta tagcaatacc   1980
tcgaaacctt cgaatccagc cagcatgtcg acacccacaa gatgtagtgc ac           2032
```

<210> SEQ ID NO 66
<211> LENGTH: 2032
<212> TYPE: DNA
<213> ORGANISM: Artificial Sequence
<220> FEATURE:
<223> OTHER INFORMATION: nucleotide sequence of fragment 123 (Figure 7) which includes coding sequence for S. cerevisiae MDH3 mutant MUT_034 codon pair optimized for expression in S. cerevisiae

<400> SEQUENCE: 66

```
aaataaccac aaacatcctt cccatatgct cggtcgtgct tgttgtacct gtgcttagtc     60
aaaaaattag ccttttaatt ctgctgtaac ccgtacatgc ccaaaatagg gggcgggtta    120
cacagaatat ataacatcgt aggtgtctgg gtgaacagtt tattcctggc atccactaaa    180
tataatggag cccgcttttt aagctggcat ccagaaaaaa aaagaatccc agcaccaaaa    240
tattgttttc ttcaccaacc atcagttcat aggtccattc tcttagcgca actacagaga    300 acagggcac aaacaggcaa aaacgggca caacctcaat ggagtgatgc aacctgcctg      360
gagtaaatga tgcacaagg caattgaccc acgcatgtat ctatctcatt ttcttacacc    420
ttctattacc ttctgctctc tctgatttgg aaaaagctga aaaaaaaggt tgaaaccagt   480
```

```
tccctgaaat tattccccta cttgactaat aagtatataa agacggtagg tattgattgt    540
aattctgtaa atctatttct taaacttctt aaattctact tttatagtta gtctttttt     600
tagttttaaa acaccaagaa cttagtttcg aataaacaca cataaacaaa caaaatggtt    660
aaggttgcca tcttaggtgc ttctggtggt gtcggtcaac cattatctct attattgaaa    720
ttgtctccat acgtttctga attggctttg tactcttctt ccaacgtcaa gggtattggt    780
aaggatttgt cccacatcaa caccaactcc tcttgtgttg gttacgacaa ggattccatc    840
gaaaacactt tgtccaatgc tcaagttgtc ttgattccag ctggtgttcc aagaaagcca    900
ggtttgacca gagatgattt gttcaagatg aacgctggta tcgttaagtc tttggttact    960
gctgtcggta aatttgcccc aaacgctcgt atcttagtca tctccaaccc tgttaactct   1020
ttggttccaa ttgccgttga aactttgaag aagatgggta agttcaagcc aggtaacgtt   1080
atgggtgtca ccaacttgga tttggtcaga gctgaaactt tcttggttga ctacttgatg   1140
ttgaagaacc caaagatcgg tcaagaacaa gacaagacca ccatgcacag aaaggtcacc   1200
gtcatcggtg tcactctggt gaaaccatc attccaatca tcactgacaa atccttggtt    1260
ttccaattgg acaagcaata cgaacatttc atccacagag tccaattcgg tggtgacgaa   1320
attgtcaagg ccaagcaagg tgccggttct gctaccttgt ccatggcttt cgctggtgcc   1380
aaatttgctg aagaagtctt acgttctttc cacaacgaaa agccagaaac tgaatctttg   1440
tctgctttcg tctacttgcc aggtttgaag aacggtaaga aggctcaaca attagtcggt   1500
gacaactcca ttgaatactt ctctttgcca attgttttga gaaacggttc cgttgtttcc   1560
attgacactt ctgttttgga aaaattgtct ccaagagaag aacaattggt caacactgct   1620
gtcaaggaat tgagaaagaa cattgaaaag ggtaagtctt tcatcttgga cagttaaagt   1680
ctgaagaatg aatgatttga tgatttcttt ttccctccat ttttcttact gaatatatca   1740
atgatataga cttgtatagt ttattatttc aaattaagta gctatatata gtcaagataa   1800
cgtttgtttg acacgattac attattcgtc gacatctttt ttcagcctgt cgtggtagca   1860
atttgaggag tattattaat tgaataggtt catttgcgc tcgcataaac agttttcgtc    1920
agggacagta tgttggaatg agtggtaatt aatggtgaca tgacatgtta tagcaatacc   1980
tcgaaacctt cgaatccagc cagcatgtcg acacccacaa gatgtagtgc ac           2032
```

<210> SEQ ID NO 67
<211> LENGTH: 499
<212> TYPE: PRT
<213> ORGANISM: Arabidopsis thaliana

<400> SEQUENCE: 67

```
Met Ala Ala Leu Thr Met Gln Phe Glu Gly Glu Lys Lys Asn Val Ser
1               5                   10                  15

Glu Val Ala Asp Val Thr Leu Lys Gln Glu Asp Glu Gln Gln Glu Arg
            20                  25                  30

Arg Ser Tyr Ser Thr Pro Phe Arg Glu Glu Arg Asp Thr Phe Gly Pro
        35                  40                  45

Ile Gln Val Pro Ser Asp Lys Leu Trp Gly Ala Gln Thr Gln Arg Ser
    50                  55                  60

Leu Gln Asn Phe Glu Ile Gly Gly Asp Arg Glu Arg Met Pro Glu Pro
65                  70                  75                  80

Ile Val Arg Ala Phe Gly Val Leu Lys Lys Cys Ala Ala Lys Val Asn
                85                  90                  95

Met Glu Tyr Gly Leu Asp Pro Met Ile Gly Glu Ala Ile Met Glu Ala
```

```
                100                 105                 110
Ala Gln Glu Val Ala Glu Gly Lys Leu Asn Asp His Phe Pro Leu Val
            115                 120                 125

Val Trp Gln Thr Gly Ser Gly Thr Gln Ser Asn Met Asn Ala Asn Glu
        130                 135                 140

Val Ile Ala Asn Arg Ala Ala Glu Ile Leu Gly His Lys Arg Gly Glu
145                 150                 155                 160

Lys Ile Val His Pro Asn Asp His Val Asn Arg Ser Gln Ser Ser Asn
                165                 170                 175

Asp Thr Phe Pro Thr Val Met His Ile Ala Ala Thr Glu Ile Thr
            180                 185                 190

Ser Arg Leu Ile Pro Ser Leu Lys Asn Leu His Ser Ser Leu Glu Ser
        195                 200                 205

Lys Ser Phe Glu Phe Lys Asp Ile Val Lys Ile Gly Arg Thr His Thr
    210                 215                 220

Gln Asp Ala Thr Pro Leu Thr Leu Gly Gln Glu Phe Gly Gly Tyr Ala
225                 230                 235                 240

Thr Gln Val Glu Tyr Gly Leu Asn Arg Val Ala Cys Thr Leu Pro Arg
                245                 250                 255

Ile Tyr Gln Leu Ala Gln Gly Gly Thr Ala Val Gly Thr Gly Leu Asn
            260                 265                 270

Thr Lys Lys Gly Phe Asp Val Lys Ile Ala Ala Ala Val Ala Glu Glu
        275                 280                 285

Thr Asn Leu Pro Phe Val Thr Ala Glu Asn Lys Phe Glu Ala Leu Ala
    290                 295                 300

Ala His Asp Ala Cys Val Glu Thr Ser Gly Ser Leu Asn Thr Ile Ala
305                 310                 315                 320

Thr Ser Leu Met Lys Ile Ala Asn Asp Ile Arg Phe Leu Gly Ser Gly
                325                 330                 335

Pro Arg Cys Gly Leu Gly Glu Leu Ser Leu Pro Glu Asn Glu Pro Gly
            340                 345                 350

Ser Ser Ile Met Pro Gly Lys Val Asn Pro Thr Gln Cys Glu Ala Leu
        355                 360                 365

Thr Met Val Cys Ala Gln Val Met Gly Asn His Val Ala Val Thr Ile
    370                 375                 380

Gly Gly Ser Asn Gly His Phe Glu Leu Asn Val Phe Lys Pro Val Ile
385                 390                 395                 400

Ala Ser Ala Leu Leu His Ser Ile Arg Leu Ile Ala Asp Ala Ser Ala
                405                 410                 415

Ser Phe Glu Lys Asn Cys Val Arg Gly Ile Glu Ala Asn Arg Glu Arg
            420                 425                 430

Ile Ser Lys Leu Leu His Glu Ser Leu Met Leu Val Thr Ser Leu Asn
        435                 440                 445

Pro Lys Ile Gly Tyr Asp Asn Ala Ala Ala Val Ala Lys Arg Ala His
    450                 455                 460

Lys Glu Gly Cys Thr Leu Lys His Ala Ala Met Lys Leu Gly Val Leu
465                 470                 475                 480

Thr Ser Glu Glu Phe Asp Thr Leu Val Val Pro Glu Lys Met Ile Gly
                485                 490                 495

Pro Ser Asp
```